United States Patent
Kehler et al.

(10) Patent No.: US 7,834,008 B2
(45) Date of Patent: Nov. 16, 2010

(54) CYCLOPROPYL DERIVATIVES AS NK3 RECEPTOR ANTAGONISTS

(75) Inventors: Jan Kehler, Kgs. Lyngby (DK); Tore Hansen, Oslo (NO); Anders Poulsen, Singapore (SG); Berith Bjørnholm, Værløse (DK); Thomas Ruhland, Roskilde (DK); Morten Bang Nørgaard, Lyngby (DK); Søren Møller Nielsen, Hillerød (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 1071 days.

(21) Appl. No.: 10/568,483

(22) PCT Filed: Aug. 13, 2004

(86) PCT No.: PCT/DK2004/000538

§ 371 (c)(1),
(2), (4) Date: Aug. 14, 2006

(87) PCT Pub. No.: WO2005/016884

PCT Pub. Date: Feb. 24, 2005

(65) Prior Publication Data

US 2006/0281746 A1 Dec. 14, 2006

Related U.S. Application Data

(60) Provisional application No. 60/501,535, filed on Sep. 8, 2003.

(30) Foreign Application Priority Data

Aug. 15, 2003 (DK) ................. 2003 01175

(51) Int. Cl.
- A61K 31/54 (2006.01)
- A61K 31/44 (2006.01)
- C07D 513/00 (2006.01)
- C07D 295/00 (2006.01)
- C07D 471/00 (2006.01)

(52) U.S. Cl. ............... 514/222.5; 514/223.2; 514/226.5; 514/230.5; 514/252.13; 514/278; 544/48; 544/70; 544/386; 544/392; 544/393; 544/398; 546/16; 546/17; 546/19; 546/20

(58) Field of Classification Search .............. 514/222.5, 514/223.2, 226.5, 230, 5, 252.13; 544/48, 544/70, 386, 392, 393, 3; 546/16, 17, 19
See application file for complete search history.

(56) References Cited

U.S. PATENT DOCUMENTS

| 4,478,836 A | 10/1984 | Mouzin et al. |
| 5,434,158 A | 7/1995 | Shah et al. |

FOREIGN PATENT DOCUMENTS

| EP | 0068999 | 1/1983 |
| EP | 0673928 | 9/1995 |
| WO | WO 97/10211 | 3/1997 |
| WO | WO 03/051869 | 6/2003 |

OTHER PUBLICATIONS

Bonnaud, B. et al. (1987) "1-Aryl-2-(aminomethyl)cyclopropancarboxylic acid derivatives. A new series of potential antidepreassants", Journal of Medicinal Chemistry; 30(2): 318-325.

Primary Examiner—Janet L. Andres
Assistant Examiner—Raymond Covington
(74) Attorney, Agent, or Firm—Stephen G. Kalinchak; Margaret M. Buck; Mary C. Johnson

(57) ABSTRACT

The present invention relates to cyclopropyl derivatives of formula (I) and salt thereof. These compounds are NK3 receptor antagonists and may therefore be useful for treatment of diseases where the NK3 receptor is implicated, e.g. psychotic disorders.

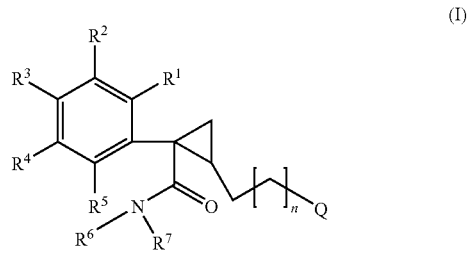

(I)

118 Claims, No Drawings

CYCLOPROPYL DERIVATIVES AS NK3 RECEPTOR ANTAGONISTS

This application is a §371 national stage of PCT International Application No. PCT/DK2004/000538, filed Aug. 13, 2004, which claims priority under 35 U.S.C. §119(a)-(d) of Danish Application No. PA 200301175, filed Aug. 15, 2003, and which claims the benefit of U.S. Provisional Application No. 60/501,535, filed Sep. 8, 2003, the contents of all of which are hereby incorporated by reference into the subject application.

FIELD OF THE INVENTION

The present invention relates to novel compounds which are NK3 receptor antagonists and as such useful for treatment of diseases where the NK3 receptor is implicated.

BACKGROUND OF THE INVENTION

Three tachykinins, Substance P (SP), neurokinin A (NKA) and neurokinin B (NKB) are widely distributed throughout the peripheral and central nervous systems. The biological effects of these neuropeptides are primary mediated via binding to and subsequent activation of the three neurokinin receptors, NK1, NK2 and NK3. Substance P is considered to be the endogenous ligand for the NK1 receptor and likewise NKA and NKB for the NK2 and NK3 receptors, respectively. However, recent data indicates that there exist cross-reactivity within the tachykinin system, which might be of physiological relevance as both NKA and NKB potently are able to bind and activate the NK1 receptor (for review see Maggi, C A et al: Trends Pharmacol Sci. 1997, 18, p 351-5). The three receptor subtypes belong to the G-protein-coupled receptor super family and have been cloned in various species including mice, rats and humans (Nakanishi S: Annu Rev Neurosci. 1991, 14, p 123-36).

The three tachykinin receptors are expressed both centrally and in the periphery. The NK3 receptor is mainly expressed centrally in regions including cortex, striatum, substantia nigra compacta, ventral tegmental area, hypothalamus, amygdala and hippocampus (Stroessl A J et al: Brain Res. 1990, 534, p 1-7, Koutcherov Y et al: Neuroreport. 2000, 11, p 3127-31). In the periphery, the NK3 receptor is expressed in regions including colon, kidney, lungs and the urinary bladder (Regoli D et al: Trends Pharmacol Sci. 1988 August; 9(8): 290-5, Kamali F: Curr Opin Investig Drugs. 2001 July; 2(7): 950-6). Centrally, the NK3 receptor is expressed on cholinergic (Chen L W et al: Neuroscience. 2001; 103(2):413-22), noradrenergic (references within Oury-Donat F et al: J. Pharmacol Exp Ther. 1995, 274, p 148-54) and dopaminergic neurons (Keegan K D et al: Br. J. Pharmacol. 1992, 105, p 3-5). In agreement with these results, activation of the NK3 receptor has been reported to be implicated in the regulation of various monoamine transmitters, e.g. dopamine and acetylcholine (Marco N et al: Neuropeptides. 1998, 32, p 481-8, Stoessl A J et al: Brain Res. 1990, 517, p 111-6), noradrenaline (Jung M et al: Neuroscience. 1996, 74, p 403-14) and serotonine (Stoessl A J et al: Brain Res. 1990, 517, p 111-6).

The NK3 receptor-mediated regulation of monoamine systems supports that the NK3 receptor is involved in diverse functions including memory, learning, cortical processing and behavioral control (Yip J et al: Br J Pharmacol. 1997, 122, p 715-25, Ding Y Q et al: J Comp Neurol. 1996, 364, p 290-310, Mileusnic D et al: Neurobiol Aging. 1999, 20, p 19-35) and that it is target for various psychological and neurological disorders (Emonds-Alt X et al: Can J Physiol Pharmacol. 2002, 80, p 482-8, Kamali F, Curr Opin Investig Drugs. 2001, 2, p 950-6, Langlois X et al: J Pharmacol Exp Ther. 2001, 299, p 712-7). Indeed, the NK3 receptor has been reported to be implicated in modulation of anxiety (Ribeiro S J et al: Neuropeptides. 1999, 33, p 181-8).

Further, it has been reported that the NK3 receptor antagonist SR142801 has effect against schizophrenia, in particular positive symptoms. SR142801 is described in, e.g., EP 673928. The structure of SR142801 is outlined below (Kamali F: Curr Opin Investig Drugs. 2001, July; 2(7):950-6).

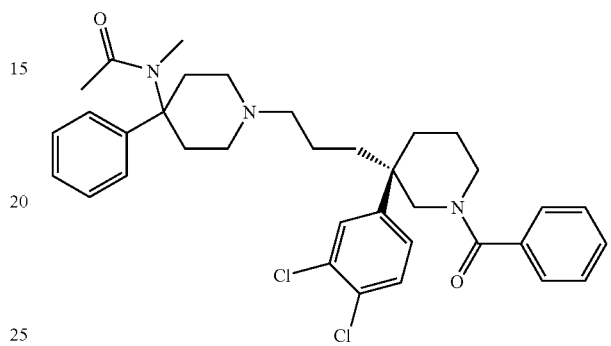

In vivo, NK3 receptor activation centrally has been reported to mediate hypertension and tachycardia (Nagashima A et al: Brain Res. 487, 1989, p 392-396, Takano Y et al: Brain Res. 1990, 528, p 231-7, Picard P et al: Br J Pharmacol. 1994, 112, p 240-9) whereas NK3 receptor activation in the periphery mediates hypotension and bradycardia (Couture R et al: Naunyn Schmiedebergs Arch Pharmacol. 1989, 340, p 547-57). Additional in vivo studies have indicated that NK3 receptor activation decrease water, salt and alcohol intake (Massi M et al: Brain Res Bull. 1991 26 p155-60, Massi M et al: Neurosci Lett. 1988, 92, p 341-6 and Ciccocioppo R et al: Brain Res Bull. 1994, 33, p 71-7) which together with the localization of the NK3 receptor on MCH neurons support a role of the NK3 receptor in the regulation of food intake (Griffond B et al: J Chem Neuroanat. 1997, 12, p 183-9). Further in vivo studies have shown that the NK3 receptor is implicated in renal control of water and electrolyte homeostasis (Yuan Y D: Br J Pharmacol. 1997, 120, p 785-96). Activation of the NK3 receptor has been reported to inhibit gastric acid secretion (Improta G et al: Peptides. 1991, 12, p 1433-4), induce oral dyskinesia (Liminga U et al: Pharmacol Biochem Behav. 1991, 38, p 617-20) and oedema (Inoue H et al: Inflamm Res. 1996, 45, p 316-23).

In vitro NK3 activation has been reported to have proconvulsive effect (Maubach K A et al: Neuroscience. 1998, 83, p 1047-62) and to mediate hyperexcitability in ischemic injury (Stumm R et al: J Neurosci. 2001, 21, p 798-811).

Selective high affinity non-peptide NK3 receptor antagonists have been shown to be antinociceptic (Fioramonti J et al: Neurogastroenterol Motil. 2003, 15, p 363-9, Couture R et al: Life Sci. 2000, 66, p 51-65, Julia V et al: Gastroenterology. 1999, 116, p 1124-31, Coudore-Civiale M A: European Journal of Pharmacology 1998, 361, p 175-184) and analgesic (Houghton A K et al: Neuropharmacology. 2000, 39, p 133-40). In addition, studies demonstrate consistent effect of a NK3 receptor antagonist against visceral pain encouragingly precluding constipation (Mayer E A et al: Gastroenterology. 1999, 116, p1250-2, Julia V et al: Gastroenterology. 1999 116 p124-31). Similarly inhibition of the NK3 receptor is stated to prevent gut inflammation highlighting effect against inflammatory bowel disease (Mazelin L et al: Life Sci. 1998, 63, p 293-304), cough, airway hyperresponsiveness, microvascular hypersensitivity and reduction of bronchoconstriction (Daoui S et al: Am J Respir Crit Care Med. 1998, 158, p 42-8, Rumsey W L et al: J Pharmacol Exp Ther. 2001, 298, p 307-15, Daoui S et al: Pulm Pharmacol Ther. 1997 10 p261-70). Inhibition of the NK3 receptor as therapeutic strategy for Parkinsons disease has been substantiated in several reports (Arenas E: J Neurosci. 1991, 11, p 2332-8, Kernel M L et al: J Neurosci. 2002, 22, p 1929-36).

Accordingly, pre-clinical, in vivo and in vitro studies support that NK3 receptor antagonists are of relevance for the treatment or prevention of various disorders including: schizophrenia, depression, anxiety, Parkinson's disease, pain, convulsions, cough, asthma, airway hyperresponsiveness, microvascular hypersensitivity, bronchoconstriction, gut inflammation, inflammatory bowel disease, hypertension, imbalances in water and electrolyte homeostasis, ischemia, oedema and plasma extravasation.

Hence, there is a desire for NK3 receptor antagonists. The present inventors have now found such compounds with a strong affinity for the NK3 receptor.

Several patent applications relate to compounds disclosed as NK receptor antagonist, e.g. EP 474561, EP 512901 and WO 03/051869. In particular, some patent applications relate to compounds disclosed as NK3 receptor antagonist, e.g. WO 9710211, U.S. Pat. No. 5,434,158 and EP 673928. U.S. Pat. No. 5,750,549 disclose cyclopentane derivatives as NK1 receptor antagonist.

The compounds of the present invention are all cyclopropyl derivates. As described in the following, some patent applications relate to different cyclopropane derivatives. However, none of these patent applications relates to the NK3 receptor or others of the NK receptors.

JP 03056415 describes cyclopropane derivatives of the following formula

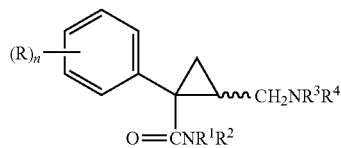

for treatment of cerebral ischemia.

EP 68999 describes cyclopropane derivatives of the following formula

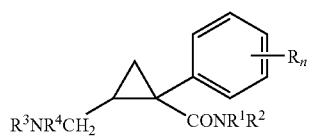

for treatment of depression.

SUMMARY OF THE INVENTION

The objective of the present invention is to provide compounds that are antagonists at the NK3 receptor. Some of the compounds may also have affinity for the NK1 and/or NK2 receptor.

Accordingly, in one aspect the present invention relates to a compound having the general formula I:

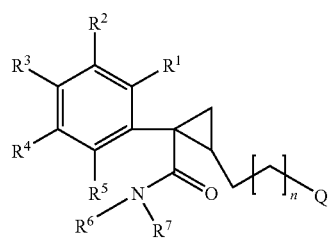

wherein the substituents are as defined herein, or a salt thereof, in particular a pharmaceutically acceptable acid addition salt thereof. The invention in particular provides the (1S,2R)-isomer of such compounds.

Moreover, the invention provides a pharmaceutical composition comprising a compound of formula I as defined herein or a pharmaceutically acceptable salt thereof. Accordingly, the invention provides a compound of formula I as defined herein or a pharmaceutically acceptable salt thereof for use in medicine.

The invention also provides the use of a compound of formula I as defined herein or a pharmaceutically acceptable salt thereof for the preparation of a medicament for the treatment of diseases selected from the group consisting of: schizophrenia, psychotic disorders, depression, anxiety, Parkinson's disease, pain, convulsions, cough, asthma, airway hyperresponsiveness, microvascular hypersensitivity, bronchoconstriction, gut inflammation, inflammatory bowel disease, hypertension, imbalances in water and electrolyte homeostasis, ischemia, oedema and plasma extravasation.

Further, the invention also provides a method for the treatment of diseases selected from the group consisting of: schizophrenia, psychotic disorders, depression, anxiety, Parkinson's disease, pain, convulsions, cough, asthma, airway hyperresponsiveness, microvascular hypersensitivity, bronchoconstriction, gut inflammation, inflammatory bowel disease, hypertension, imbalances in water and electrolyte homeostasis, ischemia, oedema and plasma extravasation, comprising administering a therapeutically effective amount of a compound of formula I as defined herein or a pharmaceutically acceptable salt thereof.

DETAILED DESCRIPTION OF THE INVENTION

Definitions

The term "halogen" means fluoro, chloro, bromo or iodo.

The expression "$C_{1-6}$-alk(en/yn)yl" means a $C_{1-6}$-alkyl, a $C_{2-6}$-alkenyl or a $C_{2-6}$-alkynyl group.

The term "$C_{1-6}$ alkyl" refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

The term "$C_{2-6}$ alkenyl" designates such groups having from two to six carbon atoms, including one double bond, including but not limited to ethenyl, propenyl, and butenyl.

The term "$C_{2-6}$ alkynyl" designates such groups having from two to six carbon atoms, including one triple bond, including but not limited to ethynyl, propynyl and butynyl.

The expression "$C_{3-8}$-cycloalk(en)yl" means a $C_{3-8}$-cycloalkyl or a $C_{3-8}$-cycloalkenyl group.

The term "$C_{3-8}$-cycloalkyl" designates a monocyclic or bicyclic carbocycle having three to eight C-atoms, including but not limited to cyclopropyl, cyclopentyl, cyclohexyl, etc.

The term "$C_{3-8}$-cycloalkenyl" designates a monocyclic or bicyclic carbocycle having three to eight C-atoms and one double bond, including but not limited to cyclopropenyl, cyclopentenyl, cyclohexenyl, etc.

In the expression "$C_{3-8}$-cycloalk(en)yl-$C_{1-6}$-alk(en/yn)yl", the terms "$C_{3-8}$-cycloalk(en)yl" and "$C_{1-6}$-alk(en/yn)yl" are as defined above.

The term "$C_{1-6}$-alk(en/yn)yloxy" refers to groups of the formula $C_{1-6}$-alk(en/yn)yl-O—, wherein $C_{1-6}$-alk(en/yn)yl is as defined above.

The terms "$C_{1-6}$-alk(en/yn)yl-carbonyl", "$C_{1-6}$-alk(en/yn)yl-aminocarbonyl" and "di-($C_{1-6}$-alkyl)aminocarbonyl" refer to groups of formula $C_{1-6}$-alk(en/yn)yl-CO—, $C_{1-6}$-alk(en/yn)yl-NH—CO— and ($C_{1-6}$-alk(en/yn)yl)$_2$—N—CO—, respectively, wherein $C_{1-6}$-alk(en/yn)yl is as defined above.

In the expressions "$C_{1-6}$-alk(en/yn)yl-amino", "di-($C_{1-6}$-alkyl)amino", "$C_{1-6}$-alk(en/yn)ylthio", "halo-$C_{1-6}$-alk(en/yn)yl", "halo-$C_{1-6}$-alk(en/yn)yl-sulfonyl", "halo-$C_{1-6}$-alk(en/yn)yl-sulfanyl", "$C_{1-6}$-alk(en/yn)ylsulfonyl", and "$C_{1-6}$-alk(en/yn)ylsulfanyl" etc., the terms "$C_{1-6}$-alk(en/yn)yl" and "halo" are as defined above.

As used herein, the term "acyl" refers to formyl, $C_{1-6}$-alk(en/yn)ylcarbonyl, arylcarbonyl, aryl-$C_{1-6}$-alk(en/yn)ylcarbonyl, $C_{3-8}$-cycloalk(en)ylcarbonyl or a $C_{3-8}$-cycloalk(en)yl-$C_{1-6}$-alk(en/yn)yl-carbonyl group, wherein $C_{1-6}$-alk(en/yn) and $C_{3-8}$-cycloalk(en)yl are as defined above and aryl is as defined below.

The term "thioacyl" is the corresponding acyl group, in which the carbonyl group is replaced with a thiocarbonyl group.

The term "aryl" refers to a carbocyclic aromatic group, such as phenyl or naphthyl, in particular phenyl and includes both substituted or unsubstituted carbocyclic aromatic groups. Thus, the aryl is optionally substituted with one or more substituents selected from the substituent list as defined below. Accordingly, the term aryl as used herein means an optionally substituted carbocyclic aromatic group, e.g. phenyl or naphthyl, such that said aromatic group is substituted with one or more substituents selected from the substituent list defined below, e.g., $C_{1-6}$-alkyl or halogen. The aryl is preferably mono- or bicyclic.

The term "heteroaryl" refers to an aromatic group containing at least one carbon atom and one or more heteroatoms selected from O, S or N. As used herein the term "heteroaryl" refers to a mono- or bicyclic heterocyclic group including but not limited to indolyl, thienyl, pyrimidyl, oxazolyl, isoxazolyl, thiazolyl, isothiazolyl, imidazolyl, benzofuranyl, benzothienyl, pyridyl and furanyl, in particular pyrimidyl, indolyl, and thienyl. The term heteroaryl as used herein includes both substituted or unsubstituted heteroaryl. Thus, the heteroaryl is optionally substituted with one or more substituents selected from the substituent list as defined below, e.g., $C_{1-6}$-alkyl or halogen.

The term "monocyclic heteroaryl" as used herein refers to 5- to 6-membered aromatic systems containing 1 to 5 carbon atoms and one or more heteroatoms selected from O, S or N.

Accordingly, the term "heteroaryl" refers to 5-membered monocyclic rings such as, but not limited to, 1H-tetrazolyl, 3H-1,2,3-oxathiazolyl, 3H-1,2,4-oxathiazolyl, 3H-1,2,5-oxathiazolyl, 1,3,2-oxathiazolyl, 1,3,4-oxathiazolyl, 1,4,2-oxathiazolyl, 3H-1,2,4-dioxazolyl, 1,3,2-dioxazolyl, 1,4,2-dioxazolyl, 3H-1,2,3-dithiazolyl, 3H-1,2,4-dithiazolyl, 1,3,2-dithiazolyl, 1,4,2-dithiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1H-1,2,3-triazolyl, 1H-1,2,4-triazolyl, isoxazolyl, oxazolyl, isothiazolyl, thiazolyl, 1H-imidazolyl, 1H-pyrazolyl, 1H-pyrrolyl, furanyl, thienyl, 1H-pentazole.

Further, the term "heteroaryl" refers to 6-membered monocyclic rings such as, but not limited to, 1,2,3-oxathiazinyl, 1,2,4-oxathiazinyl, 1,2,5-oxathiazinyl, 4H-1,3,5-oxathiazinyl, 1,4,2-oxathiazinyl, 1,4,3-oxathiazinyl, 1,2,3-dioxazinyl, 1,2,4-dioxazinyl, 4H-1,3,2-dioxazinyl, 4H-1,3,5-dioxazinyl, 1,4,2-dioxazinyl, 2H-1,5,2-dioxazinyl, 1,2,3-dithiazinyl, 1,2,4-dithiazinyl, 4H-1,3,2-dithiazinyl, 4H-1,3,5-dithiazinyl, 1,4,2-dithiazinyl, 2H-1,5,2-dithiazinyl, 2H-1,2,3-oxadiazinyl, 2H-1,2,4-oxadiazinyl, 2H-1,2,5-oxadiazinyl, 2H-1,2,6-oxadiazinyl, 2H-1,3,4-oxadiazinyl, 2H-1,3,5-oxadiazinyl, 2H-1,2,3-thiadiazinyl, 2H-1,2,4-thiadiazinyl, 2H-1,2,5-thiadiazinyl, 2H-1,2,6-thiadiazinyl, 2H-1,3,4-thiadiazinyl, 2H-1,3,5-thiadiazinyl, 1,2,3-triazinyl, 1,2,4-triazinyl, 1,3,5-triazinyl, 2H-1,2-oxazinyl, 2H-1,3-oxazinyl, 2H-1,4-oxazinyl, 2H-1,2-thiazinyl, 2H-1,3-thiazinyl, 2H-1,4-thiazinyl, pyrazinyl, pyridazinyl, pyrimidyl, pyridyl, 2H-pyranyl, 2H-thiinyl.

Finally the term "heteroaryl" also refers to bicyclic rings such as, but not limited to, 3H-1,2,3-benzoxathiazolyl, 1,3,2-benzodioxazolyl, 3H-1,2,3-benzodithiazolyl, 1,3,2-benzodithiazolyl, benzfurazanyl, 1,2,3-benzoxadiazolyl, 1,2,3-benzothiadiazolyl, 2,1,3-benzothiadiazolyl, 1H-benzotriazolyl, 1,2-benzisoxazolyl, 2,1-benzisoxazolyl, benzoxazolyl, 1,2-benzisothiazolyl, 2,1-benzisothiazolyl, benzothiazolyl, 1H-benzimidazolyl, 1H-indazolyl, 3H-1,2-benzoxathiolyl, 1,3-benzoxathiolyl, 3H-2,1-benzoxathiolyl, 3H-1,2-benzodioxolyl, 1,3-benzodioxolyl 3H-1,2-benzodithiolyl, 1,3-benzodithiolyl, 1H-indolyl, 2H-isoindolyl, benzofuranyl, isobenzofuranyl, 1-benzothienyl, 2-benzothienyl, 1H-2,1-benzoxazinyl, 1H-2,3-benzoxazinyl, 2H-1,2-benzoxazinyl, 2H-1,3-benzoxazinyl, 2H-1,4-benzoxazinyl, 2H-3,1-benzoxazinyl, 1H-2,1-benzothiazinyl, 1H-2,3-benzothiazinyl, 2H-1,2-benzothiazinyl, 2H-1,3-benzothiazinyl, 2H-1,4-benzothiazinyl, 2H-3,1-benzothiazinyl, cinnolinyl, phtalazinyl, quinazolinyl, quinoxalinyl, isoquinolyl, quinolyl, 1H-2-benzopyranyl, 2H-1-benzopyranyl, 1H-2-benzothiopyranyl or 2H-1-benzothiopyranyl.

The expression "substituent list" means substituents selected from the group consisting of: halogen, cyano, nitro, $C_{1-6}$-alkyl (e.g methyl), $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, alkylsulphonyl, hydroxy, trifluoromethyl, trifluoromethylsulfonyl, $C_{1-6}$-alkylcarbonylamino and $C_{1-6}$-alkylcarbonyl$C_{1-6}$-alkylamino".

The term "treatment" as used herein in connection with a disease or disorders includes also prevention as the case may be.

Compounds of the Invention and Salts Thereof

The present invention relates to compounds of formula I which are antagonists at the NK3 receptor. These products may therefore be useful in the treatment of certain diseases such as, e.g., schizophrenia, psychotic disorders, depression, anxiety, or Parkinson's disease.

In one aspect, the invention relates to compounds of formula I,

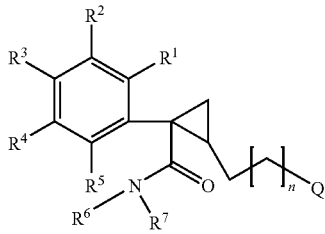
(I)

or a salt thereof, such as a pharmaceutically acceptable salt;

wherein $R^1$-$R^5$ are independently selected from hydrogen, halogen, cyano, nitro, $C_{1-6}$-alk(en/yn)yl (e.g $C_{1-6}$-alkyl, $C_{2-6}$-alkenyl, or $C_{2-6}$-alkynyl; such as methyl), $C_{3-8}$-cycloalk(en)yl (e.g. $C_{3-8}$-cycloalkyl), $C_{3-8}$-cycloalk(en)yl-$C_{1-6}$-alk(en/yn)yl (e.g. $C_{3-8}$-cycloalkyl-$C_{1-6}$-alkyl), amino, $C_{1-6}$-alk(en/yn)ylamino (e.g. $C_{1-6}$-alkylamino), di-($C_{1-6}$- alk(en/yn)yl)amino (.e.g. di-($C_{1-6}$-alkyl)amino), $C_{1-6}$-alk(en/yn)ylcarbonyl (e.g $C_{1-6}$-alkylcarbonyl), aminocarbonyl, $C_{1-6}$-alk(en/yn)ylaminocarbonyl (e.g. $C_{1-6}$-alkylaminocarbonyl), di-($C_{1-6}$-alk(en)yl)aminocarbonyl (e.g. di-($C_{1-6}$-alkyl)aminocarbonyl)), hydroxy, $C_{1-6}$-alk(en/yn)yloxy (e.g. $C_{1-6}$-alkoxy; such as methoxy), $C_{1-6}$-alk(en/yn)ylthio (e.g. $C_{1-6}$-alkylthio, such as methylthio), halo-$C_{1-6}$-alk(en/yn)yl (e.g, halo-$C_{1-6}$-alkyl, such as trifluoromethyl), halo-$C_{1-6}$-alk(en/yn)ylsulfonyl (e.g trifluoromethylsulfonyl), halo-$C_{1-6}$-alk(en/yn)ylsulfanyl (.e.g trifluoromethylsulfanyl)), and $C_{1-6}$-alk(en/yn)ylsulfonyl (e.g. $C_{1-6}$-alkylsulfonyl);

$R^6$ is selected from hydrogen, halo-$C_{1-6}$-alk(en/yn)yl (e.g. trifluoromethyl), $C_{1-6}$-alk(en/yn)yl (e.g. $C_{1-6}$-alkyl, such as methyl, $C_{2-6}$-alkenyl, or $C_{2-6}$-alkynyl), $C_{3-8}$-cycloalk(en)yl (e.g. $C_{3-8}$-cycloalkyl), and $C_{3-8}$-cycloalk(en)yl-$C_{1-6}$-alk(en/yn)yl (e.g. $C_{3-8}$-cycloalkyl-$C_{1-6}$-alkyl);

$R^7$ is an aryl or a heteroaryl; or $R^7$ is a group aryl-$CR^8R^9$—, wherein $R^8$ and $R^9$ are independently selected from hydrogen, $C_{1-6}$-alk(en/yn)yl (e.g. $C_{1-6}$-alkyl, $C_{2-6}$-alkenyl, or $C_{2-6}$-alkynyl; such as methyl), $C_{3-8}$-cycloalk(en)yl (e.g. $C_{3-8}$-cycloalkyl), and $C_{3-8}$-cycloalk(en)yl-$C_{1-6}$-alk(en/yn)yl (e.g. $C_{3-8}$-cycloalkyl-$C_{1-6}$-alkyl);

n is 0, 1, or 2;

Q is selected from (i)-(vii), the arrow indicating the attachment point:

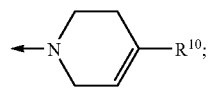
(i)

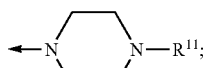
(ii)

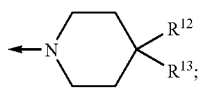
(iii)

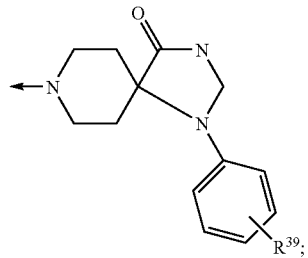
(iv)

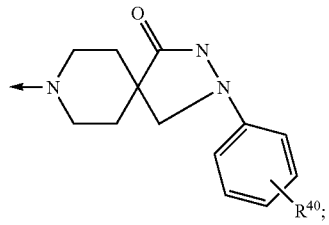
(v)

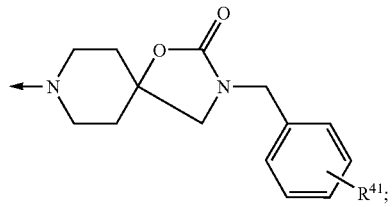
(vi)

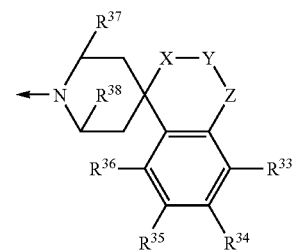
(vii)

wherein $R^{10}$ is an optionally substituted aryl;

wherein $R^{11}$ is selected from an optionally substituted aryl or optionally substituted benzyl, halo-$C_{1-6}$-alk(en/yn)ylsulfonyl (e.g. trifluoromethylsulfonyl), $C_{1-6}$-alk(en/yn)ylsulfonyl (e.g. $C_{1-6}$-alkylsulfonyl), arylsulphonyl, arylacyl, $C_{1-6}$-alk(en/yn)ylcarbonyl (e.g. $C_{1-6}$-alkylcarbonyl), aminocarbonyl, $C_{1-6}$-alk(en/yn)ylaminocarbonyl (e.g. $C_{1-6}$-alkylaminocarbonyl), and di-($C_{1-6}$-alk(en)yl)aminocarbonyl (e.g. di-($C_{1-6}$-alkyl)aminocarbonyl);

wherein $R^{12}$ is an optionally substituted aryl;

wherein $R^{13}$ is hydrogen, hydroxy, cyano, or amino, or one of the following groups:

—NHC$_{1-6}$-alk(en/yn)yl (e.g. —NHC$_{1-6}$-alkyl, —NHC$_{2-6}$-alkenyl, or —NHC$_{2-6}$-alkynyl; such as methyl);

—N($C_{1-6}$-alk(en/yn)yl)$_2$ (e.g —N($C_{1-6}$-alkyl)$_2$);

—NR$^{14}$COR$^{15}$, wherein $R^{14}$ is hydrogen or $C_{1-6}$(en/yn)yl and $R^{15}$ is $C_{1-6}$ alk(en/yn)yl or $C_{3-8}$-cycloalk(en)yl;

—NR$^{16}$COCONR$^{17}$R$^{18}$, wherein $R^{16}$ is hydrogen or $C_{1-6}$-alk(en/yn)yl and $R^{17}$ and $R^{18}$ are selected independently from hydrogen and $C_{1-6}$-alk(en/yn)yl (e.g. $C_{1-6}$-alkyl) or $C_{3-8}$-cycloalkyl; or $R^{17}$ and $R^{18}$ together with the nitrogen to which they are attached form a piperidinyl, piperazinyl or morpholinyl, wherein said piperidinyl, piperazinyl and morpholinyl are optionally substituted (i.e. unsubstituted or substituted) with a $C_{1-6}$-alk(en/yn)yl.

—$NR^{19}CONR^{20}R^{21}$, wherein $R^{19}$ is hydrogen or $C_{1-6}$-alk(en/yn)yl and $R^{20}$ and $R^{21}$ are selected independently from hydrogen and $C_{1-6}$-alk(en/yn)yl or $C_{3-8}$-cycloalkyl; or $R^{20}$ and $R^{21}$ together with the nitrogen to which they are attached form a piperidinyl, piperazinyl or morpholinyl, wherein said piperidinyl, piperazinyl and morpholinyl are optionally substituted (i.e. unsubstituted or substituted) with a $C_{1-6}$-alk(en/yn)yl;

—$NR^{22}SO_2R^{23}$, wherein $R^{22}$ is hydrogen or $C_{1-6}$-alk(en/yn)yl or $C_{3-8}$-cycloalkyl and $R^{23}$ is amino, $C_{1-6}$-alk(en/yn)yl or $C_{3-8}$-cycloalkyl;

—$COR^{24}$, wherein $R^{24}$ is $C_{1-6}$-alk(en/yn)yl or $C_{3-8}$-cycloalkyl;

—$CONR^{25}R^{26}$, wherein $R^{25}$ and $R^{26}$ independently are selected from hydrogen, $C_{1-6}$-alk(en/yn)yl and $C_{3-8}$-cycloalkyl, or $R^{25}$ and $R^{26}$ together with the nitrogen to which they are attached form a piperidinyl, piperazinyl or morpholinyl, wherein said piperidinyl, piperazinyl and morpholinyl are optionally substituted (i.e. unsubstituted or substituted) with a $C_{1-6}$-alk(en/yn)yl, in particular $C_{1-6}$-alkyl;

—$NHCOOR^{42}$, wherein $R^{42}$ is $C_{1-6}$-alk(en/yn)yl or $C_{3-8}$-cycloalk(en)yl;

wherein X, Y, and Z are selected independently from a bond; O; $NR^{27}$; $CR^{28}R^{29}$ and $S(O)_m$, wherein m is 0, 1 or 2;

wherein $R^{27}$ is selected from hydrogen, $C_{1-6}$-alk(en/yn)yl (such as $C_{1-6}$-alkyl, $C_{2-6}$-alkenyl, or $C_{2-6}$-alkynyl), $C_{3-8}$-cycloalkyl, $C_{3-8}$-cycloalkyl-$C_{1-6}$-alkyl, trifluoromethyl, acyl, thioacyl and trifluoromethylsulfonyl; or $R^{27}$ is a group $R^{30}SO_2$—, $R^{30}OCO$— or $R^{30}SCO$—, wherein $R^{30}$ is $C_{1-6}$-alk(en/yn)yl (such as $C_{1-6}$-alkyl, $C_{2-6}$-alkenyl, or $C_{2-6}$-alkynyl), $C_{3-8}$-cycloalkyl, or $C_{3-8}$-cycloalkyl-$C_{1-6}$-alkyl; or $R^{27}$ is a group $R^{31}R^{32}NCO$— or $R^{31}R^{32}NCS$—, wherein $R^{31}$ and $R^{32}$ are independently selected from hydrogen, $C_{1-6}$-alk(en/yn)yl (such as $C_{1-6}$-alkyl, $C_{2-6}$-alkenyl, or $C_{2-6}$-alkynyl), $C_{3-8}$-cycloalkyl, $C_{3-8}$-cycloalkyl-$C_{1-6}$-alkyl and aryl, wherein said aryl is optionally substituted (i.e. unsubstituted or substituted), e.g. with one or more substituents selected from $C_{1-6}$-alkyl or halogen; or wherein $R^{31}$ and $R^{32}$ together with the N-atom to which they are linked, form a pyrrolidinyl, piperidinyl or perhydroazepinyl group;

wherein $R^{28}$ and $R^{29}$ are independently selected from hydrogen, halo such as fluoro, $C_{1-6}$-alk(en/yn)yl (such as $C_{1-6}$-alkyl, $C_{1-6}$-alkyl, $C_{2-6}$-alkenyl, or $C_{2-6}$-alkynyl), $C_{3-8}$-cycloalkyl, and $C_{3-8}$-cycloalkyl-$C_{1-6}$-alkyl;

wherein $R^{33}$-$R^{36}$ are independently selected from hydrogen, halogen, cyano, nitro, $C_{1-6}$-alk(en/yn)yl (such as $C_{1-6}$-alkyl, $C_{2-6}$-alkenyl, or $C_{2-6}$-alkynyl), $C_{3-8}$-cycloalkyl, $C_{3-8}$-cycloalkyl-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, halo-$C_{1-6}$-alk(en/yn)yl, preferably trifluoromethyl, trifluoromethylsulfonyl and $C_{1-6}$-alkylsulfonyl;

wherein $R^{37}$-$R^{38}$ are either both hydrogen or are fused together in an ethylene chain $CH^2$—$CH^2$-forming an aza-bicyclo[3.2.1]octane-yl;

wherein $R^{39}$-$R^{41}$ are independently selected from hydrogen and the substituent list as defined herein;

provided that no more than one of X, Y and Z may be a bond, and provided that two adjacent groups X, Y or Z may not at the same time be selected from O and S.

To further illustrate the invention, without limitation, the following embodiments of $R^1$-$R^5$ are within the scope of the invention, in particular for the compounds or salt thereof: $R^1$-$R^5$ are independently selected from hydrogen, halogen, cyano, $C_{1-6}$-alkyl, $C_{3-8}$-cycloalkyl, $C_{3-8}$-cycloalkyl-$C_{1-6}$-alkyl, $C_{1-6}$-alkyloxy, $C_{1-6}$-alkylthio, and trifluoromethyl; $R^1$-$R^5$ are independently selected from a hydrogen and $C_{1-6}$-alkyl; $R^1$-$R^5$ are independently selected from hydrogen, Cl, F, cyano, methyl, methoxy, methylthio, and trifluoromethyl; $R^1$-$R^5$ are hydrogen; $R^1$-$R^5$ are independently selected from hydrogen and halogen; $R^1$-$R^5$ are independently selected from hydrogen, chloro and fluoro; $R^1$-$R^5$ are independently selected from hydrogen and chloro; $R^1$-$R^5$ are independently selected from hydrogen and fluoro; $R^2$ is chloro and $R^3$ is hydrogen, $R^2$ and $R^3$ are chloro, $R^2$ is fluoro and $R^3$ is hydrogen, or $R^2$ and $R^3$ is fluoro, where the rest of $R^1$-$R^5$ may, e.g., be hydrogen or they may also be substituted from the list above; at least one $R^1$-$R^5$ is F or Cl, such as a compound of the invention for which $R^3$ is F or Cl; $R^1$-$R^5$ is selected independently from H and cyano; $R^1$-$R^5$ are selected independently from H and $C_{1-6}$-alk(en/yn)yl; $R^1$-$R^5$ are selected independently from H and $C_{1-6}$-alkyl, such as methyl or ethyl; $R^1$-$R^5$ are selected independently from H and $C_{1-6}$-alk(en/yn)yloxy, preferably $C_{1-6}$-alkoxy, such as methoxy; $R^1$-$R^5$ are selected independently from H and $C_{1-6}$-alkylthio, such as methylthio; $R^1$-$R^5$ are selected independently from H and trifluoromethyl; at least 3 of $R^1$-$R^5$ are hydrogen, such as 3, 4 or all of $R^1$-$R^5$ are hydrogen; 1 of $R^1$-$R^5$ is substituted, such as in the positions $R^2$ or $R^3$, e.g. with a halogen (e.g. F or Cl), $C_{1-6}$-alkyl (e.g. methyl), $C_{1-6}$-alkoxy (e.g. methoxy) while the rest of $R^1$-$R^5$ being hydrogen; 2 of $R^1$-$R^5$ sre substituted, e.g. in the positions $R^2$ and $R^3$, e.g. selected independently from the group consisting of a halogen (e.g. F or Cl), $C_{1-6}$-alkyl (e.g. methyl), $C_{1-6}$-alkoxy (e.g. methoxy) while the rest of $R^1$-$R^5$ being hydrogen.

To further illustrate the invention, without limitation, the following embodiments of $R^6$ are within the scope of the invention, in particular for the compounds or salt thereof: $R^6$ is selected from hydrogen, halo-$C_{1-6}$-alkyl, $C_{1-6}$-alkyl, $C_{3-8}$-cycloalkyl, and $C_{3-8}$-cycloalkyl-$C_{1-6}$-alkyl; $R^6$ is selected from hydrogen and $C_{1-6}$-alk(en/yn)yl; $R^6$ is hydrogen; $R^6$ is a $C_{1-6}$-alkyl; $R^6$ is methyl; $R^6$ is ethyl.

When $R^7$ is aryl or heteroaryl, it is understood that the aryl and heteroaryl are as defined herein and may be selected among these.

The invention in one aspect, relates to compounds of Formula (I) wherein $R^7$ is an aryl as defined herein. To further illustrate the invention, without limitation, the following embodiments of $R^7$, for which $R^7$ is an aryl, are within the scope of the invention, in particular for the compounds or salt thereof: $R^7$ is an unsubstituted phenyl; $R^7$ is phenyl substituted with one or more substituents, e.g. mono or disubstituted, selected independently from the substituent list as defined herein, including, e.g., halogen and $C_{1-6}$-alkyl; $R^7$ is an unsubstituted phenyl and $R^6$ is hydrogen; $R^7$ is an unsubstituted phenyl and $R^6$ is methyl.

To further illustrate the invention, without limitation, the following embodiments of $R^7$, for which $R^7$ is a group aryl-$CR^8R^9$—, are within the scope of the invention, in particular for the compounds or salt thereof: $R^8$ and $R^9$ are independently selected from hydrogen, $C_{1-6}$-alkyl, $C_{3-8}$-cycloalkyl and $C_{3-8}$-cycloalkyl-$C_{1-6}$-alkyl; $R^8$ and $R^9$ are independently selected from hydrogen and $C_{1-6}$-alkyl; $R^8$ and $R^9$ are independently selected from hydrogen and methyl; $R^8$ and $R^9$ are hydrogen; $R^8$ is hydrogen and $R^9$ is methyl; $R^8$ and $R^9$ are methyl.

It is understood that for $R^7$ being "aryl-$CR^8R^9$", the aryl of aryl-$CR^8R^9$— is as defined herein, i.e. it may, e.g., have one or more of the following characteristic: the aryl is monocyclic or bicyclic; the aryl is unsubstituted; the aryl is phenyl; the aryl is naphthalene, the aryl is substituted with one or more substituents, preferably selected from the group consisting of halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkylcarbonylamino, $C_{1-6}$-alkylcarbonyl $C_{1-6}$-alkylamino, $C_{1-6}$-alkoxy (e.g. methoxy), $C_{1-6}$-alkylthio, hydroxy, trifluoromethyl, difluoromethyl, fluoromethyl and trifluoromethylsulfonyl; the aryl, e.g. phenyl, is an optionally substituted phenyl; the aryl, e.g. phenyl, is mono- or poly-substituted, e.g. di-substituted, e.g. with a halogen, such as fluoro or chloro, and/or e.g. with a $C_{1-6}$-alkoxy (e.g. methoxy).

In a preferred embodiment, $R^7$ is an aryl-$CR^8R^9$— selected from benzyl or substituted benzyl, e.g. halogen substituted benzyl, e.g. 4-halo benzyl, such as 4-fluorobenzyl, or 2-halobenzyl, such as 2-chloro-benzyl, or 3,4-dichloro-benzylamide, 3,4-dimethoxy-benzylamide methyl-1-phenyl-ethyl, methyl-1-(4-methoxyphenyl)-ethyl, or naphthalen-1-ylmethyl.

Further embodiments of the invention relates to compounds of formula I wherein $R^6$ is hydrogen or methyl.

Further aspects of the invention relate to compounds of formula I wherein Q is (i). One aspect of the invention relates to embodiments of the invention where Q is (i) and the aryl of $R^{10}$ is selected from the aryls as defined herein.

In further embodiments, the invention relates to a compound or salt of the invention wherein Q is (ii). Preferably $R^{11}$ is selected from an optionally substituted (i.e. substituted or not) aryl or optionally substituted (i.e. substituted or not) benzyl, trifluoromethylsulfonyl, $C_{1-6}$-alkylsulfonyl, arylsulphonyl, arylacyl, $C_{1-6}$-alkylcarbonyl, aminocarbonyl, $C_{1-6}$-alkylaminocarbonyl and di-($C_{1-6}$-alkyl)aminocarbonyl), wherein said aryl is selected from the aryls as defined herein. The benzyl may be substituted with one ore more substituent selected from the substituent list as defined herein.

In further embodiments, the invention relates to a compound or salt of the invention wherein Q is (iii).

To further illustrate the invention, without limitation, the following embodiments of $R^{12}$ are within the scope of the invention, in particular for the compounds or salt thereof: $R^{12}$ is an aryl as defined herein; $R^{12}$ is unsubstituted phenyl; $R^{12}$ is a phenyl substituted with one or more substituents, e.g. mono or di-substituted, preferably selected from the substituent list as defined herein; the aryl, e.g. phenyl, in $R^{12}$ is substituted with one or more, e.g. one or two substituents selected from a halogen and trifluoromehtyl; the aryl, e.g. phenyl, in $R^{12}$ is substituted with at least one chloro or at least one fluoro and at least one trifluoromethyl; the aryl, e.g. phenyl, in $R^{12}$ is substituted with one Cl and one trifluoromehtyl; $R^{12}$ is 4-chloro-3-trifluromethyl-phenyl.

The following embodiments of the compound of the invention for which Q is (iii) are also within the scope of the invention: $R^{12}$ is an aryl substituted with one or more substituents selected from a halogen and aminoacyl and $R^{13}$ is hydrogen; $R^{12}$ is phenyl substituted with one or more substituents, e.g. mono or di-substituted, selected from a halogen and aminoacyl and $R^{13}$ is hydrogen.

In one embodiment when Q is (iii) the group $R^{13}$ is hydroxy. In a preferred embodiment $R^{12}$ is 4-chloro-3-trifluromethyl-phenyl and $R^{13}$ is hydroxy.

In further embodiments of (iii) the $R^{13}$ is —$NR^{14}COR^{15}$, where $R^{14}$ and $R^{15}$ are as defined herein. To further illustrate the invention, without limitation, the following embodiments of $R^{13}$ are within the scope of the invention, in particular for the compounds or salt thereof: $R^{14}$ is hydrogen; $R^{14}$ is methyl; $R^{15}$ is methyl; $R^{14}$ is hydrogen or $C_{1-6}$-alkyl and $R^{15}$ is $C_{1-6}$-alkyl or $C_{3-8}$-cycloalkyl; $R^{14}$ is H or $CH_3$; $R^{15}$ is $CH_3$; $R^{14}$ is hydrogen and $R^{15}$ is methyl; $R^{14}$ and $R^{15}$ are methyl.

In further embodiments of (iii), the $R^{13}$ is —$NR^{16}COCONR^{17}R^{18}$, wherein $R^{16}$, $R^{17}$ and $R^{18}$ is as defined herein. To further illustrate the invention, without limitation, the following embodiments of $R^{13}$ are also within the scope of the invention, in particular for the compounds or salt thereof: $R^{16}$ is hydrogen or $C_{1-6}$-alkyl and wherein $R^{17}$ and $R^{18}$ are selected independently from hydrogen, $C_{1-6}$-alkyl and $C_{3-8}$-cycloalkyl; $R^{16}$ is hydrogen or $C_{1-6}$-alkyl and where $R^{17}$ and $R^{18}$ together with the nitrogen to which they are attached form a piperidinyl, piperazinyl or morpholinyl, where said piperidinyl, piperazinyl and morpholinyl are optionally substituted with a $C_{1-6}$-alkyl, e.g. methyl; $R^{16}$, $R^{17}$ and $R^{18}$ are hydrogen(i.e. oxalamide, —$NHCOCONH_2$); $R^{16}$ is $C_{1-6}$-alkyl, and $R^{17}$ and $R^{18}$ are hydrogen (i.e. N—$C_{1-6}$-alkyl oxalamide); $R^{16}$ and $R^{17}$ are hydrogen and $R_{18}$ is $C_{1-6}$-alkyl (i.e. N'—$C_{1-6}$-alkyl-N-oxalamide); $R^{16}$ and $R^{17}$ are $C_{1-6}$-alkyl and $R^{18}$ is hydrogen (i.e. N'—$C_{1-6}$-alkyl-N—$C_{1-6}$-alkyl oxalamide); $R^{16}$ is hydrogen and $R^{17}$ and $R^{18}$ are $C_{1-6}$-alkyl, e.g. methyl, (i.e. N',N'-di-($C_{1-6}$-alkyl)-N-oxalamide); $R^{16}$ is hydrogen and $R^{17}$ and $R^{18}$ are methyl; $R^{16}$, $R^{17}$ and $R^{17}$ are $C_{1-6}$-alkyl (i.e. N',N'-di-($C_{1-6}$-alkyl)-N—$C_{1-6}$-alkyl oxalamide).

In further embodiments of (iii) the $R^{13}$ is —$NR^{19}CONR^{20}R^{21}$, wherein $R^{19}$, $R^{20}$ and $R^{21}$ are as defined herein. To further illustrate the invention, without limitation, the following embodiments of $R^{13}$ are also within the scope of the invention, in particular for the compounds or salt thereof: $R^{19}$, $R^{20}$ and $R^{21}$ are independently selected from hydrogen, $C_{1-6}$-alkyl and $C_{3-8}$-cycloalkyl; $R^{19}$, $R^{20}$ and $R^{21}$ are independently selected from hydrogen and $C_{1-6}$-alkyl; $R^{19}$, $R_{20}$ and $R_{21}$ are hydrogen; $R^{19}$ is a $C_{1-6}$-alkyl and $R^{20}$ and $R^{21}$ are hydrogen; $R_{19}$ and $R_{20}$ are hydrogen and $R^{21}$ is a $C_{1-6}$-alkyl; $R^{19}$ and $R^{20}$ are independently selected from a $C_{1-6}$-alkyl and $R^{21}$ is H; $R^{19}$ is H, and $R^{20}$ and $R^{21}$ are independently selected from a $C_{1-6}$-alkyl; or $R^{19}$, $R^{20}$ and $R^{21}$ are independently selected from a $C_{1-6}$-alkyl; $R^{19}$ is H and $R^{20}$ and $R^{21}$ are independently selected from the group consisting of hydrogen, Me, Et, Bu, and i-Pr.

In further embodiments of (iii) the $R^{13}$ is —$NR^{22}SO_2R^{23}$, wherein $R^{22}$ and $R^{23}$ are as defined herein. To further illustrate the invention, without limitation, the following embodiments of $R^{13}$ are also within the scope of the invention, in particular for the compounds or salt thereof: $R^{22}$ is hydrogen or a $C_{1-6}$-alkyl or $C_{3-8}$-cycloalkyl and $R^{23}$ is amino, $C_{1-6}$-alkyl or $C_{3-8}$-cycloalkyl; $R^{22}$ is hydrogen and $R^{23}$ is a $C_{1-6}$-alkyl, e.g. methyl (i.e. N—($C_{1-6}$-alkylsulphonamide) or $R^{22}$ and $R^{23}$ are independently selected from a $C_{1-6}$-alkyl, e.g. methyl i.e. N—$C_{1-6}$-alkyl ($C_{1-6}$-alkylsulphonamide); $R^{22}$ is hydrogen; $R^{23}$ is methyl; $R^{22}$ and $R^{23}$ are methyl; $R^{22}$ is hydrogen and $R^{23}$ is methyl.

In further embodiments of (iii) the $R^{13}$ is —$COR^{24}$, wherein $R^{24}$ is as defined herein. The following embodiments of $R^{13}$ are also within the scope of the invention without limitation, in particular for the compounds or salt thereof: $R^{24}$ is a $C_{1-6}$-alkyl; $R^{24}$ is methyl.

In further embodiments of (iii) the $R^{13}$ is —$CONR^{25}R^{26}$, wherein $R^{25}$ and $R^{26}$ are as defined herein. To further illustrate the invention, without limitation, the following embodiments of $R^{13}$ are also within the scope of the invention, in particular for the compounds or salt thereof: $R^{25}$ and $R^{26}$ are independently selected from hydrogen, $C_{1-6}$-alkyl and $C_{3-8}$-cycloalkyl; $R^{25}$ and $R^{26}$ are independently selected from hydrogen and methyl; $R^{25}$ and $R^{26}$ are hydrogen; $R^{25}$ and $R^{26}$ are methyl; $R^{25}$ is methyl and $R^{26}$ is hydrogen; $R^{25}$ and $R^{26}$ together with the nitrogen to which they are attached form a piperidinyl, piperazinyl or morpholinyl, wherein said piperidinyl, piperazinyl and morpholinyl are optionally substituted with a $C_{1-6}$-alkyl, in a preferred embodiment the piperidinyl, piperazinyl and morpholinyl are not substituted; $R^{25}$ and $R^{26}$ together with the nitrogen to which they are attached form a piperidinyl, wherein the piperidinyl is optionally substituted with a $C_{1-6}$-alkyl, however preferably the piperidinyl is unsubstituted.

In further embodiments, the invention relates to a compound or salt of the invention wherein Q is (vii) as described above.

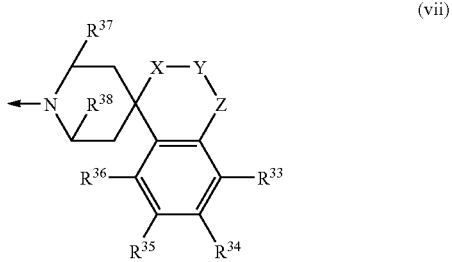

(vii)

To further illustrate the invention, without limitation, the following embodiments of (vii) are within the scope of the invention: Y is a bond and X and Z are selected independently from O, $NR^{27}$, and $CR^{28}R^{29}$ and $S(O)_m$, provided that X and Z may not at the same time be selected from O and S; Y is a bond and X and Z are selected independently from $CR^{28}R^{29}$ and $NR^{27}$; X is $CR^{28}R^{29}$, Y is a bond and Z is $NR^{27}$; X is $CR^{28}R^{29}$, Y is a bond and Z is O; X is O, Y is a bond and Z is $CR^{28}R^{29}$; $R^{28}$ and $R^{29}$ are hydrogen; $R^{27}$ is an acyl, e.g. $C_{1-6}$-alkylcarbonyl; Z is $NR^{27}$ where $R^{27}$ is a $C_{1-6}$-alkylcarbonyl, e.g. —$COCH_3$; X is $CR^{28}R^{29}$ where $R^{28}$ and $R^{29}$ are hydrogen, Y is a bond, and Z is —$NR^{27}$ where said $R^{27}$ is —$COCH_3$; $R^{27}$ is selected from the group $R^{30}SO_2$—, $R^{30}OCO$— and $R^{30}SCO$—; $R^{27}$ is $R^{30}SO_2$; $R^{30}$ is $C_{1-6}$-alkyl, e.g. methyl; X is $CR^{28}R^{29}$, Y is a bond and Z is $NR^{27}$, preferably $R^{28}$ and $R^{29}$ are hydrogen; $R^{27}$ is the group $R^{31}R^{32}NCO$— or $R^{30}R^{31}NCS$—; Y is a bond; $R^{33}$-$R^{36}$ are independently selected from hydrogen and halogen, e.g. chloro or fluoro; $R^{33}$-$R^{36}$ are all hydrogen; $R^{37}$ and $R^{38}$ are both hydrogen; $R^{37}$-$R^{38}$ are fused together in an ethylene chain CH2-CH2-forming an aza-bicyclo[3.2.1]octane-yl as shown in the figure below.

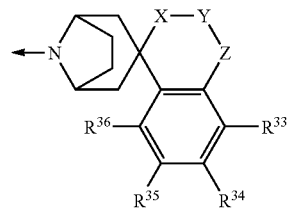

In further embodiments of Compound (I), Q is (iv). To further illustrate the invention, without limitation, the following embodiments of (iv) are within the scope of the invention: $R^{39}$ is selected from the group consisting of hydrogen and halogen; $R^{39}$ is hydrogen in all positions, i.e. the corresponding phenyl group is unsubstituted; the corresponding phenyl group is substituted in only one or two positions with a substituent $R^{39}$ selected from the "substituent" list as defined herein, e.g. a halogen.

In further embodiments of Compound (I), Q is (v). To further illustrate the invention, without limitation, the following embodiments of (v) are within the scope of the invention: $R^{40}$ is selected from the group consisting of hydrogen or halogen; $R^{40}$ is hydrogen in all positions, i.e. the corresponding phenyl group is unsubstituted; the corresponding phenyl group is substituted in only one or two positions with a substituent $R^{40}$ selected from the "substituent list" as defined herein, e.g. a halogen.

In further embodiments of Compound (I), Q is (vi). To further illustrate the invention, without limitation, the following embodiments of (vi) are within the scope of the invention: $R^{41}$ is selected from the group consisting of hydrogen and halogen; $R^{41}$ is hydrogen in all positions, i.e. the corresponding benzyl group is unsubstituted; the corresponding benzyl group is substituted in only one or two positions with a substituent $R^{41}$ selected from the substituent list as defined herein, e.g. with a halogen.

The compounds of the present invention may have one or more asymmetric centers and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention.

The compounds of the general formula I exist as optical isomers thereof and such optical isomers are also embraced by the invention. In particular, the compounds of the invention possessing the absolute stereochemistry (1S,2R) are within the invention, either as enantiomers or as mixtures containing compounds of the invention possessing the absolute stereochemistry (1S,2R).

Accordingly, an important aspect of the invention is a compound or salt of the invention as described herein, wherein the compound of formula I is the (1S,2R)-isomer i.e. the compound with absolute configuration as shown in formula IA.

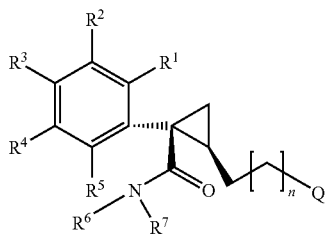

(IA)

The compound of the invention of formula I or the salt thereof may be part of a racemic mixtures comprising the (1S,2R)-isomer, i.e. the compound shown in formula IA or it may be present as the enantiomer, i.e. without the 3 others stereoisomers.

The invention in further embodiment relates to a compound of formula I which compound is the (1R,2R)-isomer.

The invention in further embodiment relates to a compound of formula I which compound is the (1R,2S)-isomer.

The invention in further embodiment relates to a compound of formula I which compound is the (1S,2S)-isomer.

In this context is understood that when specifying the enantiomeric form, then the compound is in a preferred embodiment in enantiomeric excess.

Accordingly, one embodiment of the invention relates to a compound of the invention having an enantiomeric excess of at least 60% (60% enantiomeric excess means that the ratio of Va to its enantiomer is 80:20 in the mixture in question), at least 70%, at least 80%, at least 85%, at least 90%, at least 96%, preferably at least 98%.

The expression "mixture of stereoisomeres comprising the (1S,2R)-isomer of formula 1" implies that in further embodiments, the compound of the invention, i.e. product, may be any one of the following mixture of stereoisomeres: a (1S, 2R)-isomer and a (1R,2R)-isomer of formula 1; a (1S,2R)-isomer and a (1R,2S)-isomer of formula 1; a (1S,2R)-isomer and a (1S,2S)-isomer of formula 1; a (1S,2R)-isomer and a (1R, 2R)-isomer of formula 1, i.e. consisting of 2, 3 or 4 of the corresponding stereoisomers.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

In further embodiments of formula I, the compound of the invention is any one of:

1. 2-(4-Acetylamino-4-phenyl-piperidin-1-ylmethyl)-1-(3,4-dichlorophenyl)-cyclopropanecarboxylic acid benzyl-methyl-amide;
2. 2-[4-(Acetyl-methyl-amino)-4-phenyl-piperidin-1-ylmethyl]-1-(3,4-dichlorophenyl)-cyclopropanecarboxylic acid benzyl-methyl-amide;
3. 2-[1-acetyl-spiro[2,3-dihydro-1H-indol-3-yl-3,4'-piperidine-1'-yl-methyl]-1-(3,4-dichlorophenyl)-cyclopropanecarboxylic acid benzyl-methyl-amide;
4. 2-[1-acetyl-5-fluorospiro[2,3-dihydro-1H-indol-3-yl-3,4'-piperidine-1'-yl-methyl]-1-(3,4-dichlorophenyl)-cyclopropanecarboxylic acid benzyl-methyl-amide;
5. 2-[1-acetyl-spiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl)amide;
6. 2-[1-acetyl-5-fluorospiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl) amide;
7. 1-Phenyl-2-[4-phenyl-4-(piperidine-1-carbonyl)-piperidin-1-ylmethyl]-cyclopropanecarboxylic acid benzyl-methyl-amide;
8. 2-[1-methanesulphonyl-spiro[2,3-dihydro-1H-indol-3-yl-3,4'-piperidine-1'-yl-methyl]-1-phenyl-cyclopropanecarboxylic acid benzyl-methyl-amide;
9. 2-(4-Acetyl-4-phenyl-piperidin-1-ylmethyl)-1-phenyl-cyclopropanecarboxylic acid benzyl-methyl-amide;
10. 2-[4-(4-Chloro-3-trifluoromethyl-phenyl)-4-hydroxy-piperidin-1-ylmethyl]-1-phenyl-cyclopropanecarboxylic acid benzyl-methyl-amide;
11. 2-[1-acetyl-5-fluorospiro[2,3-dihydro-1H-indol-3-yl-3,4'-piperidine-1'-yl-methyl]-1-phenyl-cyclopropanecarboxylic acid benzyl-methyl-amide;
12. 2-(4-Acetylamino-4-phenyl-piperidin-1-ylmethyl)-1-(4-chloro-phenyl)-cyclopropanecarboxylic acid benzyl-methyl-amide;
13. 1-(4-Chloro-phenyl)-2-[4-phenyl-4-(piperidine-1-carbonyl)-piperidin-1-ylmethyl]-cyclopropanecarboxylic acid benzyl-methyl-amide;
14. 2-[4-(Acetyl-methyl-amino)-4-phenyl-piperidin-1-ylmethyl]-1-(4-chloro-phenyl)-cyclopropanecarboxylic acid benzyl-methyl-amide;
15. 2-(4-Acetyl-4-phenyl-piperidin-1-ylmethyl)-1-(4-chloro-phenyl)-cyclopropanecarboxylic acid benzyl-methyl-amide;
16. 2-[1-acetyl-spiro[2,3-dihydro-1H-indol-3-yl-3,4'-piperidine-1'-yl-methyl]-1-(4-chlorophenyl)-cyclopropanecarboxylic acid benzyl-methyl-amide;
17. 2-[1-acetyl-5-fluorospiro[2,3-dihydro-1H-indol-3-yl-3,4'-piperidine-1'-yl-methyl]-1-(4-chlorophenyl)-cyclopropanecarboxylic acid benzyl-methyl-amide;
18. 2-(4-Acetylamino-4-phenyl-piperidin-1-ylmethyl)-1-(3,4-difluoro-phenyl)-cyclopropanecarboxylic acid methyl-(1-phenyl-ethyl)-amide;
19. 2-[4-(Acetyl-methyl-amino)-4-phenyl-piperidin-1-ylmethyl]-1-(3,4-difluoro-phenyl)-cyclopropanecarboxylic acid methyl-([S]-1-phenyl-ethyl)-amide;

20. 2-[1-acetyl-5-fluorospiro[2,3-dihydro-1H-indol-3-yl-3,4'-piperidine-1'-yl-methyl]-1-(3,4-difluorophenyl)-cyclopropanecarboxylic acid methyl-([S]-1-phenyl-ethyl) amide;
21. 2-(4-Acetylamino-4-phenyl-piperidin-1-ylmethyl)-1-phenyl-cyclopropanecarboxylic acid (4-fluoro-benzyl)-methyl-amide;
22. 2-[4-(Acetyl-methyl-amino)-4-phenyl-piperidin-1-ylmethyl]-1-phenyl-cyclopropanecarboxylic acid (4-fluoro-benzyl)-methyl-amide;
23. 2-[1-acetyl-spiro[2,3-dihydro-1H-indol-3-yl-3,4'-piperidine-1'-yl-methyl]-1-phenyl-cyclopropanecarboxylic acid (4-fluoro-benzyl)-methyl-amide;
24. 2-[4-(4-Chloro-3-trifluoromethyl-phenyl)-4-hydroxy-piperidin-1-ylmethyl]-1-phenyl-cyclopropanecarboxylic acid (4-fluoro-benzyl)-methyl-amide;
25. 2-[1-acetyl-5-fluorospiro[2,3-dihydro-1H-indol-3-yl-3,4'-piperidine-1'-yl-methyl]-1-phenyl-cyclopropanecarboxylic acid (4-fluoro-benzyl)-methyl-amide;
26. 2-[4-(Acetyl-methyl-amino)-4-phenyl-piperidin-1-ylmethyl]-1-(4-chloro-phenyl)-cyclopropanecarboxylic acid (4-fluoro-benzyl)-methyl-amide;
27. 2-[1-acetyl-5-fluoro-spiro[2,3-dihydro-1H-indol-3,3'-(8'-aza-bicyclo[3.2.1]octane-8'-yl)]-1-(4-chlorophenyl)-cyclopropanecarboxylic acid (4-fluoro-benzyl)-methyl-amide;
28. 2-(4-Acetyl-4-phenyl-piperidin-1-ylmethyl)-1-(4-chloro-phenyl)-cyclopropanecarboxylic acid (4-fluoro-benzyl)-methyl-amide;
29. 2-[1-acetyl-spiro[2,3-dihydro-1H-indol-3-yl-3,4'-piperidine-1'-yl-methyl]-1-(4-chlorophenyl)-cyclopropanecarboxylic acid (4-fluoro-benzyl)-methyl-amide;
30. 2-[1-acetyl-5-fluorospiro[2,3-dihydro-1H-indol-3-yl-3,4'-piperidine-1'-yl-methyl]-1-(4-chlorophenyl)-cyclopropanecarboxylic acid (4-fluoro-benzyl)-methyl-amide;
31. 1-(4-Fluoro-phenyl)-2-[4-phenyl-4-(piperidine-1-carbonyl)-piperidin-1-ylmethyl]-cyclopropanecarboxylic acid (4-fluoro-benzyl)-methyl-amide;
32. 2-[1-acetyl-5-fluorospiro[2,3-dihydro-1H-indol-3-yl-3,4'-piperidine-1'-yl-methyl]-1-(4-fluorophenyl)-cyclopropanecarboxylic acid (4-fluoro-benzyl)-methyl-amide;
33. 1-(3,4-Difluoro-phenyl)-2-[4-phenyl-4-(piperidine-1-carbonyl)-piperidin-1-ylmethyl]-cyclopropanecarboxylic acid-methyl-amide;
34. 2-[1-acetyl-5-fluoro-spiro[2,3-dihydro-1H-indol-3,3'-(8'-aza-bicyclo[3.2.1]octane-8'-yl)]-1-(3,4-difluorophenyl)-cyclopropanecarboxylic acid (4-fluoro-benzyl)-methyl-amide;
35. 2-[1-acetyl-5-fluorospiro[2,3-dihydro-1H-indol-3-yl-3,4'-piperidine-1'-yl-methyl]-1-(3,4-dichlorophenyl)-cyclopropanecarboxylic acid (4-fluoro-benzyl)-methyl-amide;
36. 1-(3,4-Dichlorophenyl)-2-[4-phenyl-4-(piperidine-1-carbonyl)-piperidin-1-ylmethyl]-cyclopropanecarboxylic acid benzyl-methyl-amide;
37. 2-(4-Acetyl-4-phenyl-piperidin-1-ylmethyl)-1-(3,4-dichlorophenyl)-cyclopropanecarboxylic acid benzyl-methyl-amide;
38. 2-[1-acetyl-5-fluorospiro[2,3-dihydro-1H-indol-3-yl-3,4'-piperidine-1'-yl-methyl]-1-(4-fluorophenyl)-cyclopropanecarboxylic acid methyl-([S]-1-phenyl-ethyl)amide;
39. 2-(4-Acetylamino-4-phenyl-piperidin-1-ylmethyl)-1-(3,4-dichlorophenyl)-cyclopropanecarboxylic acid methyl-(1-phenyl-ethyl)-amide;
40. 1-(3,4-Dichlorophenyl)-2-[4-phenyl-4-(piperidine-1-carbonyl)-piperidin-1-ylmethyl]-cyclopropanecarboxylic acid methyl-([S]-1-phenyl-ethyl)-amide;
41. 2-[4-(Acetyl-methyl-amino)-4-phenyl-piperidin-1-ylmethyl]-1-(3,4-dichlorophenyl)-cyclopropanecarboxylic acid methyl-([S]-1-phenyl-ethyl)-amide;
42. 1-Phenyl-2-[4-phenyl-4-(piperidine-1-carbonyl)-piperidin-1-ylmethyl]-cyclopropanecarboxylic acid (4-fluoro-benzyl)-methyl-amide;
43. 1-(4-Chloro-phenyl)-2-[4-phenyl-4-(piperidine-1-carbonyl)-piperidin-1-ylmethyl]-cyclopropanecarboxylic acid (4-fluoro-benzyl)-methyl-amide;
44. 2-(4-Acetylamino-4-phenyl-piperidin-1-ylmethyl)-1-(4-chloro-phenyl)-cyclopropanecarboxylic acid (4-fluoro-benzyl)-methyl-amide;
45. 2-(4-Acetylamino-4-phenyl-piperidin-1-ylmethyl)-1-(4-chloro-phenyl)-cyclopropanecarboxylic acid (2-chloro-benzyl)-methyl-amide;
46. 1-(4-Chloro-phenyl)-2-[4-phenyl-4-(piperidine-1-carbonyl)-piperidin-1-ylmethyl]-cyclopropanecarboxylic acid (2-chloro-benzyl)-methyl-amide;
47. 2-[4-(Acetyl-methyl-amino)-4-phenyl-piperidin-1-ylmethyl]-1-(4-chloro-phenyl)-cyclopropanecarboxylic acid (2-chloro-benzyl)-methyl-amide;
48. 2-[1-acetyl-5-fluorospiro[2,3-dihydro-1H-indol-3-yl-3,4'-piperidine-1'-yl-methyl]-1-(4-chlorophenyl)-cyclopropanecarboxylic acid (2-chlorobenzyl)-methyl-amide;
49. 2-[4-(Acetyl-methyl-amino)-4-phenyl-piperidin-1-ylmethyl]-1-(4-fluoro-phenyl)-cyclopropanecarboxylic acid (2-chloro-benzyl)-methyl-amide;
50. 2-[4-(Acetyl-methyl-amino)-4-phenyl-piperidin-1-ylmethyl]-1-(3,4-difluoro-phenyl)-cyclopropanecarboxylic acid (2-chloro-benzyl)-methyl-amide;
51. 2-(4-Acetylamino-4-phenyl-piperidin-1-ylmethyl)-1-(3,4-dichlorophenyl)-cyclopropanecarboxylic acid (2-chloro-benzyl)-methyl-amide;
52. 1-(3,4-Dichlorophenyl)-2-[4-phenyl-4-(piperidine-1-carbonyl)-piperidin-1-ylmethyl]-cyclopropanecarboxylic acid (2-chloro-benzyl)-methyl-amide;
53. 2-[4-(Acetyl-methyl-amino)-4-phenyl-piperidin-1-ylmethyl]-1-(3,4-dichlorophenyl)-cyclopropanecarboxylic acid (2-chloro-benzyl)-methyl-amide;
54. 2-[1-acetyl-spiro[2,3-dihydro-1H-indol-3-yl-3,4'-piperidine-1'-yl-methyl]-1-(3,4-dichlorophenyl)-cyclopropanecarboxylic acid (2-chlorobenzyl)-methyl-amide;
55. 1-(3,4-Dichlorophenyl)-2-(4-phenyl-piperidin-1-ylmethyl)-cyclopropanecarboxylic acid benzyl-methyl-amide; and
56. 2-(4-Acetylamino-4-phenyl-piperidin-1-ylmethyl)-1-(3,4-dichlorophenyl)-cyclopropanecarboxylic acid (1-methyl-1-phenyl-ethyl)-amide;
57 2-(4-phenyl-piperidin-1-ylmethyl)-1-(3,4-dichlorophenyl)-cyclopropanecarboxylic acid benzyl-ethyl-amide
58. 2-(4-Acetylamino-4-phenyl-piperidin-1-ylmethyl)-1-(3,4-dichlorophenyl)-cyclopropanecarboxylic acid benzyl-methyl-amide-([R]-1-phenyl-ethyl)amide
59. 2-(4-Acetylamino-4-phenyl-piperidin-1-ylmethyl)-1-(3,4-dichlorophenyl)-cyclopropanecarboxylic acid benzyl-methyl-amide;
60. 2-(4-Acetylamino-4-phenyl-piperidin-1-ylmethyl)-1-(3,4-dichlorophenyl)-cyclopropanecarboxylic acid benzyl-methyl-amide; and
61. 2-(4-Acetylamino-4-phenyl-piperidin-1-ylmethyl)-1-(3,4-dichlorophenyl)-cyclopropanecarboxylic acid benzyl-methyl-amide;
62. 1S,2R)-2-(4-Acetylamino-4-phenyl-piperidin-1-ylmethyl)-1-(3,4-dichlorophenyl)-cyclopropanecarboxylic acid methyl-([R]1-phenyl-ethyl)-amide;

63. 2-[4-(Acetyl-methyl-amino)-4-phenyl-piperidin-1-ylmethyl]-1-(3,4-dichlorophenyl)-cyclopropanecarboxylic acid methyl-([R]-1-phenyl-ethyl)-amide;
64. 2-[1-acetyl-spiro[2,3-dihydro-1H-indol-3-yl-3,4'-piperidine-1'-yl-methyl]-1-(3,4-dichlorophenyl)-cyclopropanecarboxylic acid methyl-([R]-1-phenyl-ethyl)amide;
65. 2-[1-acetyl-5-fluoro-spiro[2,3-dihydro-1H-indol-3-yl-3,4'-piperidine-1'-yl-methyl]-1-(3,4-dichlorophenyl)-cyclopropanecarboxylic acid methyl-([R]-1-phenyl-ethyl) amide;
66. 2-(4-Acetylamino-4-phenyl-piperidin-1-ylmethyl)-1-phenyl-cyclopropanecarboxylic acid benzyl-methyl-amide;
67. 1-(3,4-Dichlorophenyl)-2-[4-phenyl-4-(piperidine-1-carbonyl)-piperidin-1-ylmethyl]-cyclopropanecarboxylic acid methyl-([S]-1-phenyl-ethyl)-amide;
68. 2-[1-acetyl-5-fluoro-spiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl) amide;
69. 1-Phenyl-2-[4-phenyl-4-(piperidine-1-carbonyl)-piperidin-1-ylmethyl]-cyclopropanecarboxylic acid (4-fluoro-benzyl)-methyl-amide;
70. 2-(4-Acetyl-4-phenyl-piperidin-1-ylmethyl)-1-phenyl-cyclopropanecarboxylic acid (4-fluoro-benzyl)-methyl-amide;
71. 2-[1-methanesulphonyl-spiro[2,3-dihydro-1H-indol-3-yl-3,4'-piperidine-1'-yl-methyl]-1-(4-fluophenyl)-cyclopropanecarboxylic acid (4-fluoro-benzyl)-methyl-amide;
72. 2-[4-(Acetyl-methyl-amino)-4-phenyl-piperidin-1-ylmethyl]-1-(4-fluorophenyl)-cyclopropanecarboxylic acid (4-fluoro-benzyl)-methyl-amide;
73. 2-(4-Acetyl-4-phenyl-piperidin-1-ylmethyl)-1-(4-fluorophenyl)-cyclopropanecarboxylic acid (4-fluoro-benzyl)-methyl-amide;
74. 2-[1-acetyl-spiro[2,3-dihydro-1H-indol-3-yl-3,4'-piperidine-1'-yl-methyl]-1-(4-flurophenyl)-cyclopropanecarboxylic acid (4-fluoro-benzyl)-methyl-amide;
75. 2-(4-Acetyl-4-phenyl-piperidin-1-ylmethyl)-1-(3,4-difluorophenyl)-cyclopropanecarboxylic acid (4-fluoro-benzyl)-methyl-amide;
76. 2-[1-acetyl-spiro[2,3-dihydro-1H-indol-3-yl-3,4'-piperidine-1'-yl-methyl]-1-(3,4-diflurophenyl)-cyclopropanecarboxylic acid (4-fluoro-benzyl)-methyl-amide;
77. 1-(4-Fluoro-phenyl)-2-[4-phenyl-4-(piperidine-1-carbonyl)-piperidin-1-ylmethyl]-cyclopropanecarboxylic acid methyl-([S]1-phenyl-ethyl)-amide;
78. 2-(4-Acetyl-4-phenyl-piperidin-1-ylmethyl)-1-(4-chlorophenyl)-cyclopropanecarboxylic acid (2-chloro-benzyl)-methyl-amide;
79. 2-[1-acetyl-spiro[2,3-dihydro-1H-indol-3-yl-3,4'-piperidine-1'-yl-methyl]-1-(4-chlorophenyl)-cyclopropanecarboxylic acid (2-chloro-benzyl)-methyl-amide;
80. 2-(4-Acetylamino-4-phenyl-piperidin-1-ylmethyl)-1-(4-fluorophenyl)-cyclopropanecarboxylic acid (2-chloro-benzyl)-methyl-amide;
81. 1-(4-Fluoro-phenyl)-2-[4-phenyl-4-(piperidine-1-carbonyl)-piperidin-1-ylmethyl]-cyclopropanecarboxylic acid (2-chloro-benzyl)-methyl-amide;
82. 2-(4-Acetylamino-4-phenyl-piperidin-1-ylmethyl)-1-(3,4-difluorophenyl)-cyclopropanecarboxylic acid (2-chloro-benzyl)-methyl-amide;
83. 1-(3,4-Difluorophenyl)-2-[4-phenyl-4-(piperidine-1-carbonyl)-piperidin-1-ylmethyl]-cyclopropanecarboxylic acid (2-chloro-benzyl)-methyl-amide;
84. 2-[1-acetyl-spiro[2,3-dihydro-1H-indol-3-yl-3,4'-piperidine-1'-yl-methyl]-1-(3,4-diflurophenyl)-cyclopropanecarboxylic acid (2-chloro-benzyl)-methyl-amide;
85. 2-[1-acetyl-5-fluoro-spiro[2,3-dihydro-1H-indol-3-yl-3,4'-piperidine-1'-yl-methyl]-1-(3,4-diflurophenyl)-cyclopropanecarboxylic acid (2-chloro-benzyl)-methyl-amide;
86. 1-(3,4-Dichlorophenyl)-2-(4-phenyl-piperidin-1-ylmethyl)-cyclopropanecarboxylic acid 3,4-dichloro-benzylamide;
87. 1-(3,4-Dichlorophenyl)-2-(4-phenyl-piperidin-1-ylmethyl)-cyclopropanecarboxylic acid 3,4-dimethoxy-benzylamide;
88. 2-(4-Acetylamino-4-phenyl-piperidin-1-ylmethyl)-1-(3,4-dichlorophenyl)-cyclopropanecarboxylic acid phenylamide;
89. 2-(4-Acetylamino-4-phenyl-piperidin-1-ylmethyl)-1-(3,4-dichlorophenyl)-cyclopropanecarboxylic acid (1-methyl-1-phenyl-ethyl)-amide;
90. 1-Phenyl-2-[4-(3-trifluoromethylphenyl)-piperazin-1-ylmethyl]-cyclopropanecarboxylic acid benzyl-methyl-amide;
91. 2-(4-Benzyl-piperazin-1-ylmethyl)-1-(4-chlorophenyl)-cyclopropanecarboxylic acid (4-fluoro-benzyl)-methyl-amide;
92. 1-(4-chlorophenyl)-2-[4-(3-trifluoromethylphenyl)-piperazin-1-ylmethyl]-cyclopropanecarboxylic acid 4-fluorobenzyl-methyl-amide;
93. 2-(4-Benzyl-piperazin-1-ylmethyl)-1-(4-chlorophenyl)-cyclopropanecarboxylic acid benzyl-methyl-amide;
94. 2-(4-Benzyl-piperazin-1-ylmethyl)-1-phenyl-cyclopropanecarboxylic acid benzyl-methyl-amide;
95. 1-(4-chlorophenyl)-2-[4-(3-trifluoromethylphenyl)-piperazin-1-ylmethyl]-cyclopropanecarboxylic acid benzyl-methyl-amide;
96. 1-phenyl-2-[4-(3-trifluoromethylphenyl)-piperazin-1-ylmethyl]-cyclopropanecarboxylic acid 4-fluorobenzyl-methyl-amide;
97. 2-(4-Acetylamino-4-phenyl-piperidin-1-ylmethyl)-1-(3,4-dichloro-phenyl)-cyclopropanecarboxylic acid benzyl amide;
98. 2-[1-acetyl-5-fluoro-spiro[2,3-dihydro-1H-indol-3-yl-3,4'-piperidine-1'-yl-methyl]-1-(3,4-diflurophenyl)-cyclopropanecarboxylic acid (2-fluoro-benzyl)-amide;
99. 2-(4-Acetylamino-4-phenyl-piperidin-1-ylmethyl)-1-(3,4-dichlorophenyl)-cyclopropanecarboxylic acid methyl-[1-(4-methoxyphenyl)-ethyl]-amide;
100. 2-(4-Acetylamino-4-phenyl-piperidin-1-ylmethyl)-1-(3,4-dichloro-phenyl)-cyclopropanecarboxylic acid (2-chlorobenzyl)amide;
101. 2-(4-Acetylamino-4-phenyl-piperidin-1-ylmethyl)-1-(3,4-dichloro-phenyl)-cyclopropanecarboxylic acid (3,4-dichlorobenzyl)amide;
102. 2-(4-Acetylamino-4-phenyl-piperidin-1-ylmethyl)-1-(3,4-dichloro-phenyl)-cyclopropanecarboxylic acid methyl-phenyl-amide;
103. 2-(4-Acetylamino-4-phenyl-piperidin-1-ylmethyl)-1-(4-methoxy-phenyl)-cyclopropanecarboxylic acid (4-fluoro-benzyl)-methyl-amide;
104. 2-(4-Acetylamino-4-phenyl-piperidin-1-ylmethyl)-1-p-tolyl-cyclopropanecarboxylic acid (4-fluoro-benzyl)-methyl-amide;
105. 2-(4-Acetylamino-4-phenyl-piperidin-1-ylmethyl)-1-m-tolyl-cyclopropanecarboxylic acid benzyl-methyl-amide;
106. 2-(4-Acetylamino-4-phenyl-piperidin-1-ylmethyl)-1-m-tolyl-cyclopropanecarboxylic acid (4-fluoro-benzyl)-methyl-amide;

107. 2-(4-Acetylamino-4-phenyl-piperidin-1-ylmethyl)-1-(3-methoxy-phenyl)-cyclopropanecarboxylic acid (4-fluoro-benzyl)-methyl-amide;
108. 2-(4-Acetylamino-4-phenyl-piperidin-1-ylmethyl)-1-(4-methoxy-phenyl)-cyclopropanecarboxylic acid benzyl-methyl-amide;
109. 2-(4-Acetylamino-4-phenyl-piperidin-1-ylmethyl)-1-p-tolyl-cyclopropanecarboxylic acid benzyl-methyl-amide;
110. 2-(4-Acetylamino-4-phenyl-piperidin-1-ylmethyl)-1-(3-methoxy-phenyl)-cyclopropanecarboxylic acid benzyl-methyl-amide;
111. 1-Phenyl-2-(4-phenyl-4-ureido-piperidin-1-ylmethyl)-cyclopropanecarboxylic acid (4-fluoro-benzyl)-methyl-amide;
112. 1-(3,4-Dichlorophenyl)-2-(4-phenyl-4-ureido-piperidin-1-ylmethyl)-cyclopropanecarboxylic acid-benzyl-methyl-amide;
113. 1-Phenyl-2-[4-(3-methyl-ureido)-4-phenyl-piperidin-1-ylmethyl]-cyclopropanecarboxylic acid (4-fluorobenzyl)-methyl-amide;
114. 2-[4-(3-Methyl-ureido)-4-phenyl-piperidin-1-ylmethyl]-1-(3,4-dichlorophenyl)-cyclopropanecarboxylic acid benzyl-methyl-amide;
115. N-(1-{2-[((4-Fluoro-benzyl)-methyl-carbamoyl]-2-phenyl-cyclopropylmethyl}-4-phenyl-piperidin-4-yl)-oxalamide;
116. N-(1-{2-[benzyl-methyl-carbamoyl]-2-(3,4-dichlorophenyl)-cyclopropylmethyl}-4-phenyl-piperidin-4-yl)-oxalamide;
117. 1-Phenyl-2-(4-methanesulfonylamino-4-phenyl-piperidin-1-ylmethyl)-cyclopropanecarboxylic acid-(4-fluorobenzyl)-methyl-amide;
118. 2-(4-Methanesulfonylamino-4-phenyl-piperidin-1-ylmethyl)-1-(3,4-dichlorophenyl)-cyclopropanecarboxylic acid-benzyl-methyl-amide;
119. {1-[2-((4-fluoro-benzyl)-methyl-carbamoyl)-2-phenyl-cyclopropylmethyl]-4-phenyl-piperidin-4-yl}-carbamic acid methyl ester;
120. (1-{2-benzyl-methyl-carbamoyl]-2-(3,4-dichlorophenyl)-cyclopropylmethyl}-4-phenyl-piperidin-4-yl)-carbamic acid methyl ester;
121. 1-(3,4-Dichloro-phenyl)-2-[4-(3,3-dimethyl-ureido)-4-phenyl-piperidin-1-ylmethyl]-cyclopropanecarboxylic acid benzyl-methyl-amide;
122. 1-phenyl-2-[4-(3,3-dimethyl-ureido)-4-phenyl-piperidin-1-ylmethyl]-cyclopropanecarboxylic acid (4-fluorobenzyl)-methyl-amide;
123. 2-[2-(4-Acetylamino-4-phenyl-piperidin-1-yl)-ethyl]-1-(3,4-dichlorophenyl)-cyclopropanecarboxylic acid (4-fluoro-benzyl)-methyl-amide;
124. 2-[3-(4-Acetylamino-4-phenyl-piperidin-1-yl)-propyl]-1-(3,4-dichlorophenyl)-cyclopropanecarboxylic acid (4-fluoro-benzyl)-methyl-amide;
125. 2-[4-(2-Acetylamino-5-fluorophenyl)-piperidin-1-ylmethyl]-1-(3,4-dichlorophenyl)-cyclopropanecarboxylic acid (4-fluoro-benzyl)-methyl-amide;
126. 2-(4-Acetylamino-4-phenyl-piperidin-1-ylmethyl)-1-(3,4-dimethylphenyl)-cyclopropanecarboxylic acid (4-fluoro-benzyl)-methyl-amide;
127. 2-(4-Acetylamino-4-phenyl-piperidin-1-ylmethyl)-1-(3,4-dichlorophenyl)-cyclopropanecarboxylic acid (4-fluoro-benzyl)-methyl-amide;
128. 2-(4-Acetylamino-4-phenyl-piperidin-1-ylmethyl)-1-(3-chlorophenyl)-cyclopropanecarboxylic acid (4-fluoro-benzyl)-methyl-amide;
129. 2-(4-Acetylamino-4-phenyl-piperidin-1-ylmethyl)-1-(3-fluorophenyl)-cyclopropanecarboxylic acid (4-fluoro-benzyl)-methyl-amide;
130. 1-(3,4-Dichlorophenyl)-2-(4-phenyl-piperidin-1-ylmethyl)-cyclopropanecarboxylic acid methyl-naphthalen-1-ylmethyl-amide;
131. 1-(3,4-Dichlorophenyl)-2-[1-acetyl-5-fluoro-spiro[2,3-dihydro-1H-indol-3-yl-3,4'-piperidine-1'-yl-methyl]-cyclopropanecarboxylic acid methyl-naphthalen-1-ylmethyl-amide;
132. 1-(3,4-Dichlorophenyl)-2-(4-Acetylamino-4-phenyl-piperidin-1-ylmethyl)-cyclopropanecarboxylic acid methyl-naphthalen-1-ylmethyl-amide;

or a salt thereof, such as a pharmaceutically acceptable salt.

In an even more preferred embodiment of formula I, the compound is any one of the following compounds:

1a. (1S,2R)-2-(4-Acetylamino-4-phenyl-piperidin-1-ylmethyl)-1-(3,4-dichlorophenyl)-cyclopropanecarboxylic acid benzyl-methyl-amide;
2a. (1S,2R)-2-[4-(Acetyl-methyl-amino)-4-phenyl-piperidin-1-ylmethyl]-1-(3,4-dichlorophenyl)-cyclopropanecarboxylic acid benzyl-methyl-amide;
3a. (1S,2R)-2-[1-acetyl-spiro[2,3-dihydro-1H-indol-3-yl-3,4'-piperidine-1'-yl-methyl]-1-(3,4-dichlorophenyl)-cyclopropanecarboxylic acid benzyl-methyl-amide;
4a. (1S,2R)-2-[1-acetyl-5-fluorospiro[2,3-dihydro-1H-indol-3-yl-3,4'-piperidine-1'-yl-methyl]-1-(3,4-dichlorophenyl)-cyclopropanecarboxylic acid benzyl-methyl-amide;
5a. (1S,2R)-2-[1-acetyl-spiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl) amide;
6a. (1S,2R)-2-[1-acetyl-5-fluorospiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl)amide;
7a. (1S,2R)-1-Phenyl-2-[4-phenyl-4-(piperidine-1-carbonyl)-piperidin-1-ylmethyl]-cyclopropanecarboxylic acid benzyl-methyl-amide;
8a. (1S,2R)-2-[1-methanesulphonyl-spiro[2,3-dihydro-1H-indol-3-yl-3,4'-piperidine-1'-yl-methyl]-1-phenyl-cyclopropanecarboxylic acid benzyl-methyl-amide;
9a. (1S,2R)-2-(4-Acetyl-4-phenyl-piperidin-1-ylmethyl)-1-phenyl-cyclopropanecarboxylic acid benzyl-methyl-amide;
10a. (1S,2R)-2-[4-(4-Chloro-3-trifluoromethyl-phenyl)-4-hydroxy-piperidin-1-ylmethyl]-1-phenyl-cyclopropanecarboxylic acid benzyl-methyl-amide;
11a. (1S,2R)-2-[1-acetyl-5-fluorospiro[2,3-dihydro-1H-indol-3-yl-3,4'-piperidine-1'-yl-methyl]-1-phenyl-cyclopropanecarboxylic acid benzyl-methyl-amide;
12a. (1S,2R)-2-(4-Acetylamino-4-phenyl-piperidin-1-ylmethyl)-1-(4-chloro-phenyl)-cyclopropanecarboxylic acid benzyl-methyl-amide;
13a. (1S,2R)-1-(4-Chloro-phenyl)-2-[4-phenyl-4-(piperidine-1-carbonyl)-piperidin-1-ylmethyl]-cyclopropanecarboxylic acid benzyl-methyl-amide;
14a. (1S,2R)-2-[4-(Acetyl-methyl-amino)-4-phenyl-piperidin-1-ylmethyl]-1-(4-chloro-phenyl)-cyclopropanecarboxylic acid benzyl-methyl-amide;
15a. (1S,2R)-2-(4-Acetyl-4-phenyl-piperidin-1-ylmethyl)-1-(4-chloro-phenyl)-cyclopropanecarboxylic acid benzyl-methyl-amide;

16a. (1S,2R)-2-[1-acetyl-spiro[2,3-dihydro-1H-indol-3-yl-3,4'-piperidine-1'-yl-methyl]-1-(4-chlorophenyl)-cyclopropanecarboxylic acid benzyl-methyl-amide;
17a. (1S,2R)-2-[1-acetyl-5-fluorospiro[2,3-dihydro-1H-indol-3-yl-3,4'-piperidine-1'-yl-methyl]-1-(4-chlorophenyl)-cyclopropanecarboxylic acid benzyl-methyl-amide;
18a. (1S,2R)-2-(4-Acetylamino-4-phenyl-piperidin-1-ylmethyl)-1-(3,4-difluoro-phenyl)-cyclopropanecarboxylic acid methyl-(1-phenyl-ethyl)-amide;
19a. (1S,2R)-2-[4-(Acetyl-methyl-amino)-4-phenyl-piperidin-1-ylmethyl]-1-(3,4-difluoro-phenyl)-cyclopropanecarboxylic acid methyl-([S]-1-phenyl-ethyl)-amide;
20a. (1S,2R)-2-[1-acetyl-5-fluorospiro[2,3-dihydro-1H-indol-3-yl-3,4'-piperidine-1'-yl-methyl]-1-(3,4-difluorophenyl)-cyclopropanecarboxylic acid methyl-([S]-1-phenyl-ethyl)amide;
21a. (1S,2R)-2-(4-Acetylamino-4-phenyl-piperidin-1-ylmethyl)-1-phenyl-cyclopropanecarboxylic acid (4-fluoro-benzyl)-methyl-amide;
22a. (1S,2R)-2-[4-(Acetyl-methyl-amino)-4-phenyl-piperidin-1-ylmethyl]-1-phenyl-cyclopropanecarboxylic acid (4-fluoro-benzyl)-methyl-amide;
23a. (1S,2R)-2-[1-acetyl-spiro[2,3-dihydro-1H-indol-3-yl-3,4'-piperidine-1'-yl-methyl]-1-phenyl-cyclopropanecarboxylic acid (4-fluoro-benzyl)-methyl-amide;
24a. (1S,2R)-2-[4-(4-Chloro-3-trifluoromethyl-phenyl)-4-hydroxy-piperidin-1-ylmethyl]-1-phenyl-cyclopropanecarboxylic acid (4-fluoro-benzyl)-methyl-amide;
25a. (1S,2R)-2-[1-acetyl-5-fluorospiro[2,3-dihydro-1H-indol-3-yl-3,4'-piperidine-1'-yl-methyl]-1-phenyl-cyclopropanecarboxylic acid (4-fluoro-benzyl)-methyl-amide;
26a. (1S,2R)-2-[4-(Acetyl-methyl-amino)-4-phenyl-piperidin-1-ylmethyl]-1-(4-chloro-phenyl)-cyclopropanecarboxylic acid (4-fluoro-benzyl)-methyl-amide;
27a. (1S,2R)-2-[1-acetyl-5-fluoro-spiro[2,3-dihydro-1H-indol-3,3'-(8'-aza-bicyclo[3.2.1]octane-8'-yl)]-1-(4-chlorophenyl)-cyclopropanecarboxylic acid (4-fluoro-benzyl)-methyl-amide;
28a. (1S,2R)-2-(4-Acetyl-4-phenyl-piperidin-1-ylmethyl)-1-(4-chloro-phenyl)-cyclopropanecarboxylic acid (4-fluoro-benzyl)-methyl-amide;
29a. (1S,2R)-2-[1-acetyl-spiro[2,3-dihydro-1H-indol-3-yl-3,4'-piperidine-1'-yl-methyl]-1-(4-chlorophenyl)-cyclopropanecarboxylic acid (4-fluoro-benzyl)-methyl-amide;
30a. (1S,2R)-2-[1-acetyl-5-fluorospiro[2,3-dihydro-1H-indol-3-yl-3,4'-piperidine-1'-yl-methyl]-1-(4-chlorophenyl)-cyclopropanecarboxylic acid (4-fluoro-benzyl)-methyl-amide;
31a. (1S,2R)-1-(4-Fluoro-phenyl)-2-[4-phenyl-4-(piperidine-1-carbonyl)-piperidin-1-ylmethyl]-cyclopropanecarboxylic acid (4-fluoro-benzyl)-methyl-amide;
32a. (1S,2R)-2-[1-acetyl-5-fluorospiro[2,3-dihydro-1H-indol-3-yl-3,4'-piperidine-1'-yl-methyl]-1-(4-fluorophenyl)-cyclopropanecarboxylic acid (4-fluoro-benzyl)-methyl-amide;
33a. (1S,2R)-1-(3,4-Difluoro-phenyl)-2-[4-phenyl-4-(piperidine-1-carbonyl)-piperidin-1-ylmethyl]-cyclopropanecarboxylic acid-methyl-amide;
34a. (1S,2R)-2-[1-acetyl-5-fluoro-spiro[2,3-dihydro-1H-indol-3,3'-(8'-aza-bicyclo[3.2.1]octane-8'-yl)]-1-(3,4-difluorophenyl)-cyclopropanecarboxylic acid (4-fluoro-benzyl)-methyl-amide;
35a. (1S,2R)-2-[1-acetyl-5-fluorospiro[2,3-dihydro-1H-indol-3-yl-3,4'-piperidine-1'-yl-methyl]-1-(3,4-fluorophenyl)-cyclopropanecarboxylic acid (4-fluoro-benzyl)-methyl-amide;
36a. (1S,2R)-1-(3,4-Dichlorophenyl)-2-[4-phenyl-4-(piperidine-1-carbonyl)-piperidin-1-ylmethyl]-cyclopropanecarboxylic acid benzyl-methyl-amide;
37a. (1S,2R)-2-(4-Acetyl-4-phenyl-piperidin-1-ylmethyl)-1-(3,4-dichlorophenyl)-cyclopropanecarboxylic acid benzyl-methyl-amide;
38a. (1S,2R)-2-[1-acetyl-5-fluorospiro[2,3-dihydro-1H-indol-3-yl-3,4'-piperidine-1'-yl-methyl]-1-(4-fluorophenyl)-cyclopropanecarboxylic acid methyl-([S]-1-phenyl-ethyl)amide;
39a. (1S,2R)-2-(4-Acetylamino-4-phenyl-piperidin-1-ylmethyl)-1-(3,4-dichlorophenyl)-cyclopropanecarboxylic acid methyl-(1-phenyl-ethyl)-amide;
40a. (1S,2R)-(1S,2R)-1-(3,4-Dichloro-phenyl)-2-[4-phenyl-4-(piperidine-1-carbonyl)-piperidin-1-ylmethyl]-cyclopropanecarboxylic acid methyl-([S]-1-phenyl-ethyl)amide;
41a. (1S,2R)-2-[4-(Acetyl-methyl-amino)-4-phenyl-piperidin-1-ylmethyl]-1-(3,4-dichlorophenyl)-cyclopropanecarboxylic acid methyl-([S]-1-phenyl-ethyl)-amide;
42a. (1S,2R)-1-Phenyl-2-[4-phenyl-4-(piperidine-1-carbonyl)-piperidin-1-ylmethyl]-cyclopropanecarboxylic acid (4-fluoro-benzyl)-methyl-amide;
43a. (1S,2R)-1-(4-Chloro-phenyl)-2-[4-phenyl-4-(piperidine-1-carbonyl)-piperidin-1-ylmethyl]-cyclopropanecarboxylic acid (4-fluoro-benzyl)-methyl-amide;
44a. (1S,2R)-2-(4-Acetylamino-4-phenyl-piperidin-1-ylmethyl)-1-(4-chloro-phenyl)-cyclopropanecarboxylic acid (4-fluoro-benzyl)-methyl-amide;
45a. (1S,2R)-2-(4-Acetylamino-4-phenyl-piperidin-1-ylmethyl)-1-(4-chloro-phenyl)-cyclopropanecarboxylic acid (2-chloro-benzyl)-methyl-amide;
46a. (1S,2R)-1-(4-Chloro-phenyl)-2-[4-phenyl-4-(piperidine-1-carbonyl)-piperidin-1-ylmethyl]-cyclopropanecarboxylic acid (2-chloro-benzyl)-methyl-amide;
47a. (1S,2R)-2-[4-(Acetyl-methyl-amino)-4-phenyl-piperidin-1-ylmethyl]-1-(4-chloro-phenyl)-cyclopropanecarboxylic acid (2-chloro-benzyl)-methyl-amide;
48a. (1S,2R)-2-[1-acetyl-5-fluorospiro[2,3-dihydro-1H-indol-3-yl-3,4'-piperidine-1'-yl-methyl]-1-(4-chlorophenyl)-cyclopropanecarboxylic acid (2-chlorobenzyl)-methyl-amide;
49a. (1S,2R)-2-[4-(Acetyl-methyl-amino)-4-phenyl-piperidin-1-ylmethyl]-1-(4-fluoro-phenyl)-cyclopropanecarboxylic acid (2-chloro-benzyl)-methyl-amide;
50a. (1S,2R)-2-[4-(Acetyl-methyl-amino)-4-phenyl-piperidin-1-ylmethyl]-1-(3,4-difluoro-phenyl)-cyclopropanecarboxylic acid (2-chloro-benzyl)-methyl-amide;
51a. (1S,2R)-2-(4-Acetylamino-4-phenyl-piperidin-1-ylmethyl)-1-(3,4-dichlorophenyl)-cyclopropanecarboxylic acid (2-chloro-benzyl)-methyl-amide;
52a. (1S,2R)-1-(3,4-Dichlorophenyl)-2-[4-phenyl-4-(piperidine-1-carbonyl)-piperidin-1-ylmethyl]-cyclopropanecarboxylic acid (2-chloro-benzyl)-methyl-amide;
53a. (1S,2R)-2-[4-(Acetyl-methyl-amino)-4-phenyl-piperidin-1-ylmethyl]-1-(3,4-dichlorophenyl)-cyclopropanecarboxylic acid (2-chloro-benzyl)-methyl-amide;
54a. (1S,2R)-2-[1-acetyl-spiro[2,3-dihydro-1H-indol-3-yl-3,4'-piperidine-1'-yl-methyl]-1-(3,4-dichlorophenyl)-cyclopropanecarboxylic acid (2-chlorobenzyl)-methyl-amide;
55a. (1S,2R)-1-(3,4-Dichlorophenyl)-2-(4-phenyl-piperidin-1-ylmethyl)-cyclopropanecarboxylic acid benzyl-methyl-amide;
56a. (1S,2R)-2-(4-Acetylamino-4-phenyl-piperidin-1-ylmethyl)-1-(3,4-dichlorophenyl)-cyclopropanecarboxylic acid (1-methyl-1-phenyl-ethyl)-amide.

57a (1S,2R)-2-(4-phenyl-piperidin-1-ylmethyl)-1-(3,4-dichlorophenyl)-cyclopropanecarboxylic acid benzyl-ethyl-amide 58a. (1S,2R)-2-(4-Acetylamino-4-phenyl-piperidin-1-ylmethyl)-1-(3,4-dichlorophenyl)-cyclopropanecarboxylic acid benzyl-methyl-amide-([R]-1-phenyl-ethyl)amide 59a. (1R,2S)-2-(4-Acetylamino-4-phenyl-piperidin-1-ylmethyl)-1-(3,4-dichlorophenyl)-cyclopropanecarboxylic acid benzyl-methyl-amide;

60a. (1R,2R)-2-(4-Acetylamino-4-phenyl-piperidin-1-ylmethyl)-1-(3,4-dichlorophenyl)-cyclopropanecarboxylic acid benzyl-methyl-amide; and 61a. (1S,2S)-2-(4-Acetylamino-4-phenyl-piperidin-1-ylmethyl)-1-(3,4-dichlorophenyl)-cyclopropanecarboxylic acid benzyl-methyl-amide;

62a (1S,2R)-2-(4-Acetylamino-4-phenyl-piperidin-1-ylmethyl)-1-(3,4-dichlorophenyl)-cyclopropanecarboxylic acid methyl-([R]1-phenyl-ethyl)-amide;

63a (1S,2R)-2-[4-(Acetyl-methyl-amino)-4-phenyl-piperidin-1-ylmethyl]-1-(3,4-dichlorophenyl)-cyclopropanecarboxylic acid methyl-([R]-1-phenyl-ethyl)-amide;

64a. (1S,2R)-2-[1-acetyl-spiro[2,3-dihydro-1H-indol-3-yl-3,4'-piperidine-1'-yl-methyl]-1-(3,4-dichlorophenyl)-cyclopropanecarboxylic acid methyl-([R]-1-phenyl-ethyl)amide;

65a. (1S,2R)-2-[1-acetyl-5-fluoro-spiro[2,3-dihydro-1H-indol-3-yl-3,4'-piperidine-1'-yl-methyl]-1-(3,4-dichlorophenyl)-cyclopropanecarboxylic acid methyl-([R]-1-phenyl-ethyl)amide;

66a. (1S,2R)-2-(4-Acetylamino-4-phenyl-piperidin-1-ylmethyl)-1-phenyl-cyclopropanecarboxylic acid benzyl-methyl-amide;

67a. (1S,2R)-1-(3,4-Dichlorophenyl)-2-[4-phenyl-4-(piperidine-1-carbonyl)-piperidin-1-ylmethyl]-cyclopropanecarboxylic acid methyl-([S]-1-phenyl-ethyl)-amide;

68a. (1S,2R)-2-[1-acetyl-5-fluoro-spiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl)amide;

69a. (1S,2R)-1-Phenyl-2-[4-phenyl-4-(piperidine-1-carbonyl)-piperidin-1-ylmethyl]-cyclopropanecarboxylic acid (4-fluoro-benzyl)-methyl-amide;

70a. (1S,2R)-2-(4-Acetyl-4-phenyl-piperidin-1-ylmethyl)-1-phenyl-cyclopropanecarboxylic acid (4-fluoro-benzyl)-methyl-amide;

71a. (1S,2R)-2-[1-methanesulphonyl-spiro[2,3-dihydro-1H-indol-3-yl-3,4'-piperidine-1'-yl-methyl]-1-(4-fluophenyl)-cyclopropanecarboxylic acid (4-fluoro-benzyl)-methyl-amide;

72a. (1S,2R)-2-[4-(Acetyl-methyl-amino)-4-phenyl-piperidin-1-ylmethyl]-1-(4-fluorophenyl)-cyclopropanecarboxylic acid (4-fluoro-benzyl)-methyl-amide;

73a. (1S,2R)-2-(4-Acetyl-4-phenyl-piperidin-1-ylmethyl)-1-(4-fluorophenyl)-cyclopropanecarboxylic acid (4-fluoro-benzyl)-methyl-amide;

74a. (1S,2R)-2-[1-acetyl-spiro[2,3-dihydro-1H-indol-3-yl-3,4'-piperidine-1'-yl-methyl]-1-(4-fluorophenyl)-cyclopropanecarboxylic acid (4-fluoro-benzyl)-methyl-amide;

75a. (1S,2R)-2-(4-Acetyl-4-phenyl-piperidin-1-ylmethyl)-1-(3,4-difluorophenyl)-cyclopropanecarboxylic acid (4-fluoro-benzyl)-methyl-amide;

76a. (1S,2R)-2-[1-acetyl-spiro[2,3-dihydro-1H-indol-3-yl-3,4'-piperidine-1'-yl-methyl]-1-(3,4-difluorophenyl)-cyclopropanecarboxylic acid (4-fluoro-benzyl)-methyl-amide;

77a. (1S,2R)-1-(4-Fluoro-phenyl)-2-[4-phenyl-4-(piperidine-1-carbonyl)-piperidin-1-ylmethyl]-cyclopropanecarboxylic acid methyl-([S]1-phenyl-ethyl)-amide;

78a. (1S,2R)-2-(4-Acetyl-4-phenyl-piperidin-1-ylmethyl)-1-(4-chlorophenyl)-cyclopropanecarboxylic acid (2-chloro-benzyl)-methyl-amide;

79a. (1S,2R)-2-[1-acetyl-spiro[2,3-dihydro-1H-indol-3-yl-3,4'-piperidine-1'-yl-methyl]-1-(4-chlorophenyl)-cyclopropanecarboxylic acid (2-chloro-benzyl)-methyl-amide;

80a. (1S,2R)-2-(4-Acetylamino-4-phenyl-piperidin-1-ylmethyl)-1-(4-fluorophenyl)-cyclopropanecarboxylic acid (2-chloro-benzyl)-methyl-amide;

81a. (1S,2R)-1-(4-Fluoro-phenyl)-2-[4-phenyl-4-(piperidine-1-carbonyl)-piperidin-1-ylmethyl]-cyclopropanecarboxylic acid (2-chloro-benzyl)-methyl-amide;

82a. (1S,2R)-2-(4-Acetylamino-4-phenyl-piperidin-1-ylmethyl)-1-(3,4-difluorophenyl)-cyclopropanecarboxylic acid (2-chloro-benzyl)-methyl-amide;

83a. (1S,2R)-1-(3,4-Difluorophenyl)-2-[4-phenyl-4-(piperidine-1-carbonyl)-piperidin-1-ylmethyl]-cyclopropanecarboxylic acid (2-chloro-benzyl)-methyl-amide;

84a. (1S,2R)-2-[1-acetyl-spiro[2,3-dihydro-1H-indol-3-yl-3,4'-piperidine-1'-yl-methyl]-1-(3,4-difluorophenyl)-cyclopropanecarboxylic acid (2-chloro-benzyl)-methyl-amide;

85a. (1S,2R)-2-[1-acetyl-5-fluoro-spiro[2,3-dihydro-1H-indol-3-yl-3,4'-piperidine-1'-yl-methyl]-1-(3,4-difluorophenyl)-cyclopropanecarboxylic acid (2-chloro-benzyl)-methyl-amide;

86a. (1S,2R)-1-(3,4-Dichlorophenyl)-2-(4-phenyl-piperidin-1-ylmethyl)-cyclopropanecarboxylic acid 3,4-dichloro-benzylamide;

87a. (1S,2R)-1-(3,4-Dichlorophenyl)-2-(4-phenyl-piperidin-1-ylmethyl)-cyclopropanecarboxylic acid 3,4-dimethoxy-benzylamide;

88a. (1S,2R)-2-(4-Acetylamino-4-phenyl-piperidin-1-ylmethyl)-1-(3,4-dichlorophenyl)-cyclopropanecarboxylic acid phenylamide;

89a. (1S,2R)-2-(4-Acetylamino-4-phenyl-piperidin-1-ylmethyl)-1-(3,4-dichlorophenyl)-cyclopropanecarboxylic acid (1-methyl-1-phenyl-ethyl)-amide;

90a. (1S,2R)-1-Phenyl-2-[4-(3-trifluoromethylphenyl)-piperazin-1-ylmethyl]-cyclopropanecarboxylic acid benzyl-methyl-amide;

91a. (1S,2R)-2-(4-Benzyl-piperazin-1-ylmethyl)-1-(4-chlorophenyl)-cyclopropanecarboxylic acid (4-fluoro-benzyl)-methyl-amide;

92a. (1S,2R)-1-(4-chlorophenyl)-2-[4-(3-trifluoromethylphenyl)-piperazin-1-ylmethyl]-cyclopropanecarboxylic acid 4-fluorobenzyl-methyl-amide;

93a. (1S,2R)-2-(4-Benzyl-piperazin-1-ylmethyl)-1-(4-chlorophenyl)-cyclopropanecarboxylic acid benzyl-methyl-amide;

94a. (1S,2R)-2-(4-Benzyl-piperazin-1-ylmethyl)-1-phenyl-cyclopropanecarboxylic acid benzyl-methyl-amide;

95a. (1S,2R)-1-(4-chlorophenyl)-2-[4-(3-trifluoromethylphenyl)-piperazin-1-ylmethyl]-cyclopropanecarboxylic acid benzyl-methyl-amide;

96a. (1S,2R)-1-phenyl-2-[4-(3-trifluoromethylphenyl)-piperazin-1-ylmethyl]-cyclopropanecarboxylic acid 4-fluorobenzyl-methyl-amide;

97a. (1S,2R)-2-(4-Acetylamino-4-phenyl-piperidin-1-ylmethyl)-1-(3,4-dichloro-phenyl)-cyclopropanecarboxylic acid benzyl amide;

98a. (1S,2R)-2-[1-acetyl-5-fluoro-spiro[2,3-dihydro-1H-indol-3-yl-3,4'-piperidine-1'-yl-methyl]-1-(3,4-diflurophenyl)-cyclopropanecarboxylic acid (2-fluoro-benzyl)-amide;

99a. (1S,2R)-2-(4-Acetylamino-4-phenyl-piperidin-1-ylmethyl)-1-(3,4-dichlorophenyl)-cyclopropanecarboxylic acid methyl-[1-(4-methoxyphenyl)-ethyl]-amide;

100a. (1S,2R)-2-(4-Acetylamino-4-phenyl-piperidin-1-ylmethyl)-1-(3,4-dichloro-phenyl)-cyclopropanecarboxylic acid (2-chlorobenzyl)amide;

101a. (1S,2R)-2-(4-Acetylamino-4-phenyl-piperidin-1-ylmethyl)-1-(3,4-dichloro-phenyl)-cyclopropanecarboxylic acid (3,4-dichlorobenzyl)amide;

102a. (1S,2R)-2-(4-Acetylamino-4-phenyl-piperidin-1-ylmethyl)-1-(3,4-dichloro-phenyl)-cyclopropanecarboxylic acid methyl-phenyl-amide;

103a. (1S,2R)-2-(4-Acetylamino-4-phenyl-piperidin-1-ylmethyl)-1-(4-methoxy-phenyl)-cyclopropanecarboxylic acid (4-fluoro-benzyl)-methyl-amide;

104a. (1S,2R)-2-(4-Acetylamino-4-phenyl-piperidin-1-ylmethyl)-1-p-tolyl-cyclopropanecarboxylic acid (4-fluoro-benzyl)-methyl-amide;

105a. (1S,2R)-2-(4-Acetylamino-4-phenyl-piperidin-1-ylmethyl)-1-m-tolyl-cyclopropanecarboxylic acid benzyl-methyl-amide;

106a. (1S,2R)-2-(4-Acetylamino-4-phenyl-piperidin-1-ylmethyl)-1-m-tolyl-cyclopropanecarboxylic acid (4-fluoro-benzyl)-methyl-amide;

107a. (1S,2R)-2-(4-Acetylamino-4-phenyl-piperidin-1-ylmethyl)-1-(3-methoxy-phenyl)-cyclopropanecarboxylic acid (4-fluoro-benzyl)-methyl-amide;

108a. (1S,2R)-2-(4-Acetylamino-4-phenyl-piperidin-1-ylmethyl)-1-(4-methoxy-phenyl)-cyclopropanecarboxylic acid benzyl-methyl-amide;

109a. (1S,2R)-2-(4-Acetylamino-4-phenyl-piperidin-1-ylmethyl)-1-p-tolyl-cyclopropanecarboxylic acid benzyl-methyl-amide;

110a. (1S,2R)-2-(4-Acetylamino-4-phenyl-piperidin-1-ylmethyl)-1-(3-methoxy-phenyl)-cyclopropanecarboxylic acid benzyl-methyl-amide;

111a. (1S,2R)-1-Phenyl-2-(4-phenyl-4-ureido-piperidin-1-ylmethyl)-cyclopropanecarboxylic acid (4-fluoro-benzyl)-methyl-amide;

112a. (1S,2R)-1-(3,4-Dichlorophenyl)-2-(4-phenyl-4-ureido-piperidin-1-ylmethyl)-cyclopropanecarboxylic acid-benzyl-methyl-amide;

113a. (1S,2R)-1-Phenyl-2-[4-(3-methyl-ureido)-4-phenyl-piperidin-1-ylmethyl]-cyclopropanecarboxylic acid (4-fluorobenzyl)-methyl-amide;

114a. (1S,2R)-2-[4-(3-Methyl-ureido)-4-phenyl-piperidin-1-ylmethyl]-1-(3,4-dichlorophenyl)-cyclopropanecarboxylic acid benzyl-methyl-amide;

115a. (1S,2R)-N-(1-{2-[(4-Fluoro-benzyl)-methyl-carbamoyl]-2-phenyl-cyclopropylmethyl}-4-phenyl-piperidin-4-yl)-oxalamide;

116a. (1S,2R)-N-(1-{2-[benzyl-methyl-carbamoyl]-2-(3,4-dichlorophenyl)-cyclopropylmethyl}-4-phenyl-piperidin-4-yl)-oxalamide;

117a. (1S,2R)-1-Phenyl-2-(4-methanesulfonylamino-4-phenyl-piperidin-1-ylmethyl)-cyclopropanecarboxylic acid-(4-fluorobenzyl)-methyl-amide;

118a. (1S,2R)-2-(4-Methanesulfonylamino-4-phenyl-piperidin-1-ylmethyl)-1-(3,4-dichlorophenyl)-cyclopropanecarboxylic acid-benzyl-methyl-amide;

119a. (1S,2R)-{1-[2-((4-fluoro-benzyl)-methyl-carbamoyl)-2-phenyl-cyclopropylmethyl]-4-phenyl-piperidin-4-yl}-carbamic acid methyl ester;

120a. (1S,2R)-(1-{2-benzyl-methyl-carbamoyl]-2-(3,4-dichlorophenyl)-cyclopropylmethyl}-4-phenyl-piperidin-4-yl)-carbamic acid methyl ester;

121a. (1S,2R)-1-(3,4-Dichloro-phenyl)-2-[4-(3,3-dimethyl-ureido)-4-phenyl-piperidin-1-ylmethyl]-cyclopropanecarboxylic acid benzyl-methyl-amide;

122a. (1S,2R)-1-phenyl-2-[4-(3,3-dimethyl-ureido)-4-phenyl-piperidin-1-ylmethyl]-cyclopropanecarboxylic acid (4-fluorobenzyl)-methyl-amide;

123a. (1S,2R)-2-[2-(4-Acetylamino-4-phenyl-piperidin-1-yl)-ethyl]-1-(3,4-dichlorophenyl)-cyclopropanecarboxylic acid (4-fluoro-benzyl)-methyl-amide;

124a. (1S,2R)-2-[3-(4-Acetylamino-4-phenyl-piperidin-1-yl)-propyl]-1-(3,4-dichlorophenyl)-cyclopropanecarboxylic acid (4-fluoro-benzyl)-methyl-amide;

125a. (1S,2R)-2-[4-(2-Acetylamino-5-fluorophenyl)-piperidin-1-ylmethyl]-1-(3,4-dichlorophenyl)-cyclopropanecarboxylic acid (4-fluoro-benzyl)-methyl-amide;

126a. (1S,2R)-2-(4-Acetylamino-4-phenyl-piperidin-1-ylmethyl)-1-(3,4-dimethylphenyl)-cyclopropanecarboxylic acid (4-fluoro-benzyl)-methyl-amide;

127a. (1S,2R)-2-(4-Acetylamino-4-phenyl-piperidin-1-ylmethyl)-1-(3,4-dichlorophenyl)-cyclopropanecarboxylic acid (4-fluoro-benzyl)-methyl-amide;

128a. (1S,2R)-2-(4-Acetylamino-4-phenyl-piperidin-1-ylmethyl)-1-(3-chlorophenyl)-cyclopropanecarboxylic acid (4-fluoro-benzyl)-methyl-amide;

129a. (1S,2R)-2-(4-Acetylamino-4-phenyl-piperidin-1-ylmethyl)-1-(3-fluorophenyl)-cyclopropanecarboxylic acid (4-fluoro-benzyl)-methyl-amide;

130a. (1S,2R)-1-(3,4-Dichlorophenyl)-2-(4-phenyl-piperidin-1-ylmethyl)-cyclopropanecarboxylic acid methyl-naphthalen-1-ylmethyl-amide;

131a. (1S,2R)-1-(3,4-Dichlorophenyl)-2-[1-acetyl-5-fluoro-spiro[2,3-dihydro-1H-indol-3-yl-3,4'-piperidine-1'-yl-methyl]-cyclopropanecarboxylic acid methyl-naphthalen-1-ylmethyl-amide;

132a. (1S,2R)-1-(3,4-Dichlorophenyl)-2-(4-Acetylamino-4-phenyl-piperidin-1-ylmethyl)-cyclopropanecarboxylic acid methyl-naphthalen-1-ylmethyl-amide;

or a salt thereof, such as a pharmaceutically acceptable salt.

In further embodiments of formula I, the compound is any one of:

5b. 2-[1-acetyl-spiro[2,3-dihydro-1H-indol-3-yl-3,4'-piperidine-1'-yl-methyl]-1-(3,4-dichlorophenyl)-cyclopropanecarboxylic acid methyl-(1-phenyl-ethyl)amide;

6b. 2-[1-acetyl-5-fluorospiro[2,3-dihydro-1H-indol-3-yl-3,4'-piperidine-1'-yl-methyl]-1-(3,4-dichlorophenyl)-cyclopropanecarboxylic acid methyl-(1-phenyl-ethyl)amide;

19b. 2-[4-(Acetyl-methyl-amino)-4-phenyl-piperidin-1-ylmethyl]-1-(3,4-difluoro-phenyl)-cyclopropanecarboxylic acid methyl-(1-phenyl-ethyl)-amide;

20b. 2-[1-acetyl-5-fluorospiro[2,3-dihydro-1H-indol-3-yl-3,4'-piperidine-1'-yl-methyl]-1-(3,4-difluorophenyl)-cyclopropanecarboxylic acid methyl-(1-phenyl-ethyl)amide;

38b. 2-[1-acetyl-5-fluorospiro[2,3-dihydro-1H-indol-3-yl-3,4'-piperidine-1'-yl-methyl]-1-(4-fluorophenyl)-cyclopropanecarboxylic acid methyl-(1-phenyl-ethyl)amide;

40b. 1-(3,4-Dichlorophenyl)-2-[4-phenyl-4-(piperidine-1-carbonyl)-piperidin-1-ylmethyl]-cyclopropanecarboxylic acid methyl-(1-phenyl-ethyl)-amide;

41b. 2-[4-(Acetyl-methyl-amino)-4-phenyl-piperidin-1-ylmethyl]-1-(3,4-dichlorophenyl)-cyclopropanecarboxylic acid methyl-(1-phenyl-ethyl)-amide;

58b. 2-(4-Acetylamino-4-phenyl-piperidin-1-ylmethyl)-1-(3,4-dichlorophenyl)-cyclopropanecarboxylic acid benzyl-methyl-amide-(1-phenyl-ethyl)amide
62b. 1S,2R)-2-(4-Acetylamino-4-phenyl-piperidin-1-ylmethyl)-1-(3,4-dichlorophenyl)-cyclopropanecarboxylic acid methyl-(1-phenyl-ethyl)-amide;
63b. 2-[4-(Acetyl-methyl-amino)-4-phenyl-piperidin-1-ylmethyl]-1-(3,4-dichlorophenyl)-cyclopropanecarboxylic acid methyl-(1-phenyl-ethyl)-amide;
64b. 2-[1-acetyl-spiro[2,3-dihydro-1H-indol-3-yl-3,4'-piperidine-1'-yl-methyl]-1-(3,4-dichlorophenyl)-cyclopropanecarboxylic acid methyl-(1-phenyl-ethyl)amide;
65b. 2-[1-acetyl-5-fluoro-spiro[2,3-dihydro-1H-indol-3-yl-3,4'-piperidine-1'-yl-methyl]-1-(3,4-dichlorophenyl)-cyclopropanecarboxylic acid methyl-(1-phenyl-ethyl)amide;
67b. 1-(3,4-Dichlorophenyl)-2-[4-phenyl-4-(piperidine-1-carbonyl)-piperidin-1-ylmethyl]-cyclopropanecarboxylic acid methyl-(1-phenyl-ethyl)-amide;
68b. 2-[1-acetyl-5-fluoro-spiro[2,3-dihydro-1H-indol-3-yl-3,4'-piperidine-1'-yl-methyl]-1-(3,4-dichlorophenyl)-cyclopropanecarboxylic acid methyl-(1-phenyl-ethyl)amide;
77b. 1-(4-Fluoro-phenyl)-2-[4-phenyl-4-(piperidine-1-carbonyl)-piperidin-1-ylmethyl]-cyclopropanecarboxylic acid methyl-(1-phenyl-ethyl)-amide;

or a salt thereof, such as a pharmaceutically acceptable salt.

Within the invention is also a compound selected from the group consisting of 5b, 6b, 19b, 20b, 38b, 40b, 41b, 58b, 62b, 63b, 64b, 65b, 67b, 68b, 77b which is the (1S,2R)-isomer, i.e. having an absolute configuration as shown in formula IA; or a salt thereof, such as a pharmaceutically acceptable salt.

Other aspects of the invention relate to a compound of the invention of formula I which is the (1R,2R)-isomer (i.e. in contrast to formula IA which is the (1S,2R)-isomer).

Other aspects of the invention relate to a compound of the invention of formula I which is the (1S,2S)-isomer (i.e. in contrast to formula IA which is the (1S,2R)-isomer).

Other aspects of the invention relate to a compound of the invention of formula I which is the (1R,2S)-isomer (i.e. in contrast to formula IA which is the (1S,2R)-isomer).

The present invention also comprises salts of the compounds of the invention, typically, pharmaceutically acceptable salts. Such salts include pharmaceutical acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Also intended as pharmaceutical acceptable acid addition salts are the hydrates, which the present compounds, are able to form.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The invention also encompasses prodrugs of the present compounds, which on administration undergo chemical conversion by metabolic processes before becoming pharmacologically active substances. In general, such prodrugs will be functional derivatives of the compounds of the general formula (I), which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds (including salts thereof) of the invention are NK3 receptor antagonists having a human NK3 binding affinity ($K_i$) of 5 μM or less, typically of 1 μM or less, and preferably of 200 nM or less, e.g. as measured by the method described in Example 20.

A further objective of the present invention is to provide compounds, including salts thereof, with such activities which have one or more of the following parameters which are improved: solubility, metabolic stability and bioavailability compared to prior art compounds.

Pharmaceutical Use

As mentioned above the compounds of the invention are NK3 receptor antagonists and may thus be useful for treatment in a disorder or disease wherein the NK3 receptor is implicated.

Compounds of the invention and the salt thereof may be applicable for treatment, including prevention, of schizophrenia, psychotic disorders, depression, anxiety, Parkinson's disease, pain, convulsions, cough, asthma, airway hyperresponsiveness, microvascular hypersensitivity, bronchoconstriction, gut inflammation, inflammatory bowel disease, hypertension, imbalances in water and electrolyte homeostasis, ischemia, oedema or plasma extravasation. In a preferred embodiment, the compounds of the invention and the salt thereof can be used as an antipsychotic.

Thus, a compound of the invention may be useful for the treatment of a disease or disorder in the central nervous system.

In further embodiments, the compound of the invention or salt thereof may also have some NK1 and/or NK2 activity in addition to the NK3 activity as described herein. Accordingly, the compound of the invention and the salts thereof may also be useful for the treatment, including prevention, of diseases where the NK1 receptor and/or the NK2 receptor is implicated, especially emesis, depression or anxiety.

In a further aspect, the invention relates to a compound of the invention or salts thereof for use as a medicament.

The present invention also relates to a pharmaceutical composition comprising a compound of the invention or a salt thereof and a pharmaceutically acceptable carrier or a diluent. The composition may comprise any one of the embodiments of formula I described herein.

The present invention also relates to use of a compound of the invention or a salt thereof, for the preparation of a medicament for the treatment of a disease or disorder, wherein an NK receptor antagonist, in particular an NK3 receptor antagonist is beneficial. The medicament may comprise any one of the embodiments of formula I described herein.

In particular the present invention relates to use of a compound of the invention or a salt thereof for the preparation of a medicament for the treatment of any of the diseases indicated herein, including psychotic disorders, in particular schizophrenia.

In one aspect, the present invention relates to use of a compound of the invention or a salt thereof treatment of the positive symptoms of schizophrenia.

Further, the invention also relates to use of a compound of the invention or a salt thereof for the preparation of a medicament for the treatment or prevention of depression or anxiety. The invention also relates to use of a compound of the invention or a salt thereof for the preparation of a medicament for the treatment or prevention of Parkinson's disease. Further, the invention also relates to use of a compound of the invention or a salt thereof for the preparation of a medicament for the treatment or prevention of convulsions.

A further aspect of the invention relates to a method for the treatment or prevention of schizophrenia, psychotic disorders, depression, anxiety, Parkinson's disease, pain, convulsions, cough, asthma, airway hyperresponsiveness, microvascular hypersensitivity, bronchoconstriction, gut inflammation, inflammatory bowel disease, hypertension, imbalances in water and electrolyte homeostasis, ischemia, oedema or plasma extravasation, in a living animal body, including a human, comprising administering to a subject in need thereof a therapeutically effective amount of a compound of the invention or a pharmaceutically acceptable acid addition salt thereof. In general the invention also relates to use of a compound of the invention or a salt thereof for the preparation of a medicament for the treatment or prevention of these diseases/disorders.

The compounds of the invention or the salt thereof may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants, etc.

In an embodiment of the pharmaceutical composition, the compound of the invention administered in an amount of from about 0.001 to about 100 mg/kg body weight per day.

Conveniently, the compounds of the invention are administered in a unit dosage form containing said compounds in an amount of about 0.01 to 100 mg. The total daily dose is usually in the range of about 0.05-500 mg.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of a pharmaceutically acceptable acid. Representative examples are mentioned above.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatin, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablets, placed in a hard gelatin capsule in powder or pellet form or it can be in the form of a troche or lozenge. The amount of solid carrier will vary widely but will usually be from about 25 mg to about 1 g.

If a liquid carrier is used, the preparation may be in the form of a syrup, emulsion, soft gelatin capsule or sterile injectable liquid such as an aqueous or non-aqueous liquid suspension or solution.

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Typical examples of recipes for the formulation of the invention are as follows:

1) Tablets containing 5.0 mg of a compound of the invention calculated as the free base:

| Compound | 5.0 mg |
|---|---|
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| Compound | 0.5 mg |
|---|---|
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| Compound | 25 mg |
|---|---|
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per millilitre:

| Compound | 0.5 mg |
|---|---|
| Sorbitol | 5.1 mg |
| Acetic Acid | 0.05 mg |
| Saccharin sodium | 0.5 mg |
| Water | ad 1 mL |

Methods of Preparation of the Compounds of the Invention

The compounds of the invention may be prepared as follows:

Method 1 Alkylating an Amine of Formula III with an Alkylating Derivative of Formula II:

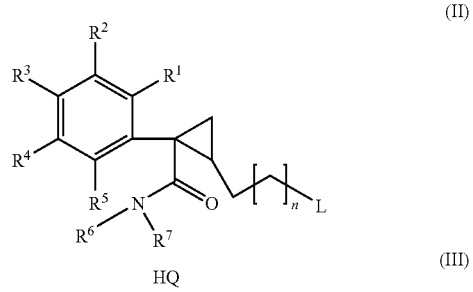

where $R^1$-$R^{36}$, n and Q are as defined herein, and L is a leaving group such as e.g. halogen, mesylate or tosylate;

Method 2 Reductive Alkylation of an Amine of Formula III with a Reagent of Formula IV:

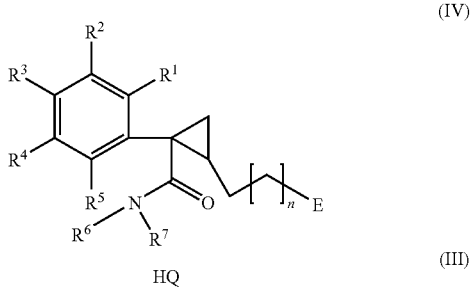

where $R^1$-$R^{36}$, n and Q are as defined herein, and E is an aldehyde or an activated carboxylic acid;

Method 3 Reacting an Amine of Formula VI with an Methyl Ester of Formula VII by the Use of Lewis Acid Catalyst:

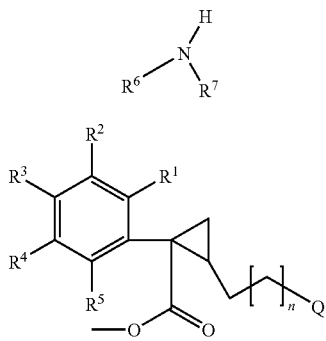

where $R^1$-$R^{36}$, n and Q are as defined herein,

Method 4 Reacting an Amine of Formula VI with an Acid of Formula VIII by the Use of an Activating Reagent or a Coupling Reagent:

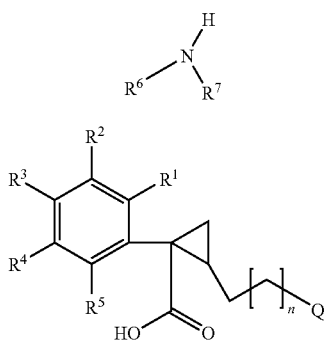

wherein $R^1$-$R^{36}$, n and Q are as defined herein,

Method 5 Reducing an Amine of Formula IX:

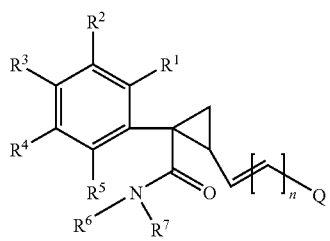

wherein $R^1$-$R^{36}$, n and Q are as defined herein, whereupon the compound of formula I is isolated as the free base or a pharmaceutically acceptable acid addition salt thereof.

The alkylation according to method 1 is conveniently performed in an organic solvent such as a suitably boiling alcohol or ketone, preferably in the presence of an organic or inorganic base (potassium carbonate, diisopropylethylamine or triethylamine) at reflux temperature. Alternatively, the alkylation can be performed at a fixed temperature, which is different from the boiling point, in one of the above-mentioned solvents or in dimethyl formamide (DMF), dimethylsulfoxide (DMSO), or N-methylpyrrolidin-2-one (NMP), preferably in the presence of a base. The alkylating derivatives of formula II with n=0 have been described in the literature or can be prepared in an analogues manner e.g. Shuto et al. *J. Org. Chem.* 1996, 61, 915 and Ronsisvalle et al. *Biorg. Med. Chem.* 2000, 8, 1503 and Bonnaud et al. *J. Med. Chem.* 1987, 30, 318. The alkylating derivatives of formula II with n=1 and n=2 can be prepared from alkylating derivatives of formula II with n=0 by standard chain elongation methods e.g. by substitution of an bromide of formula II with n=0 with cyanide followed by hydrolysis, reduction to the alcohol and conversion to a leaving group L resulting in alkylating derivatives of formula II with n=1. Correspondingly, alkylating derivatives of formula II with n=2 can be prepared by substitution of an bromide of formula II with n=0 with a malonic ester derivative, followed by hydrolysis, decarboxylation, reduction to the alcohol and conversion to a leaving group L. Standard chain elongation methods are described in standard works such as Houben-Weyl, Methoden der organischen Chemie (Methods of Organic Chemistry), Georg-Thieme-Verlag, Stuttgart; or Organic Reactions, John Wiley & Sons, Inc. New York, namely under reaction conditions such as those which are known and suitable for such reactions.

The amines of formula III are either commercially available or can be prepared by methods analogues to those described in the literature e.g. Marxer et al. *J. Org. Chem.* 1975, 40, 1427, by Parham et al. *J. Org. Chem.* 1976, 41, 2628 and by Bauer et al. *J. Med. Chem.* 1976, 19, 1315, Maligres et al. *Tetrahedron* 1997, 53, 10983, and by Cheng et al. *Tet. Lett.* 1997, 38, 1497, Chen, Meng-Hsin; Abraham, John A. *Tetrahedron Lett.* 1996, 37, 5233-5234 and Slade, P. D. et al. *J. Med. Chem.* 1998, 41, 1218-1235 or as described by the methods used in the examples or analogues methods.

The reductive alkylation according to method 2 is performed by standard literature methods. Aldehydes or acids of the formula IV can be prepared by methods analogues to those described in e.g. Shuto et al. J. Org. Chem. 1996, 61, 915 and Shuto et al. *J. Med. Chem.* 1996, 38, 2964 and Shuto et al. *J. Chem. Soc., Perkin Trans.* 1, 2002, 1199 and Bonnaud et al. *J. Med. Chem.* 1987, 30, 318. The reaction can be performed in two steps, e.g. coupling of amines of formula III with reagent of formula IV by standard methods via the carboxylic acid chloride, activated esters or by the use of carboxylic acids in combination with a coupling reagents such as e.g. dicyclohexyl carbodiimide, followed by reduction of the resulting amide with lithium aluminium hydride or alane. Alternatively, the reaction can be performed in one step by reductive amination of an aldehyde of formula IV with an amine of formula III according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known and suitable for such reactions.

The acylation of amine VI in method 3 with an ester of formula VII can be performed by methods analogues to those described in the literature e.g. Lesimple et al. *Synthesis* 1991, 306. Amines of formula VI are either commercially available or can be prepared by methods known in the literature according to methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known and suitable for such reactions and esters of fomula VII can be made by methods analogues to those described in the literature e.g. Shuto et al. *J. Org. Chem.* 1996, 61, 915 and Ronsisvalle et al. *Biorg. Med. Chem.* 2000, 8, 1503 and Bonnaud et al. *J. Med. Chem.* 1987, 30, 318.

The acylation of amine VI in method 4 with an acid of formula VIII can be performed by standard methods via the carboxylic acid chloride, activated esters or by the use of carboxylic acids in combination with a coupling reagent such as e.g. dicyclohexyl carbodiimide, carbonyl diimidazole or benzotriazol-1-loxytris(dimethylamino)phosphonium hexafluorophosphate as described in standard works e.g. Bodanszky *"The practice of peptide synthesis"*, 1994 Springer verlag Berlin, ISBN 3-540-57505-7 and Houben-Weyl, Methoden der organischen Chemie (Methods of Organic Chemistry), Georg-Thieme-Verlag, Stuttgart; Organic Reactions, John Wiley & Sons, Inc. New York. The acid of formula VIII can be prepared by standard basic hydrolysis of the ester described in method 3 and in the Examples.

The reduction of amine IX in method 5 can be performed by standard methods e.g. hydrogenate using a Parr apparatus (ambient temperature, 3 atm. $H_2$) and adding a catalyst e.g. Crabtree's catalyst ([(1,5-cyclooctadiene)(pyridine)(tricyclohexylphosphine)iridium(I) hexafluorophosphate]), palladium or platinum oxide. The amine of formula IX can be prepared by the same procedure as described in method 2, using an oxo-alkenyl compound of formula X, which can be prepared by a wittig reaction between an aldehyde of formula IVa and a wittig reagent derived from (1,3-Dioxolan-2-ylmethyl)triphenylphosphonium bromide in the presence of a suitable base.

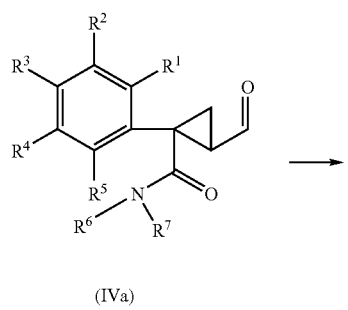

(IVa)

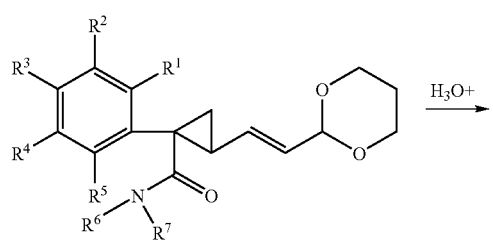

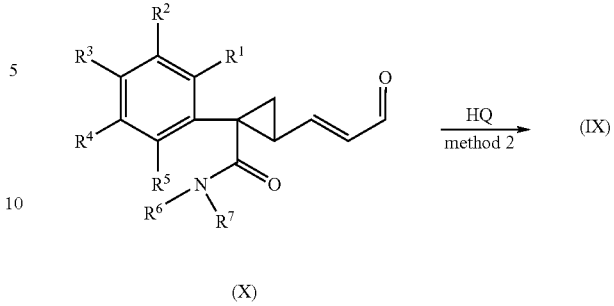

(X)

The invention disclosed herein is further illustrated by the following non-limiting examples.

EXAMPLES

General Methods

Melting points were determined on a Buichi SMP-20 apparatus and are uncorrected. Analytical LC-MS data were obtained on a PE Sciex API 150EX instrument equipped with IonSpray source and Shimadzu LC-8A/SLC-10A LC system. The LC conditions (C18 column 4.6×30 mm with a particle size of 3.5 µm) were linear gradient elution with water/acetonitrile/trifluoroacetic acid (90:10:0.05) to water/acetonitrile/trifluoroacetic acid (10:90:0.03) in 4 min at 2 mL/min. Purity was determined by integration of the UV trace (254 nm). The retention times, $R_t$, are expressed in minutes.

Mass spectra were obtained by an alternating scan method to give molecular weight information. The molecular ion, MH+, was obtained at low orifice voltage (5-20V) and fragmentation at high orifice voltage (100-200V).

Preparative LC-MS-separation was performed on the same instrument. The LC conditions (C18 column 20×50 mm with a particle size of 5 µm) were linear gradient elution with water/acetonitrile/trifluoroacetic acid (80:20:0.05) to water/acetonitrile/trifluoroacetic acid (5:95:0.03) in 7 min at 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated chloroform (99.8% D) or dimethyl sulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet. NMR signals corresponding to acidic protons are generally omitted. For column chromatography silica gel of type Kieselgel 60, 230-400 mesh ASTM was used. For ion-exchange chromatography (SCX, 1 g, Varian Mega Bond Elut®, Chrompack cat. No. 220776) was used. Prior use of the SCX-columns was pre-conditioned with 10% solution of acetic acid in methanol (3 mL).

The enantiomeric purity was measured using capillary electrophoresis. Capillary length 48.5 cm×50 µm I.D. at 30° C. using a fixed current of 80 µA. The buffer used was 25 mM sodium hydrogen phosphate pH 3.0 containing 4% (w/v) sulphated β-cyclodextrin. Detection was done using UV-spectrometer at 192 nm. Sample concentration was 500 µg/ml in methanol and injection was performed by pressure at 50 mbar for 5 seconds.

Alternatively, the enantiomeric purity was measured by chiral HPLC using a Gilson SF3 supercritical fluid chromatography system equipped with chiralcelOD columns (4.6 mm×25 cm for analytical and 10 mm×25 cm for preparative runs). The particle size in the columns was 10 μm. The column was eluted with carbondioxide-modifier (75:25). The modifier was 2-propanol with diethylamine (0.5%) and trifluoroacetic acid (0.5%). The flow was 18.9 mL/min at 20 Mpa. Fraction collection was triggered by UV-detection (210 mM).

Preparation of Intermediates

Example 1

Synthesis of racemic 1-(3,4-Difluorophenyl)-3-oxa-bicyclo[3.1.0]hexan-2-one (3,4-Difluorophenyl)acetic acid (52 g; 0.3 mol) was dissolved in N,N-dimethylformamid (200 mL). Potassium carbonate (61 g, 0.45 mol) was added and the mixture was stirred at room temperature (rt) for 15 min. Allyl bromide (47 g, 0.39 mol) was added and the suspension was stirred at room temperature for 20 h. The mixture was thrown into water (250 mL) and extracted with diethylether (2×300 mL). The combined organic phases were washed with water (4×100 mL), dried (Magnesium sulphate) and evaporated in vacuo to give 64 g (3,4-Difluoro-phenyl)acetic acid allyl ester as a clear oil.

(3,4-Difluoro-phenyl)acetic acid allyl ester (64 g) was dissolved in acetonitrile (400 mL) and 4-acetamidobenzenesulfonyl azide (p-ABSA, 87 g, 0.36 mol) was added and the mixture stirred at room temperature for 15 min. The mixture was then cooled to 0° C. and 1,8-diazabicyclo[5.4.0]undec-7-ene (DBU, 58.6 mL) was added dropwise at 0° C. during 30 min. The mixture was allowed to warm up to rt (room temperature) and stirred at rt for 4-20 h (until TLC showed completion of reaction). Saturated ammonium chloride (500 mL) was added and the organic phase was separated from the water phase. The water phase was extracted with diethylether (3×200 mL) and the four combined organic phases were dried (Magnesium sulphate) and evaporated in vacuo. The resulting solid was extracted with a 50:50 mixture of diethylether/pentane (3×200 mL). The combined ether phases were evaporated in vacuo (keep temperature below 40°) and purified by flash column chromatography (silicagel, eluent: 10:90 mixture of diethylether/pentane). The yellow fractions were combined and evaporated in vacuo (keep temperature below 40°) to give 70 g diazo-(3,4-Difluoro-phenyl)acetic acid allyl ester.

Diazo-(3,4-Difluoro-phenyl)acetic acid allyl ester (70 g) was dissolved in dichloromethane (1000 mL) and added slowly during 36 h via a syringe pump (alternatively it is added dropwise via an addition funnel; 30 mL pr. hour) to a refluxing solution of rhodium (II) octanoate dimer (1.17 g, 1.5 mmol) in dichloromethane (200 mL). After all diazo compound has been added, the mixture is refluxed for another 30 min, then was evaporated in vacuo and crystallised by addition of cyclohexane (200 mL). This gave 30 g crystalline. Further 15 g was isolated from the motherliq. by repeated evaporation and crystallisation giving in total 45 g 1-(3,4-Difluoro-phenyl)-3-oxa-bicyclo[3.1.0]hexan-2-one.

The following compounds were prepared in a similar way:
1-(3,4-dichlorophenyl)-3-oxa-bicyclo[3.1.0]hexan-2-one
1-(4-chlorophenyl)-3-oxa-bicyclo[3.1.0]hexan-2-one
1-(4-fluorophenyl)-3-oxa-bicyclo[3.1.0]hexan-2-one
1-phenyl-3-oxa-bicyclo[3.1.0]hexan-2-one Example 2

Synthesis of (1S,5R)-1-(3,4-Dichlorophenyl)-3-oxa-bicyclo[3.1.0]hexan-2-one

A solution of 3,4-dichlorophenylacetonitrile (62 g, 332 mmol) in benzene (250 mL) was added slowly to a suspension of sodium amide (28.1 g, 720 mmol) in benzene (250 mL) at 0° C. under argon, and the mixture was stirred at room temperature for 3 h. To the resulting mixture, a solution of (R)-epichlorohydrin (30.1 g, 288 mmol] in benzene (250 mL) was added at 0° C. during 45 minutes, and the whole was stirred at room temperature for 16 h. After the solvent was evaporated, EtOH (1250 mL) and 2 N NaOH (500 mL) were added to the residue, and the mixture was heated under reflux for 15 h and then acidified with 12 N HCl at 0° C. (pH of the mixture was about 1). The resulting mixture was evaporated, and AcOEt (900 mL) was added to the residue. Insoluble salts were filtered off, and the filtrate was washed with brine, dried (Na2SO4), and evaporated. The residue was purified by column chromatography (silica gel; AcOEt/heptane, 20:80) to give the product as orange crystals (31.2 g, 39%). mp ° C. $[\alpha]_{20~D}$=−69.5 (c 1.0, MeOH). $^1$H-NMR (500 MHz, DMSO-d$_6$) 1.38(1H, dd), 1.75 (1H, dd,), 2.85 (1H, ddd), 4.25 (1H, d), 4.46(1H, dd), 7.45 (1H, d), 7.65 (1H, d), 7.75 (1H, s), The following compounds were prepared in a similar way:
(1S,5R)-1-(4-chlorophenyl)-3-oxa-bicyclo[3.1.0]hexan-2-one
  (28 g, 41%). mp ° C. $[\alpha]_{20~D}$=−66.1 (c 1.0, MeOH). $^1$H-NMR (500 MHz, CDCl$_3$) 1.35 (1H, dd), 1.60 (1H, dd,), 2.55 (1H, ddd), 4.25 (1H, d), 4.40 (1H, dd), 7.30-7.44 (5H, m)
(1S,5R)-1-phenyl-3-oxa-bicyclo[3.1.0]hexan-2-one
  (36 g, 41%). mp 56-57° C. $[\alpha]_{20~D}$=−77.3 (c 1.0, MeOH). $^1$H-NMR (500 MHz, CDCl$_3$) 1.45 (1H, dd), 1.65 (1H, dd,), 2.55 (1H, ddd), 4.30 (1H, d), 4.45 (1H, dd), 7.30-7.44 (5H, m)
(1S,5R)-1-(4-fluorophenyl)-3-oxa-bicyclo[3.1.0]hexan-2-one
  $[\alpha]_{20~D}$=−63.9-(c 1.0, MeOH).
(1S,5R)-1-(3,4-difluorophenyl-3-oxa-bicyclo[3.1.0]hexan-2-one
  $[\alpha]_{20~D}$-55.7 (c 1.0, MeOH).
(1S,5R)-1-(4-methylphenyl)-3-oxa-bicyclo[3.1.0]hexan-2-one
(1S,5R)-1-(4-methoxyphenyl)-3-oxa-bicyclo[3.1.0]hexan-2-one
(1S,5R)-1-(3-fluorophenyl)-3-oxa-bicyclo[3.1.0]hexan-2-one
(1S,5R)-1-(3-chlorophenyl)-3-oxa-bicyclo[3.1.0]hexan-2-one Example 3

(1S,2R)-2-Hydroxymethyl-1-phenyl-cyclopropanecarboxylic acid benzyl-methyl-amide To a solution of (1S,5R)-1-phenyl-3-oxa-bicyclo[3.1.0]hexan-2-one (10.5 g, 60.0 mmol) in CH$_2$Cl$_2$ (200 mL) was added AlCl3 (16.0 g, 120 mmol) and then the mixture was cooled to 0° C., and then benzyl methyl amine (240 mmol, as a 2.0M solution of benzyl methyl amine in THF) was added slowly. The mixture was stirred at room temperature for 24 h, and then the reaction was quenched with saturated aqueous NH4Cl. After addition of CH$_2$Cl$_2$ and H2O, the resulting mixture was partitioned. The organic layer was washed with 1N HCl and brine, dried (Na$_2$SO$_4$), evaporated, and purified by column chromatography (silica gel; AcOEt/hexane, 1:4) to give (1S,2R)-2-Hydroxymethyl-1-phenyl-cyclopropanecarboxylic acid benzyl-methyl-amide.

The following compounds were prepared in a similar way:
(1S,2R)-1-(4-Chlorophenyl)-2-hydroxymethyl-cyclopropanecarboxylic acid benzyl methyl amide;
(1S,2R)-1-(4-Fluorophenyl)-2-hydroxymethyl-cyclopropanecarboxylic acid benzyl methyl amide;
(1S,2R)-1-(3,4-Difluorophenyl)-2-hydroxymethyl-cyclopropanecarboxylic acid benzyl methyl amide;
(1S,2R)-1-(3,4-Dichlorophenyl)-2-hydroxymethyl-cyclopropanecarboxylic acid benzyl methyl amide;
(1S,2R)-2-Hydroxymethyl-1-phenyl-cyclopropanecarboxylic acid methyl(1-phenylethyl)amide;
(1S,2R)-1-(4-Chlorophenyl)-2-hydroxymethyl-cyclopropanecarboxylic acid methyl(1-phenylethyl)amide;
(1S,2R)-1-(4-Fluorophenyl)-2-hydroxymethyl-cyclopropanecarboxylic acid methyl(1-phenylethyl)amide;
(1S,2R)-1-(3,4-Difluorophenyl)-2-hydroxymethyl-cyclopropanecarboxylic acid methyl(1-phenylethyl)amide;
(1S,2R)-1-(3,4-Dichlorophenyl)-2-hydroxymethyl-cyclopropanecarboxylic acid methyl(1-phenylethyl)amide;
(1S,2R)-2-Hydroxymethyl-1-phenyl-cyclopropanecarboxylic acid (4-fluorobenzyl)methyl amide;
(1S,2R)-1-(4-Chlorophenyl)-2-hydroxymethyl-cyclopropanecarboxylic acid (4-fluorobenzyl)methyl amide;
(1S,2R)-1-(4-Fluorophenyl)-2-hydroxymethyl-cyclopropanecarboxylic acid (4-fluorobenzyl)methyl amide;
(1S,2R)-1-(3,4-Difluorophenyl)-2-hydroxymethyl-cyclopropanecarboxylic acid (4-fluorobenzyl)methyl amide;
(1S,2R)-1-(3,4-Dichlorophenyl)-2-hydroxymethyl-cyclopropanecarboxylic acid (4-fluorobenzyl)methyl amide;
(1S,2R)-2-Hydroxymethyl-1-phenyl-cyclopropanecarboxylic acid (2-chlorobenzyl)methyl amide;
(1S,2R)-1-(4-Chlorophenyl)-2-hydroxymethyl-cyclopropanecarboxylic acid (2-chlorobenzyl)methyl amide;
(1S,2R)-1-(4-Fluorophenyl)-2-hydroxymethyl-cyclopropanecarboxylic acid (2-chlorobenzyl)methyl amide;
(1S,2R)-1-(3,4-Difluorophenyl)-2-hydroxymethyl-cyclopropanecarboxylic acid (2-chlorobenzyl)methyl amide;
(1S,2R)-1-(3,4-Dichlorophenyl)-2-hydroxymethyl-cyclopropanecarboxylic acid (2-chlorobenzyl)methyl amide.

Example 4

Esters of the Formula VII (1S,5R)-1-(3,4-Dichlorophenyl)-3-oxa-bicyclo[3.1.0]hexan-2-one (22.6 g) was dissolved in 33% HBr/glacial acetic acid and heated to 80° C. for 5 h, cooled to rt and thrown into 1300 ml ice-water and stirred at rt for 16 h. The precipitated acid was isolated by filtration, redissolved in toluene (1000 ml), dried over anhydrous magnesium sulphate and evaporated in vacuo to give 30 g of the intermediate (1S,2R)-2-(bromomethyl)-1-(3,4-dichlorophenyl)cyclopropanecarboxylic acid. The (1S,2R)-2-(bromomethyl)-1-(3,4-dichlorophenyl)cyclopropanecarboxylic acid (30 g) was dissolved in anhydrous toluene (200 ml) and thionylchloride (18 ml) was added dropwise during 15 min. after which the mixture was refluxed for 60 min. The reaction mixture was cooled to 5° C. and methanol (200 ml) was added and the mixture was allowed to warm to rt and stirred at rt for 2 h. The mixture was evaporated in vacuo, redissolved in diethylether, washed with saturated aqueous sodium hydrogen carbonate 25 ml), brine (25 ml), dried over anhydrous magnesium sulphate and evaporated in vacuo. To give the intermediate (1S,2R)-2-(bromomethyl)-1-(3,4-dichlorophenyl)cyclopropanecarboxylic acid methyl ester (27 g). The (1S,2R)-2-(bromomethyl)-1-(3,4-dichlorophenyl)cyclopropanecarboxylic acid methyl ester (15 mmol) was dissolved in acetonitrile (50 ml) and added to a mixture an amine of formula III (15 mmol) in a mixture of acetonitrile (50 ml) and ethyl diisopropylamine (30 mmol). The mixture was stirred at room temperature for 16 h, evaporated in vacuo, taken up in ethyl acetate (200 ml) and washed successively with saturated sodium hydrogen carbonate (50 ml) and brine (50 ml, dried over anhydrous magnesium sulphate and evaporated in vacuo to give the crude product ester of formula VII. Esters of formula VII were generally purified by precipitation of the oxalate salt from acetone.

Other esters of formula VII could be prepared by this method by using the appropriately substituted (1S,5R)-1-aryl-3-oxa-bicyclo[3.1.0]hexan-2-one and amine of formula III.

Example 5

Acids of the Formula VIII

The oxalate salt of (1S,2R)-2-(4-Acetylamino-4-phenyl-piperidin-1-ylmethyl)-1-(3,4-dichlorophenyl)cyclopropanecarboxylic acid methyl ester (10 mmol) was dissolved in methanol (80 mL) and water (20 ml). Lithium hydroxide (50 mmol) was added and the mixture was heated to reflux for 2 h. The mixture was cooled to rt and acidified to pH 3 with concentrated hydrochloric acid and the precipitated product (1S,2R)-2-(4-Acetylamino-4-phenyl-piperidin-1-ylmethyl)-1-(3,4-dichlorophenyl)cyclopropanecarboxylic acid hydrochloride was isolated by filtration and dried in vacuo.

Other acids of formula VIII could be prepared by this method by using the appropriately substituted esters of formula VII.

Example 6

Piperidines of the Formula III

The spiropiperidine-derivatives HQ of formula (vii), wherein X is oxygen, Z is CR$^{27}$R$^{28}$, Y is a bond, i.e. spiro[isobenzofuran-[(3H),4'-piperidines] are prepared according to the methods described by Marxer et al. *J. Org. Chem.* 1975, 40, 1427, by Parham et al. *J. Org. Chem.* 1976, 41, 2628 and by Bauer et al. *J. Med. Chem.* 1976, 19, 1315.

The following compounds were prepared in a similar way:
6-Fluorospiro[isobenzofuran-1(3H),4'-piperidine],
6-trifluoromethylspiro[isobenzofuran-1(3H),4'-piperidine],
6-fluoro-3-methylspiro[isobenzofuran-1(3H),4'-piperidine],
6-trifluoromethyl-3-methylspiro[isobenzofuran-1(3H),4'-piperidine],
5-methylspiro[isobenzofuran-1(3H),4'-piperidine],
6-fluoro-3-isobutylspiro[isobenzofuran-1(3H),4'-piperidine],
6-fluoro-3-cyclohexylspiro[isobenzofuran-1(3H),4'-piperidine] and
6-fluoro-3-(4-fluorophenyl)spiro[isobenzofuran-1(3H),4'-piperidine]

The spiropiperidine-derivatives HQ of formula (vii), wherein X is CR$^{27}$R$^{28}$, Z is NR$^{26}$, Y is a bond are prepared according to the methods described by Maligres et al. *Tetrahedron* 1997, 53, 10983, and by Cheng et al. *Tet. Lett.* 1997, 38, 1497.

The following compounds were prepared in a similar way:
1-Acetyl-5-fluoro-spiro[2,3-dihydro-1H-indol-3,4'-piperidine];
1-Acetyl-spiro[2,3-dihydro-1H-indol-3,4'-piperidine];
1-Methanesulphonyl-spiro[2,3-dihydro-1H-indol-3,4'-piperidine].

The spiropiperidine-derivatives HQ of formula (vii), wherein the X is $CR^{27}R^{28}$, Z is oxygen, Y is a bond, i.e. 2,3-dihydro-spiro(benzofuran-3,4'-piperidines), are prepared according to the methods described by Chen, Meng-Hsin; Abraham, John A. *Tetrahedron Lett.* 1996, 37, 5233-5234 and Slade, P. D. et al. *J. Med. Chem.* 1998, 41, 1218-1235.

The following compounds were prepared in a similar way: 2,3-Dihydro-5-fluorospiro[benzofuran-3,4'-piperidine] and 2,3-dihydro-5,6-difluorospiro[benzofuran-3,4'-piperidine]

The substituents $R^{33}$-$R^{36}$ are introduced by applying suitably substituted starting compounds to methods analogous to the above mentioned.

Example 7

1-(tert-butoxycarbonyl)-4-isocyanato-4-phenyl-piperidine

Triethylamine (5.02 mL, 36.1 mmol) and diphenylphosphoryl azide (4.24 mL, 19.7 mmol) are added to a solution of 1-(tert-butoxycarbonyl)-4-phenyl-4-piperidinecarboxylic acid (5.0 g, 16.4 mmol) in dry DMF (50 mL) under nitrogen at ambient temperature. The mixture is stirred at ambient temperature for 2 h, and then heated to 60° C. for 3 h. The mixture is slightly cooled and concentrated in vacuo. Water (75 mL) is added to the remanence followed by extraction with ethyl acetate (2×75 mL). Combined organic fractions are washed with brine (3×50 mL), dried ($MgSO_4$) and evaporated to dryness. The crude mixture is purified by silica gel chromatography eluting with ethyl acetate-heptane (1:4). This furnishes 4.8 g (98%) of the wanted 1-(tert-butoxycarbonyl)-4-isocyanato-4-phenyl-piperidine as a clear oil. LC/MS (m/z) 203.2 (M-boc+$H^+$); $t_R$=3.64 min. $^1$H NMR ($CDCl_3$) 1.49 (s, 9H); 1.92 (bd, 2H); 2.02 (dt, 2H); 3.15 (bt, 2H); 4.17 (bs, 2H); 7.26 (dd, 1H); 7.39 (dt, 2H); 7.44 (dd, 2H).

Example 8

Piperidines of formula III where Q is (iii), and $R^{12}$ is phenyl and $R^{13}$ is a group —$NHCONR^{20}R^{21}$ 1-(tert-butoxycarbonyl)-4-isocyanato-4-phenyl-piperidine (1 mmol) was dissolved in anhydrous THF and an amine $HNR^{20}R^{21}$ (1 mmol) was added, the mixture was stirred at rt for 16 h, evaporated in vacuo and redissolved in a 50:50 mixture of dichloromethane and trifluoroacetic acid (10 ml) and stirred at rt for 60 min. The mixture was evaporated in vacuo to give the product piperidine as the trifluoroacetic acid salt.

Example 9

Piperidines of formula III where Q is (iii), and $R^{12}$ is phenyl and $R^{13}$ is H N-(4-Fluoro-2-piperidin-4-yl-phenyl)-acetamide hydrochloride 2-Bromo-4-fluoro-acetanilide (3.00 g, 12.9 mmol) and pyridine-4-boronic acid (1.60 g, 12.9 mmol) are dissolved in 1,2-dimethoxyethane (70 ml).
Tetrakis(triphenylphosphine)palladium(0) (0.89 g, 0.77 mmol) is added followed by sodium carbonate (4.10 g, 38.7 mmol) dissolved in water (25 ml). The mixture is heated at reflux for 3 hours, then stirred at ambient temperature overnight. Solvents are evaporated in vacuo, then ethyl acetate (50 ml) and aqueous ammonia (dil.) are added to the remanence. The phases are separated and the aqueous layer is extracted with ethyl acetate (2×50 ml). The combined organic fractions are washed with brine (sat.), dried ($MgSO_4$), filtered and concentrated by means of evaporation. The product is purified by silica gel chromatography eluting with ethyl acetate:heptane:triethylamine (70:30:4) followed by ethyl acetate:ethanol:triethylamine (90:10:4) to furnish 2.37 g (80%) of the title compound as an oil. LC/MS (m/z) 231.0 (M+$H^+$). $^1$H NMR ($CDCl_3$): 2.03 (t, 3H); 6.99 (dd, 1H); 7.11 (dt, 1H); 7.28 (dd, 2H); 7.65 (b, 1H, NH); 7.87 (dd, 1H); 8.62 (dd, 2H).

N-(4-Fluoro-2-pyridin-4-yl-phenyl)-acetamide (2.37 g, 10.3 mmol) is dissolved in methanol (40 ml), then platinum oxide (0.2 g, 0.88 mmol) and glacial acetic acid (10 ml) are added. The mixture is hydrogenated at a Parr apparatus (ambient temperature, 3 atm. $H_2$) for 24 hours. The catalyst is removed by filtering through celite and the mixture is concentrated in vacuo. The remanence is redissolved in ethyl acetate (40 ml) and a small amount of water (10 ml) is added. The aqueous phase is made basic by addition of 2M NaOH and the layers are separated. The aqueous phase is extracted again with ethyl acetate (2×30 ml), then the combined organic fractions are washed with brine (sat.), dried ($MgSO_4$), filtered and concentrated in vacuo. The hydrochloride salt is prepared by addition of ethereal HCl to a solution of the crude product in acetone. Precipitated material is filtered off and dried in vacuo to furnish 1.20 g (49%) of the title compound as a white crystalline material. LC/MS (m/z) 237.0 (M+$H^+$). $^1$H NMR (DMSO-$d_6$): 1.82 (m, 4H); 2.07 (s, 3H); 2.95 (m, 2H); 3.03 (m, 1H); 3.36 (m, 2H); 7.00 (dd, 1H); 7.05 (dd, 1H); 7.28 (dd, 1H); 8.75-8.91 (bd, 1H, NH, HCl); 9.48 (s, 1H, NH).

Example 10

(4-Phenyl-piperidine-4-yl)-piperidin-1-yl-methanone

Under a stream of nitrogen N,N'-carbonyldiimidazole (3.62 g, 22.3 mmol) followed by piperidine (3.74 g, 43.9 mmol) is added to a solution of 1-(tert-butoxycarbonyl)-4-phenyl-4-piperidinecarboxylic acid (3.40 g, 11.1 mmol) in dry THF (50 mL). The mixture is heated to reflux 18 h, then cooled to ambient temperature and concentrated by means of evaporation. The remanence is redissolved in ethyl acetate (150 mL) and successively washed with $NaHCO_3$ (50 mL, aq, sat.), dilute HCl (50 mL) at pH 3, brine (50 mL), then dried ($MgSO_4$) and evaporated to dryness. This intermediate is purified by silica gel chromatography eluting with ethyl acetate-heptane-triethylamine (40:50:10) to furnish 1.01 g (24%) of 4-phenyl-4-(piperidine-1-carbonyl)-piperidine-1-carboxylic acid tert-butyl ester as a white crystalline solid. This is dissolved in a mixture of MeOH (10 mL) and THF (10 mL), then 2M HCl in MeOH (5 mL) is added and the mixture is stirred at ambient temperature for 2 h. Water (20 mL) is added and pH is adjusted to pH 12 by addition of 2M NaOH. The organic phase is separated and the aqueous phase is extracted with ethyl acetate (30 mL). Combined organic fractions are dried ($MgSO_4$) and concentrated in vacuo to furnish 0.47 g (63%) of (4-Phenyl-piperidine-4-yl)-piperidin-1-yl-methanone. LC/MS (m/z) 273.1 (M+$H^+$); $t_R$=1.65 mm.

Example 11

Piperidines of formula III where Q is (iii), and $R^{12}$ is phenyl and $R^{13}$ is a group —$CONR^{25}R^{26}$ These piperidines were prepared by the method used in Example 9 using the appropriate amine $HNR^{25}R^{26}$.

Example 12

Piperidines of formula III where Q is (iii), and $R^{12}$ is phenyl and $R^{13}$ is a group —$NR^{14}COR^{15}$ 1-Benzyl-4-phenyl-piperidin-4-ylamine (*Bioorg. Med. Chem. Lett.* 1996; 2307; *Collect. Czech. Chem. Commun.* 1987; 52, 2095; *Synthesis* 2000, 1709) (1 mmol) was dissolved in a mixture of anhydrous acetonitrile and ethyl diisopropylamine (1 mmol). An acid chloride $ClCOR^{15}$ (1 mmol) was added at 0° C. and the mixture was stirred at 0° for 60 min. The mixture was evaporated in vacuo, taken up in ethyl acetate (50 ml), washed with saturated aqueous sodium hydrogen carbonate 25 ml), brine (25 ml), dried over anhydrous magnesium sulphate and evaporated in vacuo. The crude product was taken up in ethanol (50 ml), 5% palladium on charcoal (50 mg) was added and the mixture was hydrogenated for 24 h at 3 bar in a Parr hydrogenation apparatus. The mixture was filtrated and evaporated in vacuo to give the final piperidines.

Example 13

Piperidines of formula III where Q is (iii), and $R^{12}$ is phenyl and $R^{13}$ is a group —$NR^{16}COCONR^{17}R^{18}$ 1-Benzyl-4-phenyl-piperidin-4-ylamine (*Bioorg. Med. Chem. Lett.* 1996; 2307; *Collect. Czech. Chem. Commun.* 1987; 52, 2095; *Synthesis* 2000, 1709) (1 mmol) was dissolved in a mixture of anhydrous acetonitrile and ethyl diisopropylamine (1 mmol). An acid chloride $ClCOCONR^{17}R^{18}$ (1 mmol) was added at 0° C. and the mixture was stirred at 0° for 60 min. The mixture was evaporated in vacuo, taken up in ethyl acetate (50 ml), washed with saturated aqueous sodium hydrogen carbonate 25 ml), brine (25 ml), dried over anhydrous magnesium sulphate and evaporated in vacuo. The crude product was taken up in ethanol (50 ml), 5% palladium on charcoal (50 mg) was added and the mixture was hydrogenated for 24 h at 3 bar in a Parr hydrogenation apparatus. The mixture was filtrated and evaporated in vacuo to give the final piperidines.

Example 14

Piperidines of formula III where Q is (iii), and $R^{12}$ is phenyl and $R^{13}$ is a group —$NR^{22}SO_2R^{23}$ 1-Benzyl-4-phenyl-piperidin-4-ylamine (*Bioorg. Med. Chem. Lett.* 1996; 2307; *Collect. Czech. Chem. Commun.* 1987; 52, 2095; *Synthesis* 2000, 1709) (1 mmol) was dissolved in a mixture of anhydrous acetonitrile and ethyl diisopropylamine (1 mmol). A sulphonyl chloride $ClSO_2R^{23}$ (1 mmol) was added at 0° C. and the mixture was stirred at 0° for 60 min. The mixture was evaporated in vacuo, taken up in ethyl acetate (50 ml), washed with saturated aqueous sodium hydrogen carbonate 25 ml), brine (25 ml), dried over anhydrous magnesium sulphate and evaporated in vacuo. The crude product was taken up in ethanol (50 ml), 5% palladium on charcoal (50 mg) was added and the mixture was hydrogenated for 24 h at 3 bar in a Parr hydrogenation apparatus. The mixture was filtrated and evaporated in vacuo to give the final piperidines.

Example 15

Aldehyde Reagent of Formula IV

For n=0: (1S,2R)-1-(3,4-Dichloro-phenyl)-2-formyl-cyclopropanecarboxylic acid (4-fluoro-benzyl)-methyl-amide (1S,2R)-1-(3,4-Dichloro-phenyl)-2-hydroxymethyl-cyclopropanecarboxylic acid (4-fluoro-benzyl)-methyl-amide (4.60 g, 12.0 mmol) is dissolved in acetone (240 ml) and IBX (10.1 g, 36.1 mmol) is added (IBX concentration 0.15M). The mixture is heated to reflux for 2 hours, then cooled to ambient temperature. The solids are filtered off and the filtrate concentrated in vacuo. The crude product is eluted through a short silica gel column with ethyl acetate:heptane (50:50). 3.57 g (78%) of the product is obtained as a highly viscous light yellow oil. LC/MS (m/z) 380.0 (M+H$^+$).

For n=2: (1S,2S)-1-(3,4-Dichloro-phenyl)-2-((E)-3-oxo-propenyl)-cyclopropanecarboxylic acid (4-fluoro-benzyl)-methyl-amide The isomer mixture (1S,2S)-1-(3,4-dichloro-phenyl)-2-((Z/E)-2-[1,3]dioxolan-2-yl-vinyl)-cyclopropanecarboxylic acid (4-fluoro-benzyl)-methyl-amide (845 mg, 1.88 mmol) is dissolved in acetone (20 ml), p'-toluenesulphonic acid (162 mg, 0.94 mmol) is added and the mixture is stirred at ambient temperature for 1.5 hours. The solvent is removed by means of evaporation and the crude mixture is purified by silica gel chromatography eluting with ethyl acetate:heptane (40:60) to obtain the wanted product as an oil. Yield 480 mg, 63%). LC/MS (m/z) 406.0 (M+H$^+$).

Example 16

Alkylating Reagents of Formula II

For n=0: A suitable substituted (1S,2R)-2-hydroxymethyl-1-phenyl-cyclopropanecarboxylic acid amide (with $R^1$-$R^{36}$ and n as defined herein prepared as described in example 3) (1 mmol) was dissolved in dichloromethane (20 ml) and phosphorus tribromide (3 mmol) was added and the mixture stirred at rt for 3 h. Water (10 ml) was added and after stirring for 10 minutes the dichloromethane phase was isolated, dried over anhydrous magnesium sulphate and evaporated in vacuo to a clear oil which was used immediately without further purification For n=1: (1S,2S)-2-(2-Chloro-ethyl)-1-(3,4-dichloro-phenyl)-cyclopropanecarboxylic acid (4-fluoro-benzyl)-methyl-amide (1S,2R)-1-(3,4-Dichloro-phenyl)-2-hydroxymethyl-cyclopropanecarboxylic acid (4-fluoro-benzyl)-methyl-amide (4.60 g, 12.0 mmol) is dissolved in acetone (240 ml) and IBX (10.1 g, 36.1 mmol) is added (IBX concentration 0.15M). The mixture is heated to reflux for 2 hours, then cooled to ambient temperature. The solids are filtered off and the filtrate concentrated in vacuo. The crude product is eluted through a short silica gel column with ethyl acetate:heptane (50:50).

3.57 g (78%) of the product is obtained as a highly viscous light yellow oil. LC/MS (m/z) 380.0 (M+H$^+$).

Cloromethyltriphenylphosphonium chloride (2.74 g, 7.89 mmol) is suspended in dry THF (30 ml) under Argon and KHMDS (1.57 g, 7.89 mmol) is added portionwise at 0° C. The mixture is stirred at 0° C. for 30 minutes, then allowed to warm to ambient temperature. (1S,2R)-1-(3,4-Dichloro-phenyl)-2-formyl-cyclopropanecarboxylic acid (4-fluoro-benzyl)-methyl-amide (1.0 g, 2.63 mmol) dissolved in dry THF (10 ml) is added dropwise and the mixture is stirred at ambient temperature for 2.5 hours. The reaction mixture is then poured onto ice cold water (30 ml) and the layers are separated. The aqueous phase is extracted with ethyl acetate (2×30 ml) and the combined organic fractions are washed with brine (sat.), dried (MgSO$_4$), filtered and concentrated in vacuo. The crude product is purified by silica gel chromatography, eluting with a gradient of ethyl acetate:heptane (0:100)-(50:50). The product is isolated as a Z/E isomer mixture. Yield 630 mg (57%). LC/MS (m/z) 412.1 (M+H$^+$).

The isomer mixture (1S,2S)-2-((Z/E)-2-chloro-vinyl)-1-(3,4-dichloro-phenyl)-cyclopropanecarboxylic acid (4-fluoro-benzyl)-methyl-amide (170 mg, 0.41 mmol) is dissolved in dichloromethane (10 ml). N$_2$ is bubbled through the solution for 15 minutes before adding Crabtree's catalyst (66.4 mg, 0.082 mmol, [(1,5-cyclooctadiene)(pyridine)(tricyclohexylphosphine)iridium(I) hexafluorophosphate]). The reaction mixture is hydrogenated at a Parr apparatus (ambient temperature, 3 atm. H$_2$) for 4 hours. The solvent is removed by evaporation and the residue is subjected to silica gel chromatography eluting with ethyl acetate:heptane (20:80). 91 mg (53%) of the title compound is isolated as an oil. LC/MS (m/z) 415.9 (M+H$^+$).

Example 17

(1S,2S)-1-(3,4-Dichloro-phenyl)-2-((Z/E)-2-[1,3] dioxolan-2-yl-vinyl)-cyclopropanecarboxylic acid (4-fluoro-benzyl)-methyl-amide (1,3-Dioxolan-2-ylmethyl)triphenylphosphonium bromide (3.39 g, 7.89 mmol) is suspended in dry THF (50 ml) under Argon and KHMDS (1.57 g, 7.89 mmol) is added portionwise at 0° C. The mixture is stirred at 0° C. for 30 minutes, then allowed to warm to ambient temperature. (1S, 2R)-1-(3,4-Dichloro-phenyl)-2-formyl-cyclopropanecarboxylic acid (4-fluoro-benzyl)-methyl-amide (1.0 g, 2.63 mmol) dissolved in dry THF (10 ml) is added dropwise and the mixture is stirred at ambient temperature for 2 hours. The reaction mixture is then poured onto ice cold water (30 ml) and the layers are separated. The aqueous phase is extracted with ethyl acetate (3×30 ml) and the combined organic fractions are washed with brine (sat.), dried (MgSO$_4$), filtered and concentrated in vacuo. The crude product is purified by silica gel chromatography, eluting with a gradient of ethyl acetate: heptane (20:80)-(50:50). The product is isolated as a Z/E isomer mixture. Yield 1.07 g (91%).
LC/MS (m/z) 450.1 (M+H$^+$).

Example 18

(1S,2S)-2-[(E)-3-(4-Acetylamino-4-phenyl-piperidin-1-yl)-propenyl]-1-(3,4-dichloro-phenyl)-cyclopropanecarboxylic acid (4-fluoro-benzyl)-methyl-amide N-(4-Phenyl-piperidin-4-yl)-acetamide (140 mg, 0.64 mmol) dissolved in ethanol (3 ml) is added to (1S,2S)-1-(3,4-Dichloro-phenyl)-2-((E)-3-oxo-propenyl)-cyclopropanecarboxylic acid (4-fluoro-benzyl)-methyl-amide dissolved in ethanol (5 ml) followed by dropwise addition of sodium cyanoborohydride (1.0M in THF, 1.97 ml, 1.97 mmol) at 0° C. After complete addition the mixture is kept at ambient temperature for 2 hours. The reaction is quenched by addition of sodium bicarbonate (3 ml, sat.) and the ethanol is removed by means of evaporation. Ethyl acetate (30 ml) is added to the remanence. The organic fraction is washed successively with sodium bicarbonate (10 ml, sat.) and brine (10 ml, sat.), dried (MgSO$_4$) and concentrated in vacuo. The residue is purified by silica gel chromatography eluting with ethyl acetate:ethanol:triethylamine (95:0:5)-(90:5:5) to furnish the title compound as an oil. Yield 81 mg (27%). LC/MS (m/z) 610.3 (M+H$^+$).

Example 19

Preparation of the Compounds of the Invention

The compounds of the present invention were prepared by one of two general methods:

Method A: Alkylating a Piperidine of Formula III with an Alkylating Derivative of Formula II:

For n=0: A suitable substituted (1S,2R)-2-hydroxymethyl-1-phenyl-cyclopropanecarboxylic acid amide (1 mmol) was dissolved in dichloromethane (20 ml) and phosphorus tribromide (3 mmol) was added and the mixture stirred at rt for 3 h. Water (10 ml) was added and after stirring for 10 minutes the dichloromethane phase was isolated, dried over anhydrous magnesium sulphate and evaporated in vacuo to a clear oil which was used immediately without further purification by dissolving in anhydrous acetonitile (10 ml) and added to a mixture of a piperidine of formula III (1 mmol), and ethyl diisopropyl amine (1.3 mmol) in acetonitrile (10 mL) and the mixture was heated to 85° C. for 3 h. The mixture was cooled to room temperature and evaporated in vacuo. The product was purified by chromatography either on silicagel using as eluent ethylacetate/triethylamine (99:1) or by purified by HPLC.

Fractions containing the product were pooled and evaporated in vacuo and characterised by HPLC-UV-ELSD-MS. The measured HPLC-retention time, the measured molecular mass and UV- and ELSD-purities are shown in Table 1.

For n=1: (1S,2S)-2-[2-(4-Acetylamino-4-phenyl-piperidin-1-yl)-ethyl]-1-(3,4-dichloro-phenyl)-cyclopropanecarboxylic acid (4-fluoro-benzyl)-methylamide (1S,2S)-2-(2-Chloro-ethyl)-1-(3,4-dichloro-phenyl)-cyclopropanecarboxylic acid (4-fluoro-benzyl)-methyl-amide (91 mg, 0.22 mmol) is dissolved in acetonitrile (10 ml). Potassium iodide (73 mg, 0.44 mmol), potassium carbonate (91 mg, 0.66 mmol) and N-(4-Phenyl-piperidin-4-yl)-acetamide hydrochloride (67 mg, 0.26 mmol) are added. The reaction mixture is heated to reflux for 72 hours, then cooled to ambient temperature and concentrated in vacuo. The remanence is redissolved in ethyl acetate (15 ml), washed with water (10 ml), brine (10 ml), then dried over MgSO$_4$, filtered and concentrated to an oil. The product is filtered through a plug of silica gel eluting with ethyl acetate:heptane:triethylamine (50:50:5) followed by ethyl acetate:ethanol:triethylamine (80:20:5) to furnish 70 mg (54%) of the title compound. LC/MS (m/z) 596.3 (M+H$^+$).

Method B: Reacting an Amine of Formula Vi with an Acid of Formula VIII by the Use of an Activating Reagent or a Coupling Reagent:

(1S,2R)-2-(4-Acetylamino-4-phenyl-piperidin-1-ylmethyl)-1-(3,4-dichlorophenyl)cyclopropanecarboxylic acid hydrochloride (0.05 mmol) was dissolved in anhydrous DMF. Ethyl diisopropylamine (0.15 mmol), benzylamine (0.075 mmol), dimethylaminopyridine (0.05 mmol) and BOP (benzotriazol-1-yloxytris(dimethylamino)phosphonium hexafluorophosphate 0.1 mmol) were added and the mixture stirred at rt for 2 h. The reaction mixture was evaporated in vacuo and the product purified by HPLC. Fractions containing the product were pooled and evaporated in vacuo and characterised by HPLC-UV-ELSD-MS. The measured HPLC-retention time, the measured molecular mass and UV- and ELSD-purities are shown in table 1.

Method C Reducing an Amine of Formula IX:

For n=2: (1S,2R)-2-[3-(4-Acetylamino-4-phenyl-piperidin-1-yl)-propyl]-1-(3,4-dichlorophenyl)-cyclopropanecarboxylic acid (4-fluoro-benzyl)-methyl-amide (1S,2S)-2-[(E)-3-(4-Acetylamino-4-phenyl-piperidin-1-yl)-propenyl]-1-(3,4-dichloro-phenyl)-cyclopropanecarboxylic acid (4-fluoro-benzyl)-methyl-amide (65 mg, 0.11 mmol) is dissolved in dichloromethane (10 ml). $N_2$ is bubbled through the solution for 15 minutes before adding Crabtree's catalyst (17.7 mg, 0.022 mmol, [(1,5-cyclooctadiene)(pyridine)(tricyclohexylphosphine)iridium(I) hexafluorophosphate]). The reaction mixture is hydrogenated at a Parr apparatus (ambient temperature, 3 atm. $H_2$) for 3 hours. The solvent is removed by evaporation and the residue is subjected to silica gel chromatography eluting with ethyl acetate:ethanol:triethylamine (95:0:5)-(85:10:5). Evaporation from heptane furnishes the title compound as a white solid. Yield 25 mg (38%).

LC/MS (m/z) 610.3 (M+H$^+$).

The following compounds were made by the methods indicated in the table. Analytical data are shown in table 1.

| compound | M + H$^+$ | RT min. | UV-purity (%) | ELSD-purity (%) | Synthesis method |
|---|---|---|---|---|---|
| 1a | 564.2 | 2.5 | 98.49 | 97.90 | A |
| 2a | 578.5 | 2.7 | 41.8 | 99.2 | A |
| 3a | 576.3 | 2.6 | 82.5 | 98.3 | A |
| 4a | 594.3 | 2.6 | 98.17 | 98.59 | A |
| 5a | 590.2 | 2.6 | 82.6 | 100 | A |
| 6a | 608.5 | 2.8 | 96.65 | 99.48 | A |
| 7a | 550.2 | 2.5 | 97.87 | 99.93 | A |
| 8a | 544.2 | 2.4 | 82.38 | 99.91 | A |
| 9a | 481.3 | 2.3 | 92.92 | 100 | A |
| 10a | 557.1 | 2.6 | 75.95 | 99.33 | A |
| 12a | 530.2 | 2.2 | 95.68 | 99.83 | A |
| 13a | 584.3 | 2.5 | 97.25 | 99.47 | A |
| 14a | 544.1 | 2.7 | 93.6 | 99.8 | A |
| 15a | 515.2 | 2.4 | 72.36 | 99.83 | A |
| 16a | 542.3 | 2.5 | 88.53 | 100 | A |
| 17a | 560.3 | 2.4 | 98.21 | 99.95 | A |
| 18a | 546.4 | 2.4 | 96.39 | 99.87 | A |
| 19a | 560.3 | 2.3 | 90.62 | 100 | A |
| 20a | 576.4 | 2.4 | 94.47 | 100 | A |
| 21a | 514.2 | 2.4 | 99.42 | 99.84 | A |
| 22a | 528.4 | 2.2 | 96.9 | 99.8 | A |
| 23a | 526.4 | 2.3 | 75.77 | 99.95 | A |
| 24a | 575.1 | 2.2 | 97.43 | 99.74 | A |
| 25a | 544.3 | 2.6 | 90.09 | 99.48 | A |
| 26a | 562 | 2.3 | 96.58 | 99.84 | A |
| 27a | 604.4 | 2.4 | 95.66 | 100 | A |
| 28a | 533.1 | 2.5 | 99.44 | 100 | A |
| 29a | 560.1 | 2.5 | 98.16 | 99.81 | A |
| 30a | 578.2 | 2.4 | 97.01 | 99.87 | A |
| 31a | 586.2 | 2.4 | 97.17 | 100 | A |
| 32a | 562.2 | 2.6 | 91.69 | 99.36 | A |
| 33a | 604.4 | 2.3 | 93.68 | 99.44 | A |
| 34a | 606.5 | 2.6 | 84.9 | 99.19 | A |
| 35a | 580.4 | 2.4 | 96.74 | 98.84 | A |
| 36a | 618.2 | 2.4 | 92.3 | 99.95 | A |
| 37a | 549.2 | 2.8 | 100 | 99.34 | A |
| 38a | 558.3 | 2.6 | 97.21 | 99.97 | A |
| 39a | 578.3 | 2.4 | 99.62 | 98.43 | A |
| 40a | 632.4 | 2.5 | 100 | 99.77 | A |
| 41a | 592.2 | 2.9 | 99.11 | 98.91 | A |
| 42a | 568.5 | 2.5 | 99.3 | 99.97 | A |
| 43a | 602.3 | 2.5 | 87 | 99.68 | A |
| 44a | 548.3 | 2.7 | 94.96 | 99.24 | A |
| 45a | 564.1 | 2.5 | 96.864 | 98.061 | A |
| 46a | 618.2 | 2.4 | 97.35 | 99.74 | A |
| 47a | 580.4 | 2.8 | 93.59 | 98.34 | A |
| 48a | 594.3 | 2.5 | 93.88 | 98.39 | A |
| 49a | 562.2 | 2.5 | 98.65 | 99.69 | A |
| 50a | 580.5 | 2.4 | 94.44 | 99.91 | A |
| 51a | 598 | 2.4 | 92.14 | 99.97 | A |
| 52a | 654.3 | 2.5 | 96.76 | 99.82 | A |
| 53a | 614.1 | 2.8 | 92.98 | 98.17 | A |
| 54a | 610.3 | 2.6 | 100 | 100 | A |
| 55a |  | 2.6 | 99.79 | 99.89 | B |
| 56a |  | 2.7 | 95.24 | 99.87 | B |
| 57a | 614.1 | 2.79 | 100 | 99.96 | A |
| 58a | 610.3 | 2.45 | 58.47 | 99.76 | A |
| 59a |  | 2.51 |  |  | A |
| 60a |  | 2.31 |  |  | A |
| 61a |  | 2.31 |  |  | A |
| 62 a | 579.7 | 2.5 | 58.47 | 99.76 | A |
| 63 a | 593.1 | 2.8 | 43.8 | 99.7 | A |
| 64 a | 591.6 | 2.6 | 93.8 | 99.6 | A |
| 65 a | 609.5 | 2.6 | 96.3 | 99.7 | A |
| 66 a | 496.4 | 2.1 | 97.5 | 100 | A |
| 67 a | 632.6 | 2.9 | 98.56 | 99.24 | A |
| 68 a | 608.4 | 2.6 | 99.22 | 99.37 | A |
| 69 a | 568.3 | 2.5 | 79.36 | 99.97 | A |
| 70 a | 499.3 | 2.4 | 96.75 | 99.88 | A |
| 71 a | 580.1 | 2.4 | 72.93 | 99.12 | A |
| 72 a | 546.4 | 2.3 | 72.08 | 99.94 | A |
| 73 a | 517.2 | 2.4 | 99.56 | 99.88 | A |
| 74 a | 544.2 | 2.3 | 95.31 | 99.94 | A |
| 75 a | 535.2 | 2.4 | 87.78 | 98.21 | A |
| 76 a | 561.9 | 2.3 | 85.12 | 99.62 | A |
| 77 a | 582.5 | 2.6 | 98.18 | 99.36 | A |
| 78 a | 549.3 | 2.6 | 95.56 | 99.92 | A |
| 79 a | 576.3 | 2.4 | 99.76 | 99.77 | A |
| 80 a | 548.3 | 2.3 | 97.01 | 99.9 | A |
| 81 a | 602.3 | 2.6 | 91.01 | 98.89 | A |
| 82 a | 566.3 | 2.3 | 96.79 | 99.89 | A |
| 83 a | 620.3 | 2.7 | 96.06 | 98.97 | A |
| 84 a | 578.3 | 2.4 | 99.48 | 99.97 | A |
| 85 a | 596.2 | 2.4 | 98.72 | 99.64 | A |
| 86 a | 563 | 2.8 | 75.93 | 99.76 | B |
| 87 a | 553.3 | 2.4 | 100 | 99.92 | B |
| 88 a | 536.1 | 1.9 | 97.04 | 97.15 | B |
| 89 a | 578.2 | 2.1 | 98.94 | 98.53 | B |
| 90 a | 508.1 | 0.3 | 100 | 97.06 | A |
| 91 a | 506.2 | 2.2 | 100 | 96.9 | A |
| 92 a | 560.3 | 2.8 | 100 | 95.22 | A |
| 93 a | 488.4 | 0.2 | 100 | 94.2 | A |
| 94 a | 454.3 | 2.0 | 100 | 93.98 | A |
| 95 a | 542.3 | 2.8 | 100 | 90.31 | A |
| 96 a | 526.4 | 2.67 | 99.68 | 94.67 | A |
| 97 a | 550.2 | 2.4 | 75.05 | 100 | B |
| 98 a | 598.2 | 2.5 | 94.43 | 100 | B |
| 99 a | 608.5 | 2.6 | 72 | 99.96 | B |
| 100 a | 586.3 | 2.4 | 85.68 | 100 | B |
| 101 a | 620.2 | 2.6 | 76.84 | 100 | B |
| 102 a | 550.2 | 2.4 | 81.65 | 96.17 | B |

-continued

| compound | M + H+ | RT min. | UV-purity (%) | ELSD-purity (%) | Synthesis method |
|---|---|---|---|---|---|
| 103 a | | 2.3 | 79.033 | 95.204 | A |
| 104 a | | 2.5 | 96.808 | 99.264 | A |
| 105 a | | 2.4 | 89.646 | 99.617 | A |
| 106 a | | 2.4 | 100 | 97.591 | A |
| 107 a | | 2.3 | 91.596 | 99.140 | A |
| 108 a | | 2.3 | 89.427 | 99.205 | A |
| 109 a | | 2.4 | 90.019 | 99.287 | A |
| 110 a | | 2.2 | 83.676 | 99.134 | A |
| 111 a | 515.3 | 2.2 | 100.0 | 96.5 | A |
| 112 a | 565.1 | 2.5 | 88.545 | 92.457 | A |
| 113 a | 529.3 | 2.2 | 93.664 | 99.867 | A |
| 114 a | 581.2 | 2.5 | 96.751 | 99.232 | B |
| 115 a | 543.3 | 2.3 | 95.946 | 98.700 | B |
| 116 a | 593.1 | 2.6 | 95.664 | 99.544 | A |
| 117 a | 550.2 | 2.4 | 80.435 | 98.991 | A |
| 118 a | 602.2 | 2.6 | 85.679 | 99.662 | A |
| 119 a | 530 | 2.5 | 86.245 | 98.629 | A |
| 120 a | 580.4 | 2.6 | 79.450 | 99.148 | A |
| 121 a | 593.2 | 2.6 | 78.272 | 98.414 | A |
| 122 a | 543.3 | 2.4 | 98.860 | 98.734 | A |
| 123 a | 596.3 | 2.4 | 77.0 | 99.2 | A |
| 124 a | 610.3 | 2.5 | 82.4 | 98.8 | C |
| 125 a | 600.2 | 2.5 | 73.000 | 98.462 | B |
| 126 a | 542.4 | 2.5 | 90.187 | 98.575 | A |
| 127 a | 582.3 | 2.5 | 100 | 96.845 | A |
| 128 a | 519.9 | 2.3 | 84.144 | 95.282 | A |
| 129 a | 532.3 | 2.3 | 80.554 | 99.653 | A |
| 130 a | 557.2 | 2.4 | 100 | 97.176 | B |
| 131 a | 644.3 | 2.3 | 84.144 | 95.282 | B |
| 132 a | 614.3 | 2.3 | 80.554 | 99.653 | B |

Example 20

Receptor Binding Assay (Ki)

The binding assay is based on previously described methods (Chung F Z et al: Mol Pharmacol. 1995 48 p 711-6 and Sarau H M et al: J Pharmacol Exp Ther. 1997 281 p 1303-11).

Membrane Preparation

Membranes were isolated from baby hamster kidney (BHK) cells stably expressing the human NK1 or NK3 receptors or from Chinese hamster ovary (CHO) cells stably expressing the human NK2 receptor. 24 hours before harvesting, the BHK cells were treated with trichostatin A (TSA) to increase expression. The cells were washed twice with ice-cold phosphate-buffered saline without $Mg^{2+}$, $Ca^{2+}$ and Sodium bicarbonate (PBS). The cells were scraped of in 10 ml PBS and centrifuged for 3 min at 4° C. and 1500 g. The supernatant was discarded and the pellet was resuspended in 10 ml of 15 mM Tris-HCl pH 7.5 buffer containing 2 mM $MgCl_2$, 0.3 mM EDTA, 1 mM EGTA (buffer A) and subsequently Dounce homogenised. (For the NK1 receptor containing membranes an extra step with 5 min centrifugation at 4° C. and 1500 g followed by resuspension of the pellet in 10 ml buffer A was included to enrich the membrane preparation). The suspension was centrifuged for 25 min at 4° C. and 40000 g. The supernatant was discarded, the pellet was washed with 10 ml buffer A and the suspension was centrifuged for 25 min at 4° C. and 40000 g. The supernatant was discarded and the pellet was resuspended in 7.5 mM Tris-HCl pH 7.5 containing 12.5 mM $MgCl_2$, 0.3 mM EDTA, 1 mM EGTA and 250 nM sucrose, frozen in liquid nitrogen and stored at −80° C.

Competition Binding Assay

For the NK3 binding assay, membranes were incubated with 0.1 nM $^{125}$I-eledoisin in 50 mM Tris pH 7.4 buffer containing 3 mM $MnCl_2$, 40 µg/ml bacitracin, 21 g/ml chymostatin, 2 µM phosphoramidon, 4 µg/ml leupeptin, 0.02% bovine serum albumin (BSA) and selected concentrations of compounds for 60 min at 25° C.

For the NK1 and NK2 binding assay, the membranes were incubated with 0.1 nM 125 I-substance P or 0.1 nM 125I-NKA, respectively in 50 mM Tris pH 7.4 buffer containing 3 mM $MnCl_2$ and 0.02% BSA and selected concentrations of compounds for 60 min at 25° C. The assay was terminated by rapid filtration through GF/C UniFilters presoaked with 1% BSA (NK3 binding assay) or 0.1% polyethyleneimine (NK1 and NK2 binding assays) using a Tomtec harvester. The filters were washed 3 times with ice-cold 50 mM Tris pH 7.4, dried and added scintillant before counting in a Wallac scintillation counter.

For each compound, the $IC_{50}$ value (the concentration required to obtain 50% inhibition of the radioligand) was determined from concentration-response curves and used to calculate the apparent affinity $K_i$ from the equation $K_i=IC_{50}/(1+L/K_d)$, where L is the concentration of radioligand. $K_d$ is the dissociation constant of the radioligand and was determined from saturation binding experiments.

When tested as described above the compounds 1a-56a all had an apparent NK3 affinity (Ki) of less than 50 nM, the compounds 57a-64a all had an apparent NK3 affinity (Ki) of less than 1000 nM, the compounds 65a-85a all had an apparent NK3 affinity (Ki) of less than 200 nM and the compounds 86a-132a all had an apparent NK3 affinity (Ki) of less than 1000 nM.

Example 21

The Fluorometric Imaging Plate Reader (FLIPR) assay: The compounds were analysed for efficacy profile in FLIPR assays similar to assays described in Jerman, J C et al: Eur J Pharmacol. 2001, 414, p 23-30. BHK cells (cf. Example 20) stably expressing the human NK3 receptor were seeded in 100 µl media in black walled clear-base 96-wells plates (Costar) aiming at a confluency of 95-100% at the day of assay. The assay was performed according to the calcium assay kit (Molecular Devices). Briefly, the calcium assay reagent was dissolved in Hanks BSS (HBSS) buffer, pH 7.4 containing 20 mM Hepes and 2.5 mM probinicid. An equal volume (100 µl) of the calcium assay reagent solution was added to the wells and the plates were incubated for 60 min at 37° C. The plates were subsequently placed in the FLIPR for examination of fluorescence.

Compounds were diluted in HBSS buffer containing 20 mM Hepes prior to test. For test of agonist activity 50 µl of compound was added to the wells and the plates were analysed for 3 minutes in the FLIPR. For test of antagonist activity, 25 µl of compound was added to the wells and the plate was analysed for a 5 minute period. Subsequently, the wells were added 25 µl of an $EC_{85}$ (final concentration) of NKB (app. 1 nM) previously determined from a dose-response curve with NKB. The plates were subsequently read for 3 minutes before termination. As controls, selected wells on all plates were added only 100 nM of the NK3 receptor agonist NKB or 2 µM of the calcium ionophor ionomycin. The maximal increase in fluorescence over background following each ligand addition was determined and analysed.

Compounds 1a-7a, 11a-21a, 23a, 25a, 27a-30a, 32a, 33a, 35a-39a, 42a, 44a, 45a, 51a-53a, 62a, 63a were tested in the FLIPR assay described above and inhibited the NKB-mediated activation of the NK3 receptor expressed in the BHK cells. The results showed that the compounds are NK3 receptor antagonists.

The invention claimed is:

1. A compound of formula I

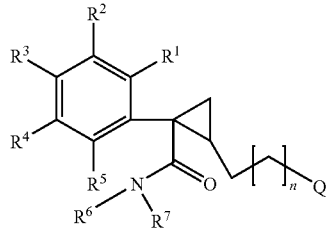

wherein

R¹-R⁵ are independently selected from the group consisting of hydrogen, halogen, cyano, nitro, $C_{1-6}$-alk(en/yn)yl, $C_{3-8}$-cycloalk(en)yl, $C_{3-8}$-cycloalk(en)yl-$C_{1-6}$-alk(en/yn)yl, amino, $C_{1-6}$-alk(en/yn)ylamino, di-($C_{1-6}$-alk(en/yn)yl)amino, $C_{1-6}$-alk(en/yn)ylcarbonyl, aminocarbonyl, $C_{1-6}$-alk(en/yn)ylaminocarbonyl, di-($C_{1-6}$-alk(en)yl)aminocarbonyl, hydroxy, $C_{1-6}$-alk(en/yn)yloxy, $C_{1-6}$-alk(en/yn)ylthio, halo-$C_{1-6}$-alk(en/yn)yl, halo-$C_{1-6}$-alk(en/yn)ylsulfonyl, halo-$C_{1-6}$-alk(en/yn)ylsulfanyl, and $C_{1-6}$-alk(en/yn)ylsulfonyl;

R⁶ is selected from the group consisting of hydrogen, halo-$C_{1-6}$-alk(en/yn)yl, $C_{1-6}$-alk(en/yn)yl, $C_{3-8}$-cycloalk(en)yl, and $C_{3-8}$-cycloalk(en)yl-$C_{1-6}$-alk(en/yn)yl;

R⁷ is an aryl or a heteroaryl; or R⁷ is a group aryl-CR⁸R⁹—, wherein R⁸ and R⁹ are independently selected from the group consisting of hydrogen, $C_{1-6}$-alk(en/yn)yl, $C_{3-8}$-cycloalk(en)yl, and $C_{3-8}$-cycloalk(en)yl-$C_{1-6}$-alk(en/yn)yl;

n is 0, 1, or 2;

Q is selected from (i)-(vii), the arrow indicating the attachment point:

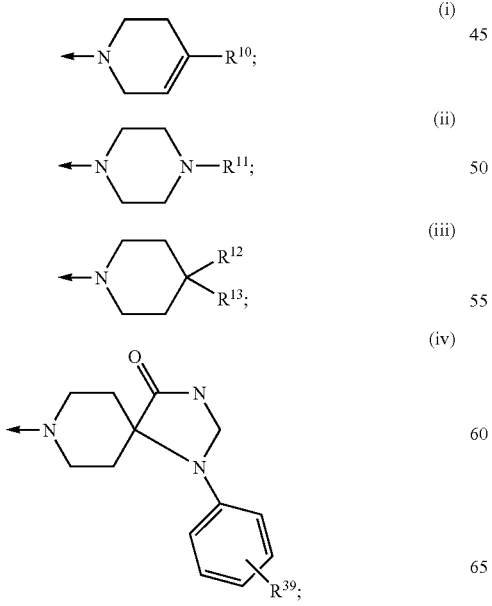

-continued

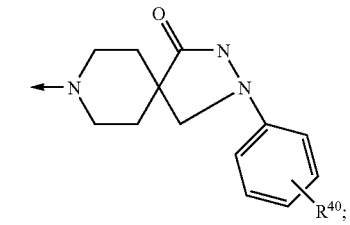

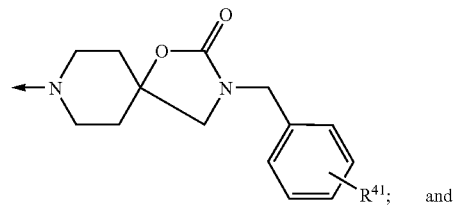

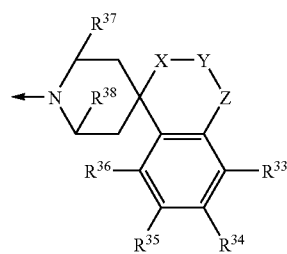

wherein R¹⁰ is an aryl;

wherein R¹¹ is selected from the group consisting of aryl, benzyl, halo-$C_{1-6}$-alk(en/yn)ylsulfonyl, $C_{1-6}$-alk(en/yn)ylsulfonyl, arylsulphonyl, arylacyl, $C_{1-6}$-alk(en/yn)ylcarbonyl, aminocarbonyl, $C_{1-6}$-alk(en/yn)ylaminocarbonyl, and di-($C_{1-6}$-alk(en)yl)aminocarbonyl;

wherein R¹² is an aryl;

wherein R¹³ is hydrogen, hydroxy, cyano, or amino, or one of the following groups:
—NHC₁₋₆-alk(en/yn)yl;
—N(C₁₋₆-alk(en/yn)yl)₂;
—NR¹⁴COR¹⁵, wherein R¹⁴ is hydrogen or $C_{1-6}$-alk(en/yn)yl and R¹⁵ is $C_{1-6}$-alk(en/yn)yl or $C_{3-8}$-cycloalk(en)yl;
—NR¹⁶COCONR¹⁷R¹⁸, wherein R¹⁶ is hydrogen or $C_{1-6}$-alk(en/yn)yl and R¹⁷ and R¹⁸ are selected independently from hydrogen, $C_{1-6}$-alk(en/yn)yl and $C_{3-8}$-cycloalkyl; or R¹⁷ and R¹⁸ together with the nitrogen to which they are attached form a piperidinyl, piperazinyl or morpholinyl, wherein said piperidinyl, piperazinyl and morpholinyl are optionally substituted with a $C_{1-6}$-alk(en/yn)yl;
—NR¹⁹CONR²⁰R²¹, wherein R¹⁹ is hydrogen or $C_{1-6}$-alk(en/yn)yl and R²⁰ and R²¹ are selected independently from hydrogen, $C_{1-6}$-alk(en/yn)yl or $C_{3-8}$-cycloalkyl; or R²⁰ and R²¹ together with the nitrogen to which they are attached form a piperidinyl, piperazinyl or morpholinyl, wherein said piperidinyl, piperazinyl and morpholinyl is optionally substituted with a $C_{1-6}$-alk(en/yn)yl;
—NR²²SO₂R²³, wherein R²² is hydrogen, $C_{1-6}$-alk(en/yn)yl or $C_{3-8}$-cycloalkyl and R²³ is amino, $C_{1-6}$-alk(en/yn)yl or $C_{3-8}$-cycloalkyl;
—COR²⁴, wherein R²⁴ is $C_{1-6}$-alk(en/yn)yl or $C_{3-8}$-cycloalkyl;

—CONR$^{25}$R$^{26}$, wherein R$^{25}$ and R$^{26}$ independently are selected from the group consisting of hydrogen, C$_{1-6}$-alk(en/yn)yl and C$_{3-8}$-cycloalkyl; or R$^{25}$ and R$^{26}$ together with the nitrogen to which they are attached form a piperidinyl, piperazinyl or morpholinyl, wherein said piperidinyl, piperazinyl and morpholinyl is optionally substituted with a C$_{1-6}$-alkyl;

—NHCOOR$^{42}$, wherein R$^{42}$ is C$_{1-6}$-alk(en/yn)yl or C$_{3-8}$-cycloalk(en)yl;

wherein X, Y, and Z are selected independently from a bond; O; NR$^{27}$; CR$^{28}$R$^{29}$ and S(O)$_m$, wherein m is 0, 1 or 2;

wherein R$^{27}$ is selected from the group consisting of hydrogen, C$_{1-6}$-alkylcarbonyl, C$_{1-6}$-alk(en/yn)yl, C$_{3-8}$-cycloalkyl, C$_{3-8}$-cycloalkyl-C$_{1-6}$alkyl, trifluoromethyl, acyl, thioacyl and trifluoromethylsulfonyl; or R$^{27}$ is a group R$^{30}$SO$_2$—, R$^{30}$OCO— or R$^{30}$SCO—, wherein R$^{30}$ is C$_{1-6}$-alk(en/yn)yl, C$_{3-8}$-cycloalkyl, or C$_{3-8}$-cycloalkyl-C$_{1-6}$-alkyl; or R$^{27}$ is a group R$^{31}$R$^{32}$NCO— or R$^{31}$R$^{32}$NCS—, wherein R$^{31}$ and R$^{32}$ are independently selected from the group consisting of hydrogen, C$_{1-6}$-alk(en/yn)yl, C$_{3-8}$-cycloalkyl, C$_{3-8}$-cycloalkyl-C$_{1-6}$-alkyl and aryl; or wherein R$^{31}$ and R$^{32}$ together with the N-atom to which they are linked, form a pyrrolidinyl, piperidinyl or perhydroazepinyl group;

wherein R$^{28}$ and R$^{29}$ are independently selected from the group consisting of hydrogen, fluoro, C$_{1-6}$-alk(en/yn)yl, C$_{3-8}$-cycloalkyl, and C$_{3-8}$-cycloalkyl-C$_{1-6}$-alkyl;

wherein R$^{33}$-R$^{36}$ are independently selected from the group consisting of hydrogen, halogen, cyano, nitro, C$_{1-6}$-alk(en/yn)yl, C$_{3-8}$-cycloalkyl, C$_{3-8}$-cycloalkyl-alkyl, amino, C$_{1-6}$-alkylamino, di-(C$_{1-6}$-alkyl)amino, C$_{1-6}$-alkylcarbonyl, aminocarbonyl, C$_{1-6}$-alkylaminocarbonyl, di-(C$_{1-6}$-alkyl)aminocarbonyl, C$_{1-6}$-alkoxy, C$_{1-6}$-alkylthio, hydroxy, trifluoromethyl, trifluoromethylsulfonyl and C$_{1-6}$-alkylsulfonyl;

wherein R$^{37}$-R$^{38}$ are either both hydrogen or are fused together in an ethylene chain CH$^2$—CH$^2$— forming an aza-bicyclo[3.2.1]octane-yl;

wherein R$^{39}$-R$^{41}$ are independently selected from the group consisting of hydrogen and halogen;

provided that no more than one of X, Y and Z may be a bond, and provided that two adjacent groups X, Y or Z may not at the same time be selected from the group consisting of O and S; or a pharmaceutically acceptable salt thereof.

2. The compound of claim 1, wherein R$^1$-R$^5$ are independently selected from the group consisting of hydrogen, halogen, cyano, C$_{1-6}$-alk(en/yn)yl, C$_{3-8}$-cycloalk(en)yl, C$_{3-8}$-cycloalk(en)yl-C$_{1-6}$-alk(en/yn)yl, C$_{1-6}$-alk(en/yn)yloxy, C$_{1-6}$-alk(en/yn)ylthio, and halo-C$_{1-6}$-alkyl.

3. The compound of claim 1, wherein R$^1$-R$^5$ are hydrogen.

4. The compound of claim 1, wherein R$^1$-R$^5$ are independently selected from the group consisting of hydrogen and halogen.

5. The compound of claim 1, wherein R$^1$-R$^5$ are independently selected from the group consisting of hydrogen and chloro.

6. The compound of claim 1, wherein R$^1$-R$^5$ are independently selected from the group consisting of hydrogen and fluoro.

7. The compound of claim 5, wherein R$^2$ is chloro and R$^3$ is hydrogen.

8. The compound of claim 5, wherein R$^2$ and R$^3$ are chloro.

9. The compound of claim 6, wherein R$^2$ is fluoro and R$^3$ is hydrogen.

10. The compound of claim 6, wherein R$^2$ and R$^3$ are fluoro.

11. The compound of claim 7, wherein R$^1$, R$^4$ and R$^5$ are hydrogen.

12. The compound of claim 1, wherein R$^6$ is selected from the group consisting of hydrogen, C$_{1-6}$-alkyl, C$_{3-8}$-cycloalkyl, and C$_{3-8}$-cycloalkyl-C$_{1-6}$-alkyl.

13. The compound of claim 1, wherein R$^6$ is selected from the group consisting of hydrogen and C$_{1-6}$-alk(en/yn)yl.

14. The compound of claim 1, wherein R$^6$ is hydrogen.

15. The compound of claim 1, wherein R$^6$ is a C$_{1-6}$-alkyl.

16. The compound of claim 15, wherein R$^6$ is methyl.

17. The compound of claim 1, wherein R$^7$ is the group [aryl-CR$^8$R$^9$—].

18. The compound of claim 17, wherein R$^8$ and R$^9$ are independently selected from the group consisting of hydrogen, C$_{1-6}$-alkyl, C$_{3-8}$-cycloalkyl and C$_{3-8}$-cycloalkyl-C$_{1-6}$-alkyl.

19. The compound of claim 17, wherein R$^8$ and R$^9$ are independently selected from the group consisting of hydrogen and C$_{1-6}$-alkyl.

20. The compound of claim 17, wherein R$^8$ and R$^9$ are independently selected from the group consisting of hydrogen and methyl.

21. The compound of claim 17, wherein R$^8$ and R$^9$ are hydrogen.

22. The compound of claim 17, wherein R$^8$ is hydrogen and R$^9$ is methyl.

23. The compound of claim 1, wherein R$^7$ is an aryl or a heteroaryl.

24. The compound of claim 23, wherein said aryl or heteroaryl is monocyclic or bicyclic.

25. The compound of claim 23, wherein said aryl or heteroaryl is unsubstituted.

26. The compound or salt of claim 23, wherein said aryl or heteroaryl is substituted with one or more substituents.

27. The compound claim 26, wherein said aryl or heteroaryl is substituted with one or more substituents selected from the group consisting of halogen, cyano, nitro, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, amino, C$_{1-6}$-alkylamino, di-(C$_{1-6}$-alkyl)amino, C$_{1-6}$-alkylcarbonyl, aminocarbonyl, C$_1$ aminocarbonyl, di-(C$_{1-6}$-alkyl)aminocarbonyl, C$_{1-6}$-alkylcarbonylamino, C$_{1-6}$-alkylcarbonyl C$_{1-6}$-alkylthio, hydroxy, trifluoromethyl, difluoromethyl, fluoromethyl and trifluoromethylsulfonyl.

28. The compound or salt of claim 17, wherein the aryl of said group aryl-CR$^8$R$^9$— is monocyclic, bicyclic, unsubstituted, or substituted with one or more substituents selected from the group consisting of halogen, cyano, nitro, C alkyl, C$_{2-6}$-alkenyl, C$_{2-6}$-alkynyl, C$_{3-8}$-cycloalkyl, C$_{3-8}$-cycloalkyl-C$_{1-6}$-alkyl, amino, C$_{1-6}$-alkylamino, di-(C$_{1-6}$-alkylamino, C$_{1-6}$-alkylcarbonyl, aminocarbonyl, C$_{1-6}$-alkylaminocarbonyl, di-(C$_{1-6}$-alkyl)aminocarbonyl, C$_{1-6}$-alkylcarbonylamino, C$_{1-6}$-alkylcarbonyl C$_{1-6}$-alkylamino, C$_{1-6}$-alkoxy, C$_{1-6}$-alkylthio, hydroxy, trifluoromethyl, difluoromethyl, fluoromethyl and trifluoromethylsulfonyl.

29. The compound claim 28, wherein said aryl is an optionally substituted phenyl.

30. The compound of claim 29, wherein said aryl is mono- or poly-substituted, with a halogen.

31. The compound of claim 17, wherein R$^7$ is benzyl or halogen substituted benzyl is.

32. The compound of claim 1, wherein Q is

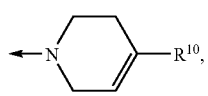
(i)

the arrow indicating the attachment point.

33. The compound claim 32, wherein $R^{10}$ is an aryl wherein said aryl is monocyclic, bicyclic, unsubstituted, or substituted with one or more substituents selected from the group consisting of halogen, cyano, nitro, C alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkylcarbonylamino, $C_{1-6}$: alkylcarbonyl $C_{1-6}$-alkylamino, $C_{1-6}$-alkylthio, hydroxy, trifluoromethyl, difluoromethyl, fluoromethyl and trifluoromethylsulfonyl.

34. The compound of claim 1, wherein Q is

(ii)

the arrow indicating the attachment point.

35. The compound of claim 34, wherein $R^{11}$ is selected from the group consisting of an optionally substituted aryl an optionally substituted benzyl, trifluoromethylsulfonyl, $C_{1-6}$-alkylsulfonyl, arylsulphonyl, arylacyl, $C_{1-6}$-alkylcarbonyl, aminocarbonyl, $C_{1-6}$-alkylaminocarbonyl and di-($C_{1-6}$-alkyl) aminocarbonyl).

36. The compound of claim 34, wherein $R^{11}$ is an aryl as wherein said aryl is monocyclic, bicyclic, unsubstituted, or substituted with one or more substituents selected from the group consisting of halogen, cyano, nitro $C_{1-6}$-alkyl, $C_{2-6}$-alkenyl, $C_{2-6}$-alkynyl, $C_{1-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkylcarbonylamino, $C_{1-6}$-alkylcarbonyl $C_{1-6}$-alkylamino, $C_{1-6}$-alkoxy, $C_{1-6}$-alkylthio, hydroxy, trifluoromethyl, difluoromethyl, fluoromethyl and trifluoromethylsulfonyl.

37. The compound of claim 34, wherein $R^{11}$ is an arylsulphonyl or an arylcarbonyl, wherein the aryl part of said arylsulphonyl or arylacyl is monocyclic, bicyclic, unsubstituted, or substituted with one or more substituents selected from the group consisting of halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkylcarbonylamino, $C_{1-6}$-alkylcarbonyl, $C_{1-6}$-alkylamino, $C_{1-6}$-alkoxy, $C_{1-6}$-alkylthio, hydroxy, trifluoromethyl, difluoromethyl, fluoromethyl and trifluoromethylsulfonyl.

38. The compound of claim 1, wherein Q is selected from the group consisting of

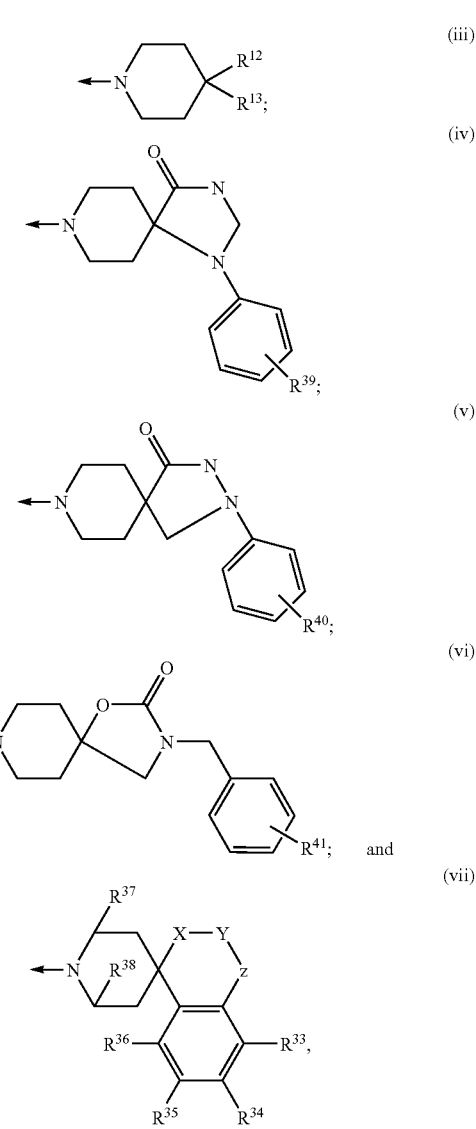

the arrow indicating the attachment point.

39. The compound of claim 38, wherein Q is

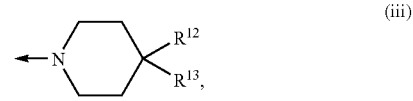
(iii)

the arrow indicating the attachment point.

40. The compound of claim 39, wherein $R^{12}$ is an aryl wherein said aryl is monocyclic, bicyclic, unsubstituted, or substituted with one or more substituents selected from the group consisting of halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkylcarbonylamino, $C_{1-6}$- alkylcarbonyl $C_{1-6}$-alkylamino, $C_{1-6}$-alkoxy, $C_{1-6}$-alkylthio, hydroxy, trifluoromethyl, difluoromethyl, fluoromethyl and trifluoromethylsulfonyl.

41. The compound of claim 39, wherein $R^{12}$ is a phenyl.

42. The compound claim 39, wherein $R^{12}$ is a phenyl substituted with one or more substituents.

43. The compound of claim 40, wherein the aryl of $R^{12}$ is substituted with one or more substituents selected from the group consisting of halogen and trifluoromethyl.

44. The compound claim 39, wherein $R^{12}$ is 4-chloro-3-trifluoromethyl-phenyl.

45. The compound of claim 39, wherein $R^{13}$ is selected from the group consisting of hydroxy, —$NR^{14}COR^{15}$, —$NR^{16}COCONR^{17}R^{18}$, —$NR^{19}CONR^{20}R^{21}$, —$NR^{22}SO_2R^{23}$, —$COR^{24}$, and —$CONR^{25}R^{26}$.

46. The compound of claim 39, wherein $R^{13}$ is hydroxy.

47. The compound of claim 46, wherein $R^{12}$ is 4-chloro-3-trifluoromethyl-phenyl.

48. The compound of claim 39, wherein $R^{13}$ is —$NR^{14}COR^{15}$.

49. The compound of claim 48, wherein $R^{14}$ is hydrogen or $C_{1-6}$ alkyl and $R^{15}$ is $C_{1-6}$-alkyl or $C_{3-8}$-cycloalkyl.

50. The compound of claim 48, wherein $R^{14}$ is hydrogen or methyl.

51. The compound of claim 48, wherein $R^{15}$ is methyl.

52. The compound of claim 48, wherein $R^{14}$ is hydrogen and $R^{15}$ is methyl; or $R^{14}$ and $R^{15}$ are each methyl.

53. The compound of claim 39, wherein $R^{13}$ is —$NR^{16}COCONR^{17}R^{18}$.

54. The compound of claim 53, wherein $R^{16}$ is hydrogen or $C_{1-6}$-alkyl and wherein $R^{17}$ and $R^{18}$ are selected independently from hydrogen, $C_{1-6}$-alkyl and $C_{3-8}$-cycloalkyl.

55. The compound of claim 53, wherein $R^{16}$ is hydrogen or $C_{1-6}$-alkyl and wherein $R^{17}$ and $R^{18}$ together with the nitrogen to which they are attached form a piperidinyl, piperazinyl or morpholinyl, wherein said piperidinyl, piperazinyl or morpholinyl is optionally substituted with a $C_{1-6}$-alkyl.

56. The compound of claim 53, wherein said $R^{16}$, $R^{17}$ and $R^{18}$ are each hydrogen; $R^{16}$ is $C_{1-6}$alkyl, and $R^{17}$ and $R^{18}$ are each hydrogen; $R^{16}$ and $R^{17}$ are each hydrogen and $R^{18}$ is $C_{1-6}$-alkyl; $R^{16}$ and $R_{17}$ are each $C_{1-6}$-alkyl and $R_{18}$ is hydrogen; $R^{16}$ is hydrogen and $R^{17}$ and $R^{18}$ are each $C_{1-6}$-alkyl; or $R^{16}$, $R^{17}$ and $R^{18}$ are each $C_{1-6}$-alkyl.

57. The compound of claim 39, wherein $R^{13}$ is —$NR^{19}CONR^{20}R^{21}$.

58. The compound of claim 57, wherein $R^{19}$, $R^{20}$ and $R^{21}$ are independently selected from the group consisting of hydrogen, $C_{1-6}$-alkyl and $C_{3-8}$-cycloalkyl.

59. The compound of claim 57, wherein $R^{19}$, $R^{20}$ and $R^{21}$ are independently selected from the group consisting of hydrogen and $C_{1-6}$-alkyl.

60. The compound of claim 57, wherein $R^{19}$ is a $C_{1-6}$-alkyl and $R^{20}$ and $R^{21}$ are each hydrogen; $R^{19}$ and $R^{20}$ are each hydrogen and $R^{21}$ is a $C_{1-6}$-alkyl; $R^{19}$ and $R^{20}$ are each independently $C_{1-6}$-alkyl and $R^{21}$ is H; $R^{19}$ is H, and $R^{20}$ and $R^{21}$ are each independently $C_{1-6}$-alkyl; or $R^{19}$, $R^{20}$ and $R^{21}$ are each independently $C_{1-6}$-alkyl.

61. The compound of claim 59, wherein $R^{19}$, $R^{20}$ and $R^{21}$ are each hydrogen.

62. The compound of claim 57, wherein $R^{19}$ is H.

63. The compound of claim 57, wherein $R^{20}$ and $R^{21}$ are independently selected from the group consisting of hydrogen, Me, Et, Bu, and i-Pr.

64. The compound of claim 63, wherein $R^{19}$ is H.

65. The compound of claim 39, wherein $R^{13}$ is —$NR^{22}SO_2R^{23}$.

66. The compound of claim 65, wherein $R^{22}$ is hydrogen, a $C_{1-6}$-alkyl or $C_{3-8}$-cycloalkyl and $R^{23}$ is amino, $C_{1-6}$-alkyl or $C_{3-8}$-cycloalkyl.

67. The compound of claim 65, wherein $R^{22}$ is hydrogen and $R^{23}$ is a $C_{1-6}$-alkyl or $R^{22}$ and $R^{23}$ are each independently $C_{1-6}$-alkyl.

68. The compound of claim 65, wherein $R^{22}$ is hydrogen.

69. The compound of claim 65, wherein $R^{23}$ is methyl.

70. The compound of claim 65, wherein $R^{22}$ and $R^{23}$ are each methyl.

71. The compound of claim 65, wherein $R^{22}$ is hydrogen and $R^{23}$ is methyl.

72. The compound of claim 39, wherein $R^{13}$ is —$COR^{24}$.

73. The compound of claim 72, wherein $R^{24}$ is a $C_{1-6}$-alkyl.

74. The compound of claim 72, wherein $R^{24}$ is methyl.

75. The compound of claim 39, wherein $R^{13}$ is —$CONR^{25}R^{26}$.

76. The compound of claim 75, wherein $R^{25}$ and $R^{26}$ are independently selected from the group consisting of hydrogen, $C_{1-6}$-alkyl and $C_{3-8}$-cycloalkyl.

77. The compound of claim 75, wherein $R^{25}$ and $R^{26}$ are each independently hydrogen or methyl.

78. The compound of claim 75, wherein $R^{25}$ and $R^{26}$ together with the nitrogen to which they are attached form a piperidinyl, piperazinyl or morpholinyl, wherein said piperidinyl, piperazinyl or morpholinyl is optionally substituted with a $C_{1-6}$-alkyl.

79. The compound of claim 75, wherein $R^{25}$ and $R^{26}$ together with the nitrogen to which they are attached form a piperidinyl, wherein said piperidinyl is optionally substituted with a $C_{1-6}$-alkyl.

80. The compound of claim 1, wherein Q is

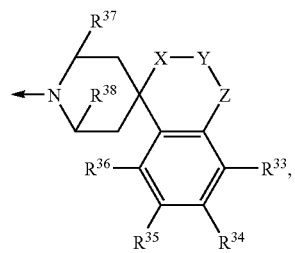

(vii)

the arrow indicating the attachment point.

81. The compound of claim 80, wherein Y is a bond and X and Z are selected independently from O; $NR^{27}$; $CR^{28}R^{29}$ and $S(O)_m$, provided that X and Z may not at the same time be O and S.

82. The compound of claim 80, wherein Y is a bond and X and Z are selected independently from $CR^{28}R^{29}$ and $NR^{27}$.

83. The compound of claim 80, wherein X is $CR^{28}R^{29}$, Y is a bond and Z is $NR^{27}$.

84. The compound of claim 83, wherein $R^{28}$ and $R^{29}$ are each hydrogen.

85. The compound of claim 81, wherein X is $CR^{28}R^{29}$ and $R^{28}$ and $R^{29}$ are each hydrogen.

86. The compound of claim 80, wherein X is $CR^{28}R^{29}$, Y is a bond and Z is O.

87. The compound of claim 86, wherein $R^{28}$ and $R^{29}$ are each hydrogen.

88. The compound of claim 80, wherein X is O, Y is a bond and Z is $CR^{28}R^{29}$.

89. The compound of claim 88, wherein $R^{28}$ and $R^{29}$ are each hydrogen.

90. The compound of claim 80, wherein $R^{27}$ is an acyl.

91. The compound of claim 90, wherein $R^{27}$ is a $C_{1-6}$-alkylcarbonyl.

92. The compound of claim 83, wherein $R^{27}$ is a $C_{1-6}$-alkylcarbonyl.

93. The compound of claim 92, wherein said $R^{27}$ is —COCH$_3$.

94. The compound of claim 83, wherein $R^{28}$ and $R^{29}$ are each hydrogen; and $R^{27}$ is —COCH$_3$.

95. The compound of claim 80, wherein $R^{27}$ is selected from the group consisting of $R^{30}SO_2$—, $R^{30}OCO$— and $R^{30}SCO$—.

96. The compound of claim 80, wherein $R^{27}$ is $R^{30}SO_2$.

97. The compound of claim 96, wherein $R^{30}$ is $C_{1-6}$-alkyl.

98. The compound of claim 96, wherein $R^{30}$ is methyl.

99. The compound of claim 96, wherein X is $CR^{28}R^{29}$, Y is a bond and Z is $NR^{27}$.

100. The compound of claim 99, wherein $R^{28}$ and $R^{29}$ are each hydrogen.

101. The compound of claim 80, wherein $R^{27}$ is $R^{31}R^{32}NCO$— or $R^{30}R^{31}NCS$—.

102. The compound of claim 80, wherein Y is a bond.

103. The compound of claim 80, wherein $R^{33}$-$R^{36}$ are independently selected from the group consisting of hydrogen and halogen.

104. The compound of claim 80, wherein $R^{37}$ and $R^{38}$ are both hydrogen.

105. The compound of claim 1, wherein $R^{1-5}$ are independently selected from the group consisting of hydrogen and halogen, and $R^6$ is selected from the group consisting of hydrogen and $C_{1-6}$-alk(en/yn)yl.

106. The compound of claim 1, wherein $R^{1-5}$ are independently selected from the group consisting of hydrogen and halogen, and $R^6$ is $C_{1-6}$-alkyl.

107. The compound of claim 1, wherein $R^6$ is hydrogen or $C_{1-6}$-alkyl, and $R^7$ is benzyl or halogen substituted benzyl.

108. The compound of claim 105, wherein Q is

(iii)

the arrow indicating the attachment point and $R^{12}$ is phenyl.

109. The compound of claim 1, wherein n is 0.

110. The compound of claim 1, wherein the compound of formula I is the (1S,2R)-isomer having the structure:

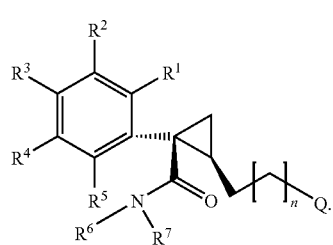

(IA)

111. The compound of claim 1, wherein the compound of formula I is a racemic mixture comprising the (1S,2R)-isomer having the structure:

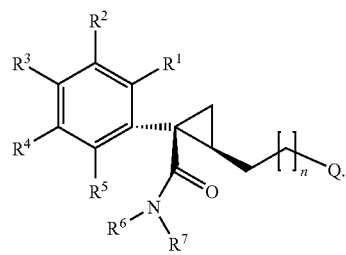

(IA)

112. The compound of claim 1, wherein the compound of formula I is a mixture of stereoisomers of said compound, which mixture comprises the (1S,2R)-isomer having the structure:

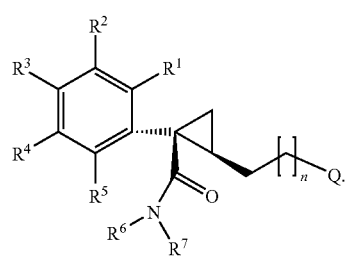

(IA)

113. The compound of claim 1 selected from the group consisting of:

(1S,2R)-2-(4-Acetylamino-4-phenyl-piperidin-1-ylmethyl)-1-(3,4-dichlorophenyl)-cyclopropanecarboxylic acid benzyl-methyl-amide;

(1S,2R)-2-[4-(Acetyl-methyl-amino)-4-phenyl-piperidin-1-ylmethyl]-1-(3,4-dichlorophenyl)-cyclopropanecarboxylic acid benzyl-methyl-amide;

(1S,2R)-2-[1-acetyl-spiro[2,3-dihydro-1H-indol-3-yl-3,4'-piperidine-1'-yl-methyl]-1-(3,4-dichlorophenyl)-cyclopropanecarboxylic acid benzyl-methyl-amide;

(1S,2R)-2-[1-acetyl-5-fluorospiro[2,3-dihydro-1H-indol-3-yl-3,4'-piperidine-1'-yl-methyl]-1-(3,4-dichlorophenyl)-cyclopropanecarboxylic acid benzyl-methyl-amide;

(1S,2R)-2-[1-acetyl-spiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl) amide;

(1S,2R)-2-[1-acetyl-5-fluorospiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl) amide;

(1S,2R)-1-Phenyl-2-[4-phenyl-4-(piperidine-1-carbonyl)-piperidin-1-ylmethyl]-cyclopropanecarboxylic acid benzyl-methyl-amide;

(1S,2R)-2-[1-methanesulphonyl-spiro[2,3-dihydro-1H-indol-3-yl-3,4'-piperidine-1'-yl-methyl]-1-phenyl-cyclopropanecarboxylic acid benzyl-methyl-amide;

(1S,2R)-2-(4-Acetyl-4-phenyl-piperidin-1-ylmethyl)-1-phenyl-cyclopropanecarboxylic acid benzyl-methyl-amide;

(1S,2R)-2-[4-(4-Chloro-3-trifluoromethyl-phenyl)-4-hydroxy-piperidin-1-ylmethyl]-1-phenyl-cyclopropanecarboxylic acid benzyl-methyl-amide;

(1S,2R)-2-[1-acetyl-5-fluorospiro[2,3-dihydro-1H-indol-3-yl-3,4'-piperidine-1'-yl-methyl]-1-phenyl-cyclopropanecarboxylic acid benzyl-methyl-amide;

(1S,2R)-2-(4-Acetylamino-4-phenyl-piperidin-1-ylmethyl)-1-(4-chloro-phenyl)-cyclopropanecarboxylic acid benzyl-methyl-amide;

(1S,2R)-1-(4-Chloro-phenyl)-2-[4-phenyl-4-(piperidine-1-carbonyl)-piperidin-1-ylmethyl]-cyclopropanecarboxylic acid benzyl-methyl-amide;

(1S,2R)-2-[4-(Acetyl-methyl-amino)-4-phenyl-piperidin-1-ylmethyl]-1-(4-chloro-phenyl)-cyclopropanecarboxylic acid benzyl-methyl-amide;

(1S,2R)-2-(4-Acetyl-4-phenyl-piperidin-1-ylmethyl)-1-(4-chloro-phenyl)-cyclopropanecarboxylic acid benzyl-methyl-amide;

(1S,2R)-2-[1-acetyl-spiro[2,3-dihydro-1H-indol-3-yl-3,4'-piperidine-1'-yl-methyl]-1-(4-chlorophenyl)-cyclopropanecarboxylic acid benzyl-methyl-amide;

(1S,2R)-2-[1-acetyl-5-fluorospiro[2,3-dihydro-1H-indol-3-yl-3,4'-piperidine-1'-yl-methyl]-1-(4-chlorophenyl)-cyclopropanecarboxylic acid benzyl-methyl-amide;

(1S,2R)-2-(4-Acetylamino-4-phenyl-piperidin-1-ylmethyl)-1-(3,4-difluoro-phenyl)-cyclopropanecarboxylic acid methyl-(1-phenyl-ethyl)-amide;

(1S,2R)-2-[4-(Acetyl-methyl-amino)-4-phenyl-piperidin-1-ylmethyl]-1-(3,4-difluoro-phenyl)-cyclopropanecarboxylic acid methyl-([S]-1-phenyl-ethyl)-amide;

(1S,2R)-2-[1-acetyl-5-fluorospiro[2,3-dihydro-1H-indol-3-yl-3,4'-piperidine-1'-yl-methyl]-1-(3,4-difluorophenyl)-cyclopropanecarboxylic acid methyl-([S]-1-phenyl-ethyl)-amide;

(1S,2R)-2-(4-Acetylamino-4-phenyl-piperidin-1-ylmethyl)-1-phenyl-cyclopropanecarboxylic acid (4-fluoro-benzyl)-methyl-amide;

(1S,2R)-2-[4-(Acetyl-methyl-amino)-4-phenyl-piperidin-1-ylmethyl]-1-phenyl-cyclopropanecarboxylic acid (4-fluoro-benzyl)-methyl-amide;

(1S,2R)-2-[1-acetyl-spiro[2,3-dihydro-1H-indol-3-yl-3,4'-piperidine-1'-yl-methyl]-1-phenyl-cyclopropanecarboxylic acid (4-fluoro-benzyl)-methyl-amide;

(1S,2R)-2-[4-(4-Chloro-3-trifluoromethyl-phenyl)-4-hydroxy-piperidin-1-ylmethyl]-1-phenyl-cyclopropanecarboxylic acid (4-fluoro-benzyl)-methyl-amide;

(1S,2R)-2-[1-acetyl-5-fluorospiro[2,3-dihydro-1H-indol-3-yl-3,4'-piperidine-1'-yl-methyl]-1-phenyl-cyclopropanecarboxylic acid (4-fluoro-benzyl)-methyl-amide;

(1S,2R)-2-[4-(Acetyl-methyl-amino)-4-phenyl-piperidin-1-ylmethyl]-1-(4-chloro-phenyl)-cyclopropanecarboxylic acid (4-fluoro-benzyl)-methyl-amide;

(1S,2R)-2-[1-acetyl-5-fluoro-spiro[2,3-dihydro-1H-indol-3,3'-(8'-aza-bicyclo[3.2.1]octane-8'-yl)]-1-(4-chlorophenyl)-cyclopropanecarboxylic acid (4-fluoro-benzyl)-methyl-amide;

(1S,2R)-2-(4-Acetyl-4-phenyl-piperidin-1-ylmethyl)-1-(4-chloro-phenyl)-cyclopropanecarboxylic acid (4-fluoro-benzyl)-methyl-amide;

(1S,2R)-2-[1-acetyl-spiro[2,3-dihydro-1H-indol-3-yl-3,4'-piperidine-1'-yl-methyl]-1-(4-chlorophenyl)-cyclopropanecarboxylic acid (4-fluoro-benzyl)-methyl-amide;

(1S,2R)-2-[1-acetyl-5-fluorospiro[2,3-dihydro-1H-indol-3-yl-3,4'-piperidine-1'-yl-methyl]-1-(4-chlorophenyl)-cyclopropanecarboxylic acid (4-fluoro-benzyl)-methyl-amide;

(1S,2R)-1-(4-Fluoro-phenyl)-2-[4-phenyl-4-(piperidine-1-carbonyl)-piperidin-1-ylmethyl]-cyclopropanecarboxylic acid (4-fluoro-benzyl)-methyl-amide;

(1S,2R)-2-[1-acetyl-5-fluorospiro[2,3-dihydro-1H-indol-3-yl-3,4'-piperidine-1'-yl-methyl]-1-(4-fluorophenyl)-cyclopropanecarboxylic acid (4-fluoro-benzyl)-methyl-amide;

(1S,2R)-1-(3,4-Difluoro-phenyl)-2-[4-phenyl-4-(piperidine-1-carbonyl)-piperidin-1-ylmethyl]-cyclopropanecarboxylic acid-methyl-amide;

(1S,2R)-2-[1-acetyl-5-fluoro-spiro[2,3-dihydro-1H-indol-3,3'-(8'-aza-bicyclo[3.2.1]octane-8'-yl)]-1-(3,4-difluorophenyl)-cyclopropanecarboxylic acid (4-fluoro-benzyl)-methyl-amide;

(1S,2R)-2-[1-acetyl-5-fluorospiro[2,3-dihydro-1H-indol-3-yl-3,4'-piperidine-1'-yl-methyl]-1-(3,4-fluorophenyl)-cyclopropanecarboxylic acid (4-fluoro-benzyl)-methyl-amide;

(1S,2R)-1-(3,4-Dichlorophenyl)-2-[4-phenyl-4-(piperidine-1-carbonyl)-piperidin-1-ylmethyl]-cyclopropanecarboxylic acid benzyl-methyl-amide;

(1S,2R)-2-(4-Acetyl-4-phenyl-piperidin-1-ylmethyl)-1-(3,4-dichlorophenyl)-cyclopropanecarboxylic acid benzyl-methyl-amide;

(1S,2R)-2-[1-acetyl-5-fluorospiro[2,3-dihydro-1H-indol-3-yl-3,4'-piperidine-1'-yl-methyl]-1-(4-fluorophenyl)-cyclopropanecarboxylic acid methyl-([S]-1-phenyl-ethyl)amide;

(1S,2R)-2-(4-Acetylamino-4-phenyl-piperidin-1-ylmethyl)-1-(3,4-dichlorophenyl)-cyclopropanecarboxylic acid methyl-(1-phenyl-ethyl)-amide;

(1S,2R)-1-(3,4-Dichloro-phenyl)-2-[4-phenyl-4-(piperidine-1-carbonyl)-piperidin-1-ylmethyl]-cyclopropanecarboxylic acid methyl-([S]-1-phenyl-ethyl)amide;

(1S,2R)-2-[4-(Acetyl-methyl-amino)-4-phenyl-piperidin-1-ylmethyl]-1-(3,4-dichlorophenyl)-cyclopropanecarboxylic acid methyl-([S]-1-phenyl-ethyl)-amide;

(1S,2R)-1-Phenyl-2-[4-phenyl-4-(piperidine-1-carbonyl)-piperidin-1-ylmethyl]-cyclopropanecarboxylic acid (4-fluoro-benzyl)-methyl-amide;

(1S,2R)-1-(4-Chloro-phenyl)-2-[4-phenyl-4-(piperidine-1-carbonyl)-piperidin-1-ylmethyl]-cyclopropanecarboxylic acid (4-fluoro-benzyl)-methyl-amide;

(1S,2R)-2-(4-Acetylamino-4-phenyl-piperidin-1-ylmethyl)-1-(4-chloro-phenyl)-cyclopropanecarboxylic acid (4-fluoro-benzyl)-methyl-amide;

(1S,2R)-2-(4-Acetylamino-4-phenyl-piperidin-1-ylmethyl)-1-(4-chloro-phenyl)-cyclopropanecarboxylic acid (2-chloro-benzyl)-methyl-amide;

(1S,2R)-1-(4-Chloro-phenyl)-2-[4-phenyl-4-(piperidine-1-carbonyl)-piperidin-1-ylmethyl]-cyclopropanecarboxylic acid (2-chloro-benzyl)-methyl-amide;

(1S,2R)-2-[4-(Acetyl-methyl-amino)-4-phenyl-piperidin-1-ylmethyl]-1-(4-chloro-phenyl)-cyclopropanecarboxylic acid (2-chloro-benzyl)-methyl-amide;

(1S,2R)-2-[1-acetyl-5-fluorospiro[2,3-dihydro-1H-indol-3-yl-3,4'-piperidine-1'-yl-methyl]-1-(4-chlorophenyl)-cyclopropanecarboxylic acid (2-chlorobenzyl)-methyl-amide;

(1S,2R)-2-[4-(Acetyl-methyl-amino)-4-phenyl-piperidin-1-ylmethyl]-1-(4-fluoro-phenyl)-cyclopropanecarboxylic acid (2-chloro-benzyl)-methyl-amide;

(1S,2R)-2-[4-(Acetyl-methyl-amino)-4-phenyl-piperidin-1-ylmethyl]-1-(3,4-difluoro-phenyl)-cyclopropanecarboxylic acid (2-chloro-benzyl)-methyl-amide;

(1S,2R)-2-(4-Acetylamino-4-phenyl-piperidin-1-ylmethyl)-1-(3,4-dichlorophenyl)-cyclopropanecarboxylic acid (2-chloro-benzyl)-methyl-amide;

(1S,2R)-1-(3,4-Dichlorophenyl)-2-[4-phenyl-4-(piperidine-1-carbonyl)-piperidin-1-ylmethyl]-cyclopropanecarboxylic acid (2-chloro-benzyl)-methyl-amide;

(1S,2R)-2-[4-(Acetyl-methyl-amino)-4-phenyl-piperidin-1-ylmethyl]-1-(3,4-dichlorophenyl)-cyclopropanecarboxylic acid (2-chloro-benzyl)-methyl-amide;

(1S,2R)-2-[1-acetyl-spiro[2,3-dihydro-1H-indol-3-yl-3,4'-piperidine-1'-yl-methyl]-1-(3,4-dichlorophenyl)-cyclopropanecarboxylic acid (2-chlorobenzyl)-methyl-amide;

(1S,2R)-1-(3,4-Dichlorophenyl)-2-(4-phenyl-piperidin-1-ylmethyl)-cyclopropanecarboxylic acid benzyl-methyl-amide;

(1S,2R)-2-(4-Acetylamino-4-phenyl-piperidin-1-ylmethyl)-1-(3,4-dichlorophenyl)-cyclopropanecarboxylic acid (1-methyl-1-phenyl-ethyl)-amide;

(1S,2R)-2-(4-phenyl-piperidin-1-ylmethyl)-1-(3,4-dichlorophenyl)-cyclopropanecarboxylic acid benzyl-ethyl-amide;

(1S,2R)-2-(4-Acetylamino-4-phenyl-piperidin-1-ylmethyl)-1-(3,4-dichlorophenyl)-cyclopropanecarboxylic acid benzyl-methyl-amide-([R]-1-phenyl-ethyl) amide;

(1R,2S)-2-(4-Acetylamino-4-phenyl-piperidin-1-ylmethyl)-1-(3,4-dichlorophenyl)-cyclopropanecarboxylic acid benzyl-methyl-amide;

(1R,2R)-2-(4-Acetylamino-4-phenyl-piperidin-1-ylmethyl)-1-(3,4-dichlorophenyl)-cyclopropanecarboxylic acid benzyl-methyl-amide;

(1S,2S)-2-(4-Acetylamino-4-phenyl-piperidin-1-ylmethyl)-1-(3,4-dichlorophenyl)-cyclopropanecarboxylic acid benzyl-methyl-amide;

(1S,2R)-2-(4-Acetylamino-4-phenyl-piperidin-1-ylmethyl)-1-(3,4-dichlorophenyl)-cyclopropanecarboxylic acid methyl-([R]1-phenyl-ethyl)-amide;

(1S,2R)-2-[4-(Acetyl-methyl-amino)-4-phenyl-piperidin-1-ylmethyl]-1-(3,4-dichlorophenyl)-cyclopropanecarboxylic acid methyl-([R]-1-phenyl-ethyl)-amide;

(1S,2R)-2-[1-acetyl-spiro[2,3-dihydro-1H-indol-3-yl-3,4'-piperidine-1'-yl-methyl]-1-(3,4-dichlorophenyl)-cyclopropanecarboxylic acid methyl-([R]-1-phenyl-ethyl) amide;

(1S,2R)-2-[1-acetyl-5-fluoro-spiro[2,3-dihydro-1H-indol-3-yl-3,4'-piperidine-1'-yl-methyl]-1-(3,4-dichlorophenyl)-cyclopropanecarboxylic acid methyl-([R]-1-phenyl-ethyl) amide;

(1S,2R)-2-(4-Acetylamino-4-phenyl-piperidin-1-ylmethyl)-1-phenyl-cyclopropanecarboxylic acid benzyl-methyl-amide;

(1S,2R)-1-(3,4-Dichlorophenyl)-2-[4-phenyl-4-(piperidine-1-carbonyl)-piperidin-1-ylmethyl]-cyclopropanecarboxylic acid methyl-([S]-1-phenyl-ethyl)-amide;

(1S,2R)-2-[1-acetyl-5-fluoro-spiro[2,3-dihydro-1H-indol-3-yl-3,4'-piperidine-1'-yl-methyl]-1-(3,4-dichlorophenyl)-cyclopropanecarboxylic acid methyl-([S]-1-phenyl-ethyl) amide;

(1S,2R)-1-Phenyl-2-[4-phenyl-4-(piperidine-1-carbonyl)-piperidin-1-ylmethyl]-cyclopropanecarboxylic acid (4-fluoro-benzyl)-methyl-amide;

(1S,2R)-2-(4-Acetyl-4-phenyl-piperidin-1-ylmethyl)-1-phenyl-cyclopropanecarboxylic acid (4-fluoro-benzyl)-methyl-amide;

(1S,2R)-2-[1-methanesulphonyl-spiro[2,3-dihydro-1H-indol-3-yl-3,4'-piperidine-1'-yl-methyl]-1-(4-fluorophenyl)-cyclopropanecarboxylic acid (4-fluoro-benzyl)-methyl-amide;

(1S,2R)-2-[4-(Acetyl-methyl-amino)-4-phenyl-piperidin-1-ylmethyl]-1-(4-fluorophenyl)-cyclopropanecarboxylic acid (4-fluoro-benzyl)-methyl-amide;

(1S,2R)-2-(4-Acetyl-4-phenyl-piperidin-1-ylmethyl)-1-(4-fluorophenyl)-cyclopropanecarboxylic acid (4-fluoro-benzyl)-methyl-amide;

(1S,2R)-2-[1-acetyl-spiro[2,3-dihydro-1H-indol-3-yl-3,4'-piperidine-1'-yl-methyl]-1-(4-fluorophenyl)-cyclopropanecarboxylic acid (4-fluoro-benzyl)-methyl-amide;

(1S,2R)-2-(4-Acetyl-4-phenyl-piperidin-1-ylmethyl)-1-(3,4-difluorophenyl)-cyclopropanecarboxylic acid (4-fluoro-benzyl)-methyl-amide;

(1S,2R)-2-[1-acetyl-spiro[2,3-dihydro-1H-indol-3-yl-3,4'-piperidine-1'-yl-methyl]-1-(3,4-difluorophenyl)-cyclopropanecarboxylic acid (4-fluoro-benzyl)-methyl-amide;

(1S,2R)-1-(4-Fluoro-phenyl)-2-[4-phenyl-4-(piperidine-1-carbonyl)-piperidin-1-ylmethyl]-cyclopropanecarboxylic acid methyl-([S]1-phenyl-ethyl)-amide;

(1S,2R)-2-(4-Acetyl-4-phenyl-piperidin-1-ylmethyl)-1-(4-chlorophenyl)-cyclopropanecarboxylic acid (2-chloro-benzyl)-methyl-amide;

(1S,2R)-2-[1-acetyl-spiro[2,3-dihydro-1H-indol-3-yl-3,4'-piperidine-1'-yl-methyl]-1-(4-chlorophenyl)-cyclopropanecarboxylic acid (2-chloro-benzyl)-methyl-amide;

(1S,2R)-2-(4-Acetylamino-4-phenyl-piperidin-1-ylmethyl)-1-(4-fluorophenyl)-cyclopropanecarboxylic acid (2-chloro-benzyl)-methyl-amide;

(1S,2R)-1-(4-Fluoro-phenyl)-2-[4-phenyl-4-(piperidine-1-carbonyl)-piperidin-1-ylmethyl]-cyclopropanecarboxylic acid (2-chloro-benzyl)-methyl-amide;

(1S,2R)-2-(4-Acetylamino-4-phenyl-piperidin-1-ylmethyl)-1-(3,4-difluorophenyl)-cyclopropanecarboxylic acid (2-chloro-benzyl)-methyl-amide;

(1S,2R)-1-(3,4-Difluorophenyl)-2-[4-phenyl-4-(piperidine-1-carbonyl)-piperidin-1-ylmethyl]-cyclopropanecarboxylic acid (2-chloro-benzyl)-methyl-amide;

(1S,2R)-2-[1-acetyl-spiro[2,3-dihydro-1H-indol-3-yl-3,4'-piperidine-1'-yl-methyl]-1-(3,4-difluorophenyl)-cyclopropanecarboxylic acid (2-chloro-benzyl)-methyl-amide;

(1S,2R)-2-[1-acetyl-5-fluoro-spiro[2,3-dihydro-1H-indol-3-yl-3,4'-piperidine-1'-yl-methyl]-1-(3,4-difluorophenyl)-cyclopropanecarboxylic acid (2-chloro-benzyl)-methyl-amide;

(1S,2R)-1-(3,4-Dichlorophenyl)-2-(4-phenyl-piperidin-1-ylmethyl)-cyclopropanecarboxylic acid 3,4-dichloro-benzylamide;

(1S,2R)-1-(3,4-Dichlorophenyl)-2-(4-phenyl-piperidin-1-ylmethyl)-cyclopropanecarboxylic acid 3,4-dimethoxy-benzylamide;

(1S,2R)-2-(4-Acetylamino-4-phenyl-piperidin-1-ylmethyl)-1-(3,4-dichlorophenyl)-cyclopropanecarboxylic acid phenylamide;

(1S,2R)-2-(4-Acetylamino-4-phenyl-piperidin-1-ylmethyl)-1-(3,4-dichlorophenyl)-cyclopropanecarboxylic acid (1-methyl-1-phenyl-ethyl)-amide;

(1S,2R)-1-Phenyl-2-[4-(3-trifluoromethylphenyl)-piperazin-1-ylmethyl]-cyclopropanecarboxylic acid benzyl-methyl-amide;

(1S,2R)-2-(4-Benzyl-piperazin-1-ylmethyl)-1-(4-chlorophenyl)-cyclopropanecarboxylic acid (4-fluoro-benzyl)-methyl-amide;

(1S,2R)-1-(4-chlorophenyl)-2-[4-(3-trifluoromethylphenyl)-piperazin-1-ylmethyl]-cyclopropanecarboxylic acid 4-fluorobenzyl-methyl-amide;

(1S,2R)-2-(4-Benzyl-piperazin-1-ylmethyl)-1-(4-chlorophenyl)-cyclopropanecarboxylic acid benzyl-methyl-amide;

(1S,2R)-2-(4-Benzyl-piperazin-1-ylmethyl)-1-phenyl-cyclopropanecarboxylic acid benzyl-methyl-amide;

(1S,2R)-1-(4-chlorophenyl)-2-[4-(3-trifluoromethylphenyl)-piperazin-1-ylmethyl]-cyclopropanecarboxylic acid benzyl-methyl-amide;

(1S,2R)-1-phenyl-2-[4-(3-trifluoromethylphenyl)-piperazin-1-ylmethyl]-cyclopropanecarboxylic acid 4-fluorobenzyl-methyl-amide;

(1S,2R)-2-(4-Acetylamino-4-phenyl-piperidin-1-ylmethyl)-1-(3,4-dichloro-phenyl)-cyclopropanecarboxylic acid benzyl amide;

(1S,2R)-2-[1-acetyl-5-fluoro-spiro[2,3-dihydro-1H-indol-3-yl-3,4'-piperidine-1'-yl-methyl]-1-(3,4-difluorophenyl)-cyclopropanecarboxylic acid (2-fluoro-benzyl)-amide;

(1S,2R)-2-(4-Acetylamino-4-phenyl-piperidin-1-ylmethyl)-1-(3,4-dichlorophenyl)-cyclopropanecarboxylic acid methyl-[1-(4-methoxyphenyl)-ethyl]-amide;

(1S,2R)-2-(4-Acetylamino-4-phenyl-piperidin-1-ylmethyl)-1-(3,4-dichloro-phenyl)-cyclopropanecarboxylic acid (2-chlorobenzyl) amide;

(1S,2R)-2-(4-Acetylamino-4-phenyl-piperidin-1-ylmethyl)-1-(3,4-dichloro-phenyl)-cyclopropanecarboxylic acid (3,4-dichlorobenzyl) amide;

(1S,2R)-2-(4-Acetylamino-4-phenyl-piperidin-1-ylmethyl)-1-(3,4-dichloro-phenyl)-cyclopropanecarboxylic acid methyl-phenyl-amide;

(1S,2R)-2-(4-Acetylamino-4-phenyl-piperidin-1-ylmethyl)-1-(4-methoxy-phenyl)-cyclopropanecarboxylic acid (4-fluoro-benzyl)-methyl-amide;

(1S,2R)-2-(4-Acetylamino-4-phenyl-piperidin-1-ylmethyl)-1-p-tolyl-cyclopropanecarboxylic acid (4-fluoro-benzyl)-methyl-amide;

(1S,2R)-2-(4-Acetylamino-4-phenyl-piperidin-1-ylmethyl)-1-m-tolyl-cyclopropanecarboxylic acid benzyl-methyl-amide;

(1S,2R)-2-(4-Acetylamino-4-phenyl-piperidin-1-ylmethyl)-1-m-tolyl-cyclopropanecarboxylic acid (4-fluoro-benzyl)-methyl-amide;

(1S,2R)-2-(4-Acetylamino-4-phenyl-piperidin-1-ylmethyl)-1-(3-methoxy-phenyl)-cyclopropanecarboxylic acid (4-fluoro-benzyl)-methyl-amide;

(1S,2R)-2-(4-Acetylamino-4-phenyl-piperidin-1-ylmethyl)-1-(4-methoxy-phenyl)-cyclopropanecarboxylic acid benzyl-methyl-amide;

(1S,2R)-2-(4-Acetylamino-4-phenyl-piperidin-1-ylmethyl)-1-p-tolyl-cyclopropanecarboxylic acid benzyl-methyl-amide;

(1S,2R)-2-(4-Acetylamino-4-phenyl-piperidin-1-ylmethyl)-1-(3-methoxy-phenyl)-cyclopropanecarboxylic acid benzyl-methyl-amide;

(1S,2R)-1-Phenyl-2-(4-phenyl-4-ureido-piperidin-1-ylmethyl)-cyclopropanecarboxylic acid (4-fluoro-benzyl)-methyl-amide;

(1S,2R)-1-(3,4-Dichlorophenyl)-2-(4-phenyl-4-ureido-piperidin-1-ylmethyl)-cyclopropanecarboxylic acid-benzyl-methyl-amide;

(1S,2R)-1-Phenyl-2-[4-(3-methyl-ureido)-4-phenyl-piperidin-1-ylmethyl]-cyclopropanecarboxylic acid (4-fluorobenzyl)-methyl-amide;

(1S,2R)-2-[4-(3-Methyl-ureido)-4-phenyl-piperidin-1-ylmethyl]-1-(3,4-dichlorophenyl)-cyclopropanecarboxylic acid benzyl-methyl-amide;

(1S,2R)-N-(1-{2-[(4-Fluoro-benzyl)-methyl-carbamoyl]-2-phenyl-cyclopropylmethyl}-4-phenyl-piperidin-4-yl)-oxalamide;

(1S,2R)-N-(1-{2-[benzyl-methyl-carbamoyl]-2-(3,4-dichlorophenyl)-cyclopropylmethyl}-4-phenyl-piperidin-4-yl)-oxalamide;

(1S,2R)-1-Phenyl-2-(4-methanesulfonylamino-4-phenyl-piperidin-1-ylmethyl)-cyclopropanecarboxylic acid-(4-fluorobenzyl)-methyl-amide;

(1S,2R)-2-(4-Methanesulfonylamino-4-phenyl-piperidin-1-ylmethyl)-1-(3,4-dichlorophenyl)-cyclopropanecarboxylic acid-benzyl-methyl-amide;

(1S,2R)-{1-[2-((4-fluoro-benzyl)-methyl-carbamoyl]-2-phenyl-cyclopropylmethyl]-4-phenyl-piperidin-4-yl}-carbamic acid methyl ester;

(1S,2R)-(1-{2-benzyl-methyl-carbamoyl]-2-(3,4-dichlorophenyl)-cyclopropylmethyl}-4-phenyl-piperidin-4-yl)-carbamic acid methyl ester;

(1S,2R)-1-(3,4-Dichloro-phenyl)-2-[4-(3,3-dimethyl-ureido)-4-phenyl-piperidin-1-ylmethyl]-cyclopropanecarboxylic acid benzyl-methyl-amide;

(1S,2R)-1-phenyl-2-[4-(3,3-dimethyl-ureido)-4-phenyl-piperidin-1-ylmethyl]-cyclopropanecarboxylic acid (4-fluorobenzyl)-methyl-amide;

(1S,2R)-2-[2-(4-Acetyl amino-4-phenyl-piperidin-1-yl)-ethyl]-1-(3,4-dichlorophenyl)-cyclopropanecarboxylic acid (4-fluoro-benzyl)-methyl-amide;

(1S,2R)-2-[3-(4-Acetylamino-4-phenyl-piperidin-1-yl)-propyl]-1-(3,4-dichlorophenyl)-cyclopropanecarboxylic acid (4-fluoro-benzyl)-methyl-amide;

(1S,2R)-2-[4-(2-Acetylamino-5-fluorophenyl)-piperidin-1-ylmethyl]-1-(3,4-dichlorophenyl)-cyclopropanecarboxylic acid (4-fluoro-benzyl)-methyl-amide;

(1S,2R)-2-(4-Acetylamino-4-phenyl-piperidin-1-ylmethyl)-1-(3,4-dimethylphenyl)-cyclopropanecarboxylic acid (4-fluoro-benzyl)-methyl-amide;

(1S,2R)-2-(4-Acetylamino-4-phenyl-piperidin-1-ylmethyl)-1-(3,4-dichlorophenyl)-cyclopropanecarboxylic acid (4-fluoro-benzyl)-methyl-amide;

(1S,2R)-2-(4-Acetylamino-4-phenyl-piperidin-1-ylmethyl)-1-(3-chlorophenyl)-cyclopropanecarboxylic acid (4-fluoro-benzyl)-methyl-amide;

(1S,2R)-2-(4-Acetylamino-4-phenyl-piperidin-1-ylmethyl)-1-(3-fluorophenyl)-cyclopropanecarboxylic acid (4-fluoro-benzyl)-methyl-amide;

(1S,2R)-1-(3,4-Dichlorophenyl)-2-(4-phenyl-piperidin-1-ylmethyl)-cyclopropanecarboxylic acid methyl-naphthalen-1-ylmethyl-amide;

(1S,2R)-1-(3,4-Dichlorophenyl)-2-[1-acetyl-5-fluoro-spiro[2,3-dihydro-1H-indol-3-yl-3,4'-piperidine-1'-ylmethyl]-cyclopropanecarboxylic acid methyl-naphthalen-1-ylmethyl-amide; and (1S,2R)-1-(3,4-Dichlorophenyl)-2-(4-Acetylamino-4-phenyl-piperidin-1-ylmethyl)-cyclopropanecarboxylic acid methyl-naphthalen-1-ylmethyl-amide;

or a salt thereof.

114. A pharmaceutical composition comprising a compound of claim 1.

115. A method of treating a subject suffering from a disease comprising administering to the subject a therapeutically effective amount of the compound of claim 1, wherein the disease is selected from the group consisting of: psychotic disorders, schizophrenia, depression, anxiety, Parkinson's disease, pain, convulsions, cough, asthma, airway hyperresponsiveness, microvascular hypersensitivity, bronchoconstriction, gut inflammation, inflammatory bowel disease, hypertension, imbalances in water and electrolyte homeostasis, ischemia, oedema, plasma extravasation and obesity.

116. The method of claim 115, wherein the disease is schizophrenia.

117. The method of claim 115, wherein the compound treats the positive symptoms of schizophrenia.

118. A method of treating a subject suffering from a disease or disorder of the central nervous system comprising administering to the subject a therapeutically effective amount of the compound of claim 1.

* * * * *

UNITED STATES PATENT AND TRADEMARK OFFICE
CERTIFICATE OF CORRECTION

| | | |
|---|---|---|
| PATENT NO. | : 7,834,008 B2 | Page 1 of 1 |
| APPLICATION NO. | : 10/568483 | |
| DATED | : November 16, 2010 | |
| INVENTOR(S) | : Kehler et al. | |

It is certified that error appears in the above-identified patent and that said Letters Patent is hereby corrected as shown below:

In the Claims, in Column 57:
    Claim 35, line 37, which reads "from the group consisting of an optionally substituted aryl an" should read -- from the group consisting of an optionally substituted aryl, an --;
    Claim 36, line 42, which reads "36. The compound of claim 34, wherein $R^{11}$ is an aryl as" should read -- 36. The compound of claim 35, wherein $R^{11}$ is an aryl --.

Signed and Sealed this
Fifteenth Day of February, 2011

David J. Kappos
*Director of the United States Patent and Trademark Office*